(12) United States Patent
Marsot et al.

(10) Patent No.: US 11,109,972 B2
(45) Date of Patent: Sep. 7, 2021

(54) DELIVERY CATHETER HANDLE AND METHODS OF USE

(71) Applicant: Evalve, Inc., Santa Clara, CA (US)

(72) Inventors: Travis R. Marsot, Mountain View, CA (US); Patricia H. Ho, Redwood City, CA (US); Justen D. England, Milton, MA (US); Randall S. Koplin, Middleton, WI (US); Douglas S. Rodenkirch, Sun Prairie, WI (US)

(73) Assignee: Evalve, Inc., Santa Clara, CA (US)

( * ) Notice: Subject to any disclaimer, the term of this patent is extended or adjusted under 35 U.S.C. 154(b) by 302 days.

(21) Appl. No.: 16/263,816

(22) Filed: Jan. 31, 2019

(65) Prior Publication Data

US 2019/0159899 A1    May 30, 2019

Related U.S. Application Data

(63) Continuation of application No. 14/879,726, filed on Oct. 9, 2015, now Pat. No. 10,238,495.

(51) Int. Cl.
*A61F 2/24* (2006.01)
*A61B 17/00* (2006.01)
(Continued)

(52) U.S. Cl.
CPC ...... *A61F 2/2466* (2013.01); *A61B 17/00234* (2013.01); *A61B 17/1227* (2013.01);
(Continued)

(58) Field of Classification Search
CPC .... A61F 2/9517; A61F 2/2439; A61F 2/2466; A61F 2002/9511; A61F 2/2454; A61F 2/246; A61M 25/0136; A61M 25/0147; A61M 2025/024; A61B 2017/0496; A61B 2017/00367; A61B 2017/0477;
(Continued)

(56) References Cited

U.S. PATENT DOCUMENTS 2,097,018 A    10/1937    Chamberlain
2,108,206 A    2/1938    Meeker
(Continued)

FOREIGN PATENT DOCUMENTS

CN    102258402 B    11/2014
DE    3504292 C1    7/1986
(Continued)

OTHER PUBLICATIONS

U.S. Appl. No. 14/216,787, filed Mar. 17, 2014, Basude, et al.
(Continued)

*Primary Examiner* — Alexander J Orkin
(74) *Attorney, Agent, or Firm* — Baker Botts L.L.P.

(57) ABSTRACT

Methods, devices, and systems are provided for performing endovascular repair of atrioventricular and other cardiac valves in the heart. A delivery device for staged deployment of an implantable device to a target area. The delivery device includes a deployment handle and one or more lock lines extending from the deployment handle through the catheter to the implantable device, the one or more lock lines being configured to engage with the implantable device to allow locking of the implantable device.

19 Claims, 39 Drawing Sheets

(51) Int. Cl.
*A61B 17/122* (2006.01)
*A61B 17/128* (2006.01)
*A61M 25/01* (2006.01)
*A61B 90/50* (2016.01)
*A61M 25/02* (2006.01)
*A61B 90/57* (2016.01)

(52) U.S. Cl.
CPC .......... *A61B 17/1285* (2013.01); *A61B 90/50* (2016.02); *A61F 2/246* (2013.01); *A61F 2/2454* (2013.01); *A61M 25/0136* (2013.01); *A61B 90/57* (2016.02); *A61B 2017/00243* (2013.01); *A61B 2017/00336* (2013.01); *A61B 2017/00367* (2013.01); *A61B 2017/00429* (2013.01); *A61B 2017/00477* (2013.01); *A61B 2017/00783* (2013.01); *A61B 2090/508* (2016.02); *A61M 2025/024* (2013.01); *A61M 2025/028* (2013.01)

(58) Field of Classification Search
CPC ...... A61B 2017/347; A61B 2017/0046; A61B 17/00234; A61B 17/1227; A61B 17/1285
See application file for complete search history.

(56) References Cited

U.S. PATENT DOCUMENTS

| | | |
|---|---|---|
| 3,296,668 A | 1/1967 | Aiken |
| 3,378,010 A | 4/1968 | Codling et al. |
| 3,557,780 A | 1/1971 | Sato |
| 3,671,979 A | 6/1972 | Moulopoulos |
| 3,675,639 A | 7/1972 | Cimber |
| 3,874,388 A | 4/1975 | King et al. |
| 4,007,743 A | 2/1977 | Blake |
| 4,064,881 A | 12/1977 | Meredith |
| 4,091,815 A | 5/1978 | Larsen |
| 4,112,951 A | 9/1978 | Hulka et al. |
| 4,235,238 A | 11/1980 | Ogiu et al. |
| 4,297,749 A | 11/1981 | Davis et al. |
| 4,458,682 A | 7/1984 | Cerwin |
| 4,425,908 A | 11/1984 | Simon |
| 4,484,579 A | 11/1984 | Meno et al. |
| 4,487,205 A | 12/1984 | Di Giovanni et al. |
| 4,498,476 A | 2/1985 | Cerwin et al. |
| 4,510,934 A | 4/1985 | Batra |
| 4,531,522 A | 7/1985 | Bedi et al. |
| 4,578,061 A | 3/1986 | Lemelson |
| 4,641,366 A | 2/1987 | Yokoyama et al. |
| 4,686,965 A | 8/1987 | Bonnet et al. |
| 4,777,951 A | 10/1988 | Cribier et al. |
| 4,809,695 A | 3/1989 | Gwathmey et al. |
| 4,896,986 A | 1/1990 | Terayama |
| 4,944,295 A | 7/1990 | Gwathmey et al. |
| 4,969,890 A | 11/1990 | Sugita et al. |
| 5,015,249 A | 5/1991 | Nakao et al. |
| 5,019,096 A | 5/1991 | Fox, Jr. et al. |
| 5,042,161 A | 8/1991 | Hodge |
| 5,042,707 A | 8/1991 | Taheri |
| 5,047,041 A | 9/1991 | Samuels |
| 5,049,153 A | 9/1991 | Nakao et al. |
| 5,061,277 A | 10/1991 | Carpentier et al. |
| 5,069,679 A | 12/1991 | Taheri |
| 5,108,368 A | 4/1992 | Hammerslag et al. |
| 5,125,758 A | 6/1992 | DeWan |
| 5,171,252 A | 12/1992 | Friedland |
| 5,171,259 A | 12/1992 | Inoue |
| 5,190,554 A | 3/1993 | Coddington et al. |
| 5,195,968 A | 3/1993 | Lundquist et al. |
| 5,209,756 A | 5/1993 | Seedhom et al. |
| 5,226,429 A | 7/1993 | Kuzmak |
| 5,226,911 A | 7/1993 | Chee et al. |
| 5,234,437 A | 8/1993 | Sepetka |
| 5,236,450 A | 8/1993 | Scott |
| 5,242,456 A | 9/1993 | Nash et al. |
| 5,250,071 A | 10/1993 | Palermo |
| 5,251,611 A | 10/1993 | Zehel et al. |
| 5,254,130 A | 10/1993 | Poncet et al. |
| 5,261,916 A | 11/1993 | Engelson |
| 5,263,939 A | 11/1993 | Wortrich |
| 5,271,381 A | 12/1993 | Ailinger et al. |
| 5,275,578 A | 1/1994 | Adams |
| 5,282,845 A | 2/1994 | Bush et al. |
| 5,304,131 A | 4/1994 | Paskar |
| 5,306,283 A | 4/1994 | Conners |
| 5,306,286 A | 4/1994 | Stack et al. |
| 5,312,415 A | 5/1994 | Palermo |
| 5,314,424 A | 5/1994 | Nicholas |
| 5,318,525 A | 6/1994 | West et al. |
| 5,320,632 A | 6/1994 | Heidmueller |
| 5,325,845 A | 7/1994 | Adair |
| 5,330,442 A | 7/1994 | Green et al. |
| 5,342,393 A | 8/1994 | Stack |
| 5,350,397 A | 9/1994 | Palermo et al. |
| 5,350,399 A | 9/1994 | Erlebacher et al. |
| 5,359,994 A | 11/1994 | Kreuter et al. |
| 5,368,564 A | 11/1994 | Savage |
| 5,368,601 A | 11/1994 | Sauer et al. |
| 5,383,886 A | 1/1995 | Kensey et al. |
| 5,391,182 A | 2/1995 | Chin |
| 5,403,312 A | 4/1995 | Yates et al. |
| 5,403,326 A | 4/1995 | Harrison et al. |
| 5,405,402 A | 4/1995 | Dye et al. |
| 5,417,699 A | 5/1995 | Klein et al. |
| 5,417,700 A | 5/1995 | Egan |
| 5,423,857 A | 6/1995 | Rosenman et al. |
| 5,423,858 A | 6/1995 | Bolanos et al. |
| 5,423,882 A | 6/1995 | Jackman et al. |
| 5,431,666 A | 7/1995 | Sauer et al. |
| 5,437,551 A | 8/1995 | Chalifoux |
| 5,437,681 A | 8/1995 | Meade et al. |
| 5,447,966 A | 9/1995 | Hermes et al. |
| 5,450,860 A | 9/1995 | O'Connor |
| 5,456,400 A | 10/1995 | Shichman et al. |
| 5,456,684 A | 10/1995 | Schmidt et al. |
| 5,462,527 A | 10/1995 | Stevens-Wright et al. |
| 5,464,394 A | 11/1995 | Miller et al. |
| 5,472,044 A | 12/1995 | Hall et al. |
| 5,476,470 A | 12/1995 | Fitzgibbons, Jr. |
| 5,477,856 A | 12/1995 | Lundquist |
| 5,478,309 A | 12/1995 | Sweezer et al. |
| 5,478,353 A | 12/1995 | Yoon |
| 5,487,746 A | 1/1996 | Yu et al. |
| 5,489,296 A | 2/1996 | Love et al. |
| 5,496,332 A | 3/1996 | Sierra et al. |
| 5,507,725 A | 4/1996 | Savage et al. |
| 5,507,755 A | 4/1996 | Gresl et al. |
| 5,507,757 A | 4/1996 | Sauer et al. |
| 5,520,701 A | 5/1996 | Lerch |
| 5,522,873 A | 6/1996 | Jackman et al. |
| 5,527,313 A | 6/1996 | Scott et al. |
| 5,527,321 A | 6/1996 | Hinchliffe |
| 5,527,322 A | 6/1996 | Klein et al. |
| 5,536,251 A | 7/1996 | Evard et al. |
| 5,540,705 A | 7/1996 | Meade et al. |
| 5,542,949 A | 8/1996 | Yoon |
| 5,562,678 A | 10/1996 | Booker |
| 5,569,274 A | 10/1996 | Rapacki et al. |
| 5,571,085 A | 11/1996 | Accisano, III |
| 5,571,137 A | 11/1996 | Marlow et al. |
| 5,571,215 A | 11/1996 | Sterman et al. |
| 5,575,802 A | 11/1996 | McQuilkin et al. |
| 5,582,611 A | 12/1996 | Tsuruta et al. |
| 5,593,424 A | 1/1997 | Northrup, III |
| 5,593,435 A | 1/1997 | Carpentier et al. |
| 5,609,598 A | 3/1997 | Laufer et al. |
| 5,618,306 A | 4/1997 | Roth et al. |
| 5,620,452 A | 4/1997 | Yoon |
| 5,620,461 A | 4/1997 | Muijs Van De Moer et al. |
| 5,626,588 A | 5/1997 | Sauer et al. |
| 5,630,832 A | 5/1997 | Giordano et al. |
| 5,634,932 A | 6/1997 | Schmidt |
| 5,636,634 A | 6/1997 | Kordis et al. |
| 5,639,277 A | 6/1997 | Mariant et al. |

(56) References Cited

U.S. PATENT DOCUMENTS

| | | |
|---|---|---|
| 5,640,955 A | 6/1997 | Ockuly et al. |
| 5,649,937 A | 7/1997 | Bito et al. |
| 5,662,606 A | 9/1997 | Cimino et al. |
| 5,662,681 A | 9/1997 | Nash et al. |
| 5,669,917 A | 9/1997 | Sauer et al. |
| 5,690,671 A | 11/1997 | McGurk et al. |
| 5,695,504 A | 12/1997 | Gifford, III et al. |
| 5,695,505 A | 12/1997 | Yoon |
| 5,702,825 A | 12/1997 | Keita et al. |
| 5,706,824 A | 1/1998 | Whittier |
| 5,709,707 A | 1/1998 | Lock et al. |
| 5,713,910 A | 2/1998 | Gordon et al. |
| 5,713,911 A | 2/1998 | Racene et al. |
| 5,715,817 A | 2/1998 | Stevens-Wright et al. |
| 5,716,367 A | 2/1998 | Koike et al. |
| 5,718,714 A | 2/1998 | Livneh |
| 5,718,725 A | 2/1998 | Sterman et al. |
| 5,719,725 A | 2/1998 | Nakao |
| 5,722,421 A | 3/1998 | Francese et al. |
| 5,725,542 A | 3/1998 | Yoon |
| 5,725,556 A | 3/1998 | Moser et al. |
| 5,738,649 A | 4/1998 | Macoviak |
| 5,741,280 A | 4/1998 | Fleenor |
| 5,741,286 A | 4/1998 | Recuset |
| 5,749,828 A | 5/1998 | Solomon et al. |
| 5,759,193 A | 6/1998 | Burbank et al. |
| 5,769,863 A | 6/1998 | Garrison |
| 5,772,578 A | 6/1998 | Heimberger et al. |
| 5,782,845 A | 7/1998 | Shewchuk |
| 5,797,927 A | 8/1998 | Yoon |
| 5,810,847 A | 9/1998 | Laufer et al. |
| 5,810,849 A | 9/1998 | Kontos |
| 5,810,853 A | 9/1998 | Yoon |
| 5,810,876 A | 9/1998 | Kelleher |
| 5,814,029 A | 9/1998 | Hassett |
| 5,820,592 A | 10/1998 | Hammerslag |
| 5,820,631 A | 10/1998 | Nobles |
| 5,823,955 A | 10/1998 | Kuck et al. |
| 5,824,065 A | 10/1998 | Gross |
| 5,827,237 A | 10/1998 | MacOviak et al. |
| 5,833,671 A | 11/1998 | MacOviak et al. |
| 5,836,955 A | 11/1998 | Buelna et al. |
| 5,843,031 A | 12/1998 | Hermann et al. |
| 5,849,019 A | 12/1998 | Yoon |
| 5,853,422 A | 12/1998 | Huebsch et al. |
| 5,855,271 A | 1/1999 | Eubanks et al. |
| 5,855,590 A | 1/1999 | Malecki et al. |
| 5,860,990 A | 1/1999 | Nobles et al. |
| 5,861,003 A | 1/1999 | Latson et al. |
| 5,868,733 A | 2/1999 | Ockuly et al. |
| 5,871,493 A | 2/1999 | Sjostrom et al. |
| 5,876,399 A | 3/1999 | Chia et al. |
| 5,879,307 A | 3/1999 | Chio et al. |
| 5,885,271 A | 3/1999 | Hamilton et al. |
| 5,891,160 A | 4/1999 | Williamson, IV et al. |
| 5,902,290 A | 5/1999 | Peacock, III et al. |
| 5,916,147 A | 6/1999 | Boury |
| 5,928,224 A | 7/1999 | Laufer |
| 5,944,733 A | 8/1999 | Engelson |
| 5,947,363 A | 9/1999 | Bolduc et al. |
| 5,954,732 A | 9/1999 | Hart et al. |
| 5,957,949 A | 9/1999 | Leonhard et al. |
| 5,964,717 A | 10/1999 | Gottlieb et al. |
| 5,972,020 A | 10/1999 | Carpentier et al. |
| 5,972,030 A | 10/1999 | Garrison et al. |
| 5,980,455 A | 11/1999 | Daniel et al. |
| 5,989,284 A | 11/1999 | Laufer |
| 5,993,470 A | 11/1999 | Yoon |
| 6,015,417 A | 1/2000 | Reynolds, Jr. |
| 6,019,722 A | 2/2000 | Spence et al. |
| 6,022,360 A | 2/2000 | Reimels et al. |
| 6,033,378 A | 3/2000 | Lundquist et al. |
| 6,036,699 A | 3/2000 | Andreas et al. |
| 6,048,351 A | 4/2000 | Gordon et al. |
| 6,056,769 A | 5/2000 | Epstein et al. |
| 6,059,757 A | 5/2000 | Macoviak et al. |
| 6,060,628 A | 5/2000 | Aoyama et al. |
| 6,060,629 A | 5/2000 | Pham et al. |
| 6,063,106 A | 5/2000 | Gibson |
| 6,066,146 A | 5/2000 | Carroll et al. |
| 6,068,628 A | 5/2000 | Fanton et al. |
| 6,068,629 A | 5/2000 | Haissaguerre et al. |
| 6,077,214 A | 6/2000 | Mortier et al. |
| 6,086,600 A | 7/2000 | Kortenbach |
| 6,088,889 A | 7/2000 | Luther et al. |
| 6,099,505 A | 8/2000 | Ryan et al. |
| 6,099,553 A | 8/2000 | Hart et al. |
| 6,110,145 A | 8/2000 | Macoviak |
| 6,117,144 A | 9/2000 | Nobles et al. |
| 6,117,159 A | 9/2000 | Huebsch et al. |
| 6,123,699 A | 9/2000 | Webster, Jr. |
| 6,126,658 A | 10/2000 | Baker |
| 6,132,447 A | 10/2000 | Dorsey |
| 6,136,010 A | 10/2000 | Modesitt et al. |
| 6,139,214 A | 10/2000 | Zirps et al. |
| 6,143,024 A | 11/2000 | Campbell et al. |
| 6,159,240 A | 12/2000 | Sparer et al. |
| 6,162,233 A | 12/2000 | Williamson, IV et al. |
| 6,165,164 A | 12/2000 | Hill et al. |
| 6,165,183 A | 12/2000 | Kuehn et al. |
| 6,165,204 A | 12/2000 | Levinson et al. |
| 6,168,614 B1 | 1/2001 | Andersen et al. |
| 6,171,320 B1 | 1/2001 | Monassevitch |
| 6,182,664 B1 | 2/2001 | Cosgrove |
| 6,187,003 B1 | 2/2001 | Buysse et al. |
| 6,190,408 B1 | 2/2001 | Melvin |
| 6,203,531 B1 | 3/2001 | Ockuly et al. |
| 6,203,553 B1 | 3/2001 | Robertson et al. |
| 6,206,893 B1 | 3/2001 | Klein et al. |
| 6,206,907 B1 | 3/2001 | Marino et al. |
| 6,210,419 B1 | 4/2001 | Mayenberger et al. |
| 6,210,432 B1 | 4/2001 | Solem et al. |
| 6,245,079 B1 | 6/2001 | Nobles et al. |
| 6,267,746 B1 | 7/2001 | Bumbalough |
| 6,267,781 B1 | 7/2001 | Tu |
| 6,269,819 B1 | 8/2001 | Oz et al. |
| 6,277,555 B1 | 8/2001 | Duran et al. |
| 6,283,127 B1 | 9/2001 | Sterman et al. |
| 6,283,962 B1 | 9/2001 | Tu et al. |
| 6,299,637 B1 | 10/2001 | Shaolian et al. |
| 6,306,133 B1 | 10/2001 | Tu et al. |
| 6,312,447 B1 | 11/2001 | Grimes |
| 6,319,250 B1 | 11/2001 | Falwell et al. |
| 6,322,559 B1 | 11/2001 | Daulton et al. |
| 6,332,893 B1 | 12/2001 | Mortier et al. |
| 6,350,281 B1 | 2/2002 | Rhee |
| 6,352,708 B1 | 3/2002 | Duran et al. |
| 6,355,030 B1 | 3/2002 | Aldrich et al. |
| 6,358,277 B1 | 3/2002 | Duran |
| 6,368,326 B1 | 4/2002 | Dakin et al. |
| 6,387,104 B1 | 5/2002 | Pugsley, Jr. et al. |
| 6,402,780 B2 | 6/2002 | Williamson et al. |
| 6,402,781 B1 | 6/2002 | Langberg et al. |
| 6,406,420 B1 | 6/2002 | McCarthy et al. |
| 6,419,669 B1 | 7/2002 | Frazier et al. |
| 6,461,366 B1 | 10/2002 | Seguin |
| 6,464,707 B1 | 10/2002 | Bjerken |
| 6,482,224 B1 | 11/2002 | Michler et al. |
| 6,485,489 B2 | 11/2002 | Teirstein et al. |
| 6,508,828 B1 | 1/2003 | Akerfeldt et al. |
| 6,533,796 B1 | 3/2003 | Sauer et al. |
| 6,537,314 B2 | 3/2003 | Langberg et al. |
| 6,540,755 B2 | 4/2003 | Ockuly et al. |
| 6,551,331 B2 | 4/2003 | Nobles et al. |
| 6,562,037 B2 | 5/2003 | Paton et al. |
| 6,562,052 B2 | 5/2003 | Nobles et al. |
| 6,575,971 B2 | 6/2003 | Hauck et al. |
| 6,585,761 B2 | 7/2003 | Taheri |
| 6,599,311 B1 | 7/2003 | Biggs et al. |
| 6,616,684 B1 | 9/2003 | Vidlund et al. |
| 6,619,291 B2 | 9/2003 | Hlavka et al. |
| 6,626,899 B2 | 9/2003 | Houser et al. |
| 6,626,930 B1 | 9/2003 | Allen et al. |
| 6,629,534 B1 | 10/2003 | St. Goar et al. |

(56) References Cited

U.S. PATENT DOCUMENTS

| | | |
|---|---|---|
| 6,641,592 B1 | 11/2003 | Sauer et al. |
| 6,656,221 B2 | 12/2003 | Taylor et al. |
| 6,669,687 B1 | 12/2003 | Saadat |
| 6,685,648 B2 | 2/2004 | Flaherty et al. |
| 6,689,164 B1 | 2/2004 | Seguin |
| 6,695,866 B1 | 2/2004 | Kuehn et al. |
| 6,701,929 B2 | 3/2004 | Hussein |
| 6,702,825 B2 | 3/2004 | Frazier et al. |
| 6,702,826 B2 | 3/2004 | Liddicoat et al. |
| 6,709,382 B1 | 3/2004 | Homer |
| 6,709,456 B2 | 3/2004 | Langberg et al. |
| 6,718,985 B2 | 4/2004 | Hlavka et al. |
| 6,719,767 B1 | 4/2004 | Kimblad |
| 6,723,038 B1 | 4/2004 | Schroeder et al. |
| 6,726,716 B2 | 4/2004 | Marquez |
| 6,740,107 B2 | 5/2004 | Loeb et al. |
| 6,746,471 B2 | 6/2004 | Mortier et al. |
| 6,752,813 B2 | 6/2004 | Goldfarb et al. |
| 6,755,777 B2 | 6/2004 | Schweich et al. |
| 6,764,510 B2 | 7/2004 | Vidlund et al. |
| 6,767,349 B2 | 7/2004 | Ouchi |
| 6,770,083 B2 | 8/2004 | Seguin |
| 6,797,001 B2 | 9/2004 | Mathis et al. |
| 6,797,002 B2 | 9/2004 | Spence et al. |
| 6,860,179 B2 | 3/2005 | Hopper et al. |
| 6,875,224 B2 | 4/2005 | Grimes |
| 6,926,715 B1 | 8/2005 | Hauck et al. |
| 6,945,978 B1 | 9/2005 | Hyde |
| 6,949,122 B2 | 9/2005 | Adams et al. |
| 6,966,914 B2 | 11/2005 | Abe |
| 6,986,775 B2 | 1/2006 | Morales et al. |
| 7,004,970 B2 | 2/2006 | Cauthen, III et al. |
| 7,011,669 B2 | 3/2006 | Kimblad |
| 7,048,754 B2 | 5/2006 | Martin et al. |
| 7,112,207 B2 | 9/2006 | Allen et al. |
| 7,226,467 B2 | 6/2007 | Lucatero et al. |
| 7,288,097 B2 | 10/2007 | Seguin |
| 7,381,210 B2 | 6/2008 | Zarbatany et al. |
| 7,464,712 B2 | 12/2008 | Oz et al. |
| 7,497,822 B1 | 3/2009 | Kugler et al. |
| 7,533,790 B1 | 5/2009 | Knodel et al. |
| 7,563,267 B2 | 7/2009 | Goldfarb et al. |
| 7,563,273 B2 | 7/2009 | Goldfarb et al. |
| 7,604,646 B2 | 10/2009 | Goldfarb et al. |
| 7,635,329 B2 | 12/2009 | Goldfarb et al. |
| 7,651,502 B2 | 1/2010 | Jackson |
| 7,655,015 B2 | 2/2010 | Goldfarb et al. |
| 7,666,204 B2 | 2/2010 | Thornton et al. |
| 8,216,256 B2 | 7/2012 | Raschdorf, Jr. et al. |
| D668,334 S | 10/2012 | Makowski et al. |
| D740,414 S | 10/2015 | Katsura |
| 9,700,445 B2 | 7/2017 | Martin et al. |
| D809,139 S | 1/2018 | Marsot et al. |
| 2001/0004715 A1 | 6/2001 | Duran et al. |
| 2001/0005787 A1 | 6/2001 | Oz et al. |
| 2001/0007067 A1 | 7/2001 | Kurfess et al. |
| 2001/0010005 A1 | 7/2001 | Kammerer et al. |
| 2001/0018611 A1 | 8/2001 | Solem et al. |
| 2001/0022872 A1 | 9/2001 | Marui |
| 2001/0037084 A1 | 11/2001 | Nardeo |
| 2001/0039411 A1 | 11/2001 | Johansson et al. |
| 2001/0044568 A1 | 11/2001 | Langberg et al. |
| 2002/0013571 A1 | 1/2002 | Goldfarb et al. |
| 2002/0022848 A1 | 2/2002 | Garrison et al. |
| 2002/0026233 A1 | 2/2002 | Shaknovich |
| 2002/0035361 A1 | 3/2002 | Houser et al. |
| 2002/0035381 A1 | 3/2002 | Bardy et al. |
| 2002/0042651 A1 | 4/2002 | Liddicoat et al. |
| 2002/0055767 A1 | 5/2002 | Forde et al. |
| 2002/0055774 A1 | 5/2002 | Liddicoat |
| 2002/0055775 A1 | 5/2002 | Carpentier et al. |
| 2002/0058910 A1 | 5/2002 | Hermann et al. |
| 2002/0058995 A1 | 5/2002 | Stevens |
| 2002/0077687 A1 | 6/2002 | Ahn |
| 2002/0087148 A1 | 7/2002 | Brock et al. |
| 2002/0087169 A1 | 7/2002 | Brock et al. |
| 2002/0087173 A1 | 7/2002 | Alferness et al. |
| 2002/0103532 A1 | 8/2002 | Langberg et al. |
| 2002/0107534 A1 | 8/2002 | Schaefer et al. |
| 2002/0147456 A1 | 10/2002 | Diduch et al. |
| 2002/0156526 A1 | 10/2002 | Hilavka et al. |
| 2002/0158528 A1 | 10/2002 | Tsuzaki et al. |
| 2002/0161378 A1 | 10/2002 | Downing |
| 2002/0169360 A1 | 11/2002 | Taylor et al. |
| 2002/0183766 A1 | 12/2002 | Seguin |
| 2002/0183787 A1 | 12/2002 | Wahr et al. |
| 2002/0183835 A1 | 12/2002 | Taylor et al. |
| 2003/0005797 A1 | 1/2003 | Hopper et al. |
| 2003/0045778 A1 | 3/2003 | Ohline et al. |
| 2003/0050693 A1 | 3/2003 | Quijano et al. |
| 2003/0069570 A1 | 4/2003 | Witzel et al. |
| 2003/0069593 A1 | 4/2003 | Tremulis et al. |
| 2003/0069636 A1 | 4/2003 | Solem et al. |
| 2003/0074012 A1 | 4/2003 | Nguyen et al. |
| 2003/0078654 A1 | 4/2003 | Taylor et al. |
| 2003/0083742 A1 | 5/2003 | Spence et al. |
| 2003/0105519 A1 | 6/2003 | Fasol et al. |
| 2003/0105520 A1 | 6/2003 | Alferness et al. |
| 2003/0120340 A1 | 6/2003 | Lisk et al. |
| 2003/0120341 A1 | 6/2003 | Shennib et al. |
| 2003/0130669 A1 | 7/2003 | Damarati |
| 2003/0130730 A1 | 7/2003 | Cohn et al. |
| 2003/0144697 A1 | 7/2003 | Mathis et al. |
| 2003/0167071 A1 | 9/2003 | Martin et al. |
| 2003/0171776 A1 | 9/2003 | Adams et al. |
| 2003/0181855 A1 | 9/2003 | Simpson et al. |
| 2003/0187467 A1 | 10/2003 | Schreck |
| 2003/0195562 A1 | 10/2003 | Collier et al. |
| 2003/0208231 A1 | 11/2003 | Williamson, IV et al. |
| 2003/0229395 A1 | 12/2003 | Cox |
| 2003/0233038 A1 | 12/2003 | Hassett |
| 2004/0002719 A1 | 1/2004 | Oz et al. |
| 2004/0003819 A1 | 1/2004 | St. Goar et al. |
| 2004/0019377 A1 | 1/2004 | Taylor et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0039442 A1 | 2/2004 | St. Goar et al. |
| 2004/0039443 A1 | 2/2004 | Solem et al. |
| 2004/0044350 A1 | 3/2004 | Martin et al. |
| 2004/0044365 A1 | 3/2004 | Bachman |
| 2004/0049211 A1 | 3/2004 | Tremulis et al. |
| 2004/0073302 A1 | 4/2004 | Rourke et al. |
| 2004/0078053 A1 | 4/2004 | Berg et al. |
| 2004/0087975 A1 | 5/2004 | Lucatero et al. |
| 2004/0088047 A1 | 5/2004 | Spence et al. |
| 2004/0092962 A1 | 5/2004 | Thorton et al. |
| 2004/0097878 A1 | 5/2004 | Anderson et al. |
| 2004/0097979 A1 | 5/2004 | Svanidze et al. |
| 2004/0106989 A1 | 6/2004 | Wilson et al. |
| 2004/0111099 A1 | 6/2004 | Nguyen et al. |
| 2004/0122448 A1 | 6/2004 | Levine |
| 2004/0127981 A1 | 7/2004 | Randert et al. |
| 2004/0127982 A1 | 7/2004 | Machold et al. |
| 2004/0127983 A1 | 7/2004 | Mortier et al. |
| 2004/0133062 A1 | 7/2004 | Pai et al. |
| 2004/0133063 A1 | 7/2004 | McCarthy et al. |
| 2004/0133082 A1 | 7/2004 | Abraham-Fuchs et al. |
| 2004/0133192 A1 | 7/2004 | Houser et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138675 A1 | 7/2004 | Crabtree |
| 2004/0138744 A1 | 7/2004 | Lashinski et al. |
| 2004/0138745 A1 | 7/2004 | Macoviak et al. |
| 2004/0148021 A1 | 7/2004 | Cartledge et al. |
| 2004/0152847 A1 | 8/2004 | Emri et al. |
| 2004/0152947 A1 | 8/2004 | Schroeder et al. |
| 2004/0153144 A1 | 8/2004 | Seguin |
| 2004/0158123 A1 | 8/2004 | Jayaraman |
| 2004/0162610 A1 | 8/2004 | Laiska et al. |
| 2004/0167539 A1 | 8/2004 | Kuehn et al. |
| 2004/0186486 A1 | 9/2004 | Roue et al. |
| 2004/0186566 A1 | 9/2004 | Hindrichs et al. |

(56) References Cited

U.S. PATENT DOCUMENTS

| | | |
|---|---|---|
| 2004/0193191 A1 | 9/2004 | Starksen et al. |
| 2004/0215339 A1 | 10/2004 | Drasler et al. |
| 2004/0220593 A1 | 11/2004 | Greenhalgh |
| 2004/0220657 A1 | 11/2004 | Nieminen et al. |
| 2004/0225300 A1 | 11/2004 | Goldfarb et al. |
| 2004/0236354 A1 | 11/2004 | Seguin |
| 2004/0243227 A1 | 12/2004 | Starksen et al. |
| 2004/0243229 A1 | 12/2004 | Vidlund et al. |
| 2004/0249452 A1 | 12/2004 | Adams et al. |
| 2004/0249453 A1 | 12/2004 | Cartledge et al. |
| 2004/0260393 A1 | 12/2004 | Randert et al. |
| 2005/0004583 A1 | 1/2005 | Oz et al. |
| 2005/0004665 A1 | 1/2005 | Aklog |
| 2005/0004668 A1 | 1/2005 | Aklog et al. |
| 2005/0006432 A1 | 1/2005 | Racenet et al. |
| 2005/0021056 A1 | 1/2005 | St. Goer et al. |
| 2005/0021057 A1 | 1/2005 | St. Goer et al. |
| 2005/0021058 A1 | 1/2005 | Negro |
| 2005/0033446 A1 | 2/2005 | Deem et al. |
| 2005/0038508 A1 | 2/2005 | Gabbay |
| 2005/0049698 A1 | 3/2005 | Bolling et al. |
| 2005/0055089 A1 | 3/2005 | Macoviak et al. |
| 2005/0059351 A1 | 3/2005 | Cauwels et al. |
| 2005/0096666 A1* | 5/2005 | Gordon ............... A61F 2/2451 606/108 |
| 2005/0149014 A1 | 7/2005 | Hauck et al. |
| 2005/0159810 A1 | 7/2005 | Filsoufi |
| 2005/0197694 A1 | 9/2005 | Pai et al. |
| 2005/0197695 A1 | 9/2005 | Stacchino et al. |
| 2005/0216039 A1 | 9/2005 | Lederman |
| 2005/0228422 A1 | 10/2005 | Machold et al. |
| 2005/0228495 A1 | 10/2005 | Macoviak |
| 2005/0251001 A1 | 11/2005 | Hassett |
| 2005/0267493 A1 | 12/2005 | Schreck et al. |
| 2005/0273160 A1 | 12/2005 | Lashinski et al. |
| 2005/0287493 A1 | 12/2005 | Novak et al. |
| 2006/0004247 A1 | 1/2006 | Kute et al. |
| 2006/0009715 A1 | 1/2006 | Khairkhahan et al. |
| 2006/0015003 A1 | 1/2006 | Moaddes et al. |
| 2006/0020275 A1 | 1/2006 | Goldfarb et al. |
| 2006/0030866 A1 | 2/2006 | Schreck |
| 2006/0030867 A1 | 2/2006 | Zadno |
| 2006/0030885 A1 | 2/2006 | Hyde |
| 2006/0058871 A1 | 3/2006 | Zakay et al. |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0089671 A1 | 4/2006 | Goldfarb et al. |
| 2006/0089711 A1 | 4/2006 | Dolan |
| 2006/0135993 A1 | 6/2006 | Seguin |
| 2006/0173524 A1* | 8/2006 | Salahieh ............... A61F 2/2418 623/1.11 |
| 2006/0184203 A1 | 8/2006 | Martin et al. |
| 2006/0195012 A1 | 8/2006 | Mortier et al. |
| 2006/0229708 A1 | 10/2006 | Powell et al. |
| 2006/0252984 A1 | 11/2006 | Randert et al. |
| 2006/0287643 A1 | 12/2006 | Perlin |
| 2007/0038293 A1 | 2/2007 | St. Goar et al. |
| 2007/0088277 A1 | 4/2007 | McGinley et al. |
| 2007/0088431 A1 | 4/2007 | Bourang et al. |
| 2007/0100356 A1 | 5/2007 | Lucatero et al. |
| 2007/0118155 A1 | 5/2007 | Goldfarb et al. |
| 2007/0129737 A1 | 6/2007 | Goldfarb et al. |
| 2007/0198082 A1 | 8/2007 | Kapadia et al. |
| 2008/0039935 A1 | 2/2008 | Buch et al. |
| 2008/0051703 A1 | 2/2008 | Thornton et al. |
| 2008/0051807 A1 | 2/2008 | St. Goar et al. |
| 2008/0097489 A1 | 4/2008 | Goldfarb et al. |
| 2008/0154299 A1 | 6/2008 | Livneh |
| 2008/0167714 A1 | 7/2008 | St. Goer et al. |
| 2008/0183194 A1 | 7/2008 | Goldfarb et al. |
| 2009/0143851 A1 | 6/2009 | Paul, Jr. |
| 2009/0156995 A1 | 6/2009 | Martin et al. |
| 2009/0163934 A1 | 6/2009 | Raschdorf, Jr. |
| 2009/0177266 A1 | 7/2009 | Powell et al. |
| 2009/0198322 A1 | 8/2009 | Deem et al. |
| 2009/0270858 A1 | 10/2009 | Hauck et al. |
| 2009/0326567 A1 | 12/2009 | Goldfarb et al. |
| 2010/0016958 A1 | 1/2010 | St. Goer et al. |
| 2010/0168717 A1 | 7/2010 | Grasse et al. |
| 2010/0217184 A1 | 8/2010 | Koblish et al. |
| 2010/0252293 A1 | 10/2010 | Lopano et al. |
| 2011/0077498 A1 | 3/2011 | McDaniel |
| 2011/0190778 A1 | 8/2011 | Arpasi et al. |
| 2011/0208169 A1 | 8/2011 | Nash |
| 2012/0089136 A1 | 4/2012 | Levin et al. |
| 2012/0253329 A1 | 10/2012 | Zemlok et al. |
| 2012/0330408 A1 | 12/2012 | Hillukka et al. |
| 2013/0053822 A1 | 2/2013 | Fischell et al. |
| 2013/0066342 A1 | 3/2013 | Dell et al. |
| 2013/0289696 A1* | 10/2013 | Maggard ............... A61F 2/954 623/1.12 |
| 2013/0304117 A1 | 11/2013 | Sugiyama |
| 2013/0310813 A1 | 11/2013 | Kaercher et al. |
| 2014/0012287 A1 | 1/2014 | Oyola et al. |
| 2014/0025103 A1 | 1/2014 | Hundertmark et al. |
| 2014/0148651 A1 | 5/2014 | Aman et al. |
| 2014/0148673 A1 | 5/2014 | Bogusky |
| 2014/0171923 A1 | 6/2014 | Aranyi |
| 2014/0196923 A1 | 7/2014 | Leupert et al. |
| 2014/0243969 A1 | 8/2014 | Venkatasubramanian et al. |
| 2015/0060516 A1 | 3/2015 | Collings et al. |
| 2015/0182334 A1 | 7/2015 | Bourang et al. |
| 2015/0257877 A1 | 9/2015 | Hernandez |
| 2015/0272759 A1 | 10/2015 | Argentine |
| 2015/0306806 A1 | 10/2015 | Dando et al. |
| 2016/0174979 A1 | 6/2016 | Wei |
| 2016/0367787 A1 | 12/2016 | Van Hoven et al. |
| 2016/0374811 A1 | 12/2016 | McNiven et al. |
| 2017/0035566 A1 | 2/2017 | Krone et al. |
| 2017/0224319 A1 | 8/2017 | Martin et al. |

FOREIGN PATENT DOCUMENTS

| | | |
|---|---|---|
| DE | 101 16 168 A1 | 11/2001 |
| EP | 0 179 562 B1 | 7/1989 |
| EP | 0 558 031 B1 | 2/1993 |
| EP | 0 684 012 A2 | 11/1995 |
| EP | 0 727 239 A2 | 8/1996 |
| EP | 0 782 836 A1 | 7/1997 |
| EP | 0 990 449 A2 | 4/2000 |
| EP | 1 230 899 A1 | 8/2002 |
| EP | 1 674 040 A2 | 6/2006 |
| EP | 2 465 568 A1 | 6/2012 |
| FR | 2 768 324 A1 | 3/1999 |
| GB | 1 598 111 A | 9/1981 |
| GB | 2 151 142 A | 7/1985 |
| GB | 2 222 951 A | 3/1990 |
| JP | 09-253030 A | 9/1997 |
| JP | 11-089937 A | 4/1999 |
| JP | 2000-283130 A | 10/2000 |
| JP | 2015-502548 A | 1/2015 |
| WO | WO 81/00668 A1 | 3/1981 |
| WO | WO 91/18881 A1 | 12/1991 |
| WO | WO 92/12690 A1 | 8/1992 |
| WO | WO 94/18881 A1 | 9/1994 |
| WO | WO 94/18893 A1 | 9/1994 |
| WO | WO 95/11620 A2 | 5/1995 |
| WO | WO 95/15715 A1 | 6/1995 |
| WO | WO 96/14032 A1 | 5/1996 |
| WO | WO 96/20655 A1 | 7/1996 |
| WO | WO 96/22735 A1 | 8/1996 |
| WO | WO 96/30072 A1 | 10/1996 |
| WO | WO 97/18746 A2 | 5/1997 |
| WO | WO 97/25927 A1 | 7/1997 |
| WO | WO 97/26034 A1 | 7/1997 |
| WO | WO 97/38748 A2 | 10/1997 |
| WO | WO 97/39688 A2 | 10/1997 |
| WO | WO 97/48436 A2 | 12/1997 |
| WO | WO 98/07375 A1 | 2/1998 |
| WO | WO 98/24372 A1 | 6/1998 |
| WO | WO 98/30153 A1 | 7/1998 |
| WO | WO 98/32382 A1 | 7/1998 |
| WO | WO 99/07354 A2 | 2/1999 |

(56) References Cited

FOREIGN PATENT DOCUMENTS

| | | |
|---|---|---|
| WO | WO 99/13777 A1 | 3/1999 |
| WO | WO 00/02489 A1 | 1/2000 |
| WO | WO 00/03651 A1 | 1/2000 |
| WO | WO 00/12168 A1 | 3/2000 |
| WO | WO 00/44313 A1 | 8/2000 |
| WO | WO 00/59382 A1 | 10/2000 |
| WO | WO 00/60995 A2 | 10/2000 |
| WO | WO 01/00111 A1 | 1/2001 |
| WO | WO 01/00114 A1 | 1/2001 |
| WO | WO 01/03651 A2 | 1/2001 |
| WO | WO 01/26557 A1 | 4/2001 |
| WO | WO 01/26586 A1 | 4/2001 |
| WO | WO 01/26587 A1 | 4/2001 |
| WO | WO 01/26588 A2 | 4/2001 |
| WO | WO 01/26703 A1 | 4/2001 |
| WO | WO 01/28432 A1 | 4/2001 |
| WO | WO 01/28455 A1 | 4/2001 |
| WO | WO 01/47438 A1 | 7/2001 |
| WO | WO 01/49213 A2 | 7/2001 |
| WO | WO 01/50985 A1 | 7/2001 |
| WO | WO 01/54618 A1 | 8/2001 |
| WO | WO 01/56512 A1 | 8/2001 |
| WO | WO 01/66001 A2 | 9/2001 |
| WO | WO 01/70320 A1 | 9/2001 |
| WO | WO 01/89440 A2 | 11/2001 |
| WO | WO 01/95831 A2 | 12/2001 |
| WO | WO 01/95832 A2 | 12/2001 |
| WO | WO 01/97741 A2 | 12/2001 |
| WO | WO 02/00099 A2 | 1/2002 |
| WO | WO 02/01999 A2 | 1/2002 |
| WO | WO 02/03892 A1 | 1/2002 |
| WO | WO 02/34167 A2 | 5/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 03/001893 A2 | 1/2003 |
| WO | WO 03/003930 A1 | 1/2003 |
| WO | WO 03/020179 A1 | 3/2003 |
| WO | WO 03/028558 A2 | 4/2003 |
| WO | WO 03/037171 A2 | 5/2003 |
| WO | WO 03/047467 A1 | 6/2003 |
| WO | WO 03/049619 A2 | 6/2003 |
| WO | WO 03/073910 A2 | 9/2003 |
| WO | WO 03/073913 A2 | 9/2003 |
| WO | WO 03/082129 A2 | 10/2003 |
| WO | WO 03/105667 A2 | 12/2003 |
| WO | WO 2004/004607 A1 | 1/2004 |
| WO | WO 2004/012583 A2 | 2/2004 |
| WO | WO 2004/012789 A2 | 2/2004 |
| WO | WO 2004/014282 A2 | 2/2004 |
| WO | WO 2004/019811 A2 | 3/2004 |
| WO | WO 2004/030570 A2 | 4/2004 |
| WO | WO 2004/037317 A2 | 5/2004 |
| WO | WO 2004/045370 A2 | 6/2004 |
| WO | WO 2004/045378 A2 | 6/2004 |
| WO | WO 2004/045463 A2 | 6/2004 |
| WO | WO 2004/047679 A1 | 6/2004 |
| WO | WO 2004/062725 A1 | 7/2004 |
| WO | WO 2004/082523 A2 | 9/2004 |
| WO | WO 2004/082538 A2 | 9/2004 |
| WO | WO 2004/093730 A2 | 11/2004 |
| WO | WO 2004/103162 A2 | 12/2004 |
| WO | WO 2004/112585 A2 | 12/2004 |
| WO | WO 2004/112651 A2 | 12/2004 |
| WO | WO 2005/002424 A2 | 1/2005 |
| WO | WO 2005/018507 A2 | 3/2005 |
| WO | WO 2005/027797 A2 | 3/2005 |
| WO | WO 2005/032421 A2 | 4/2005 |
| WO | WO 2005/062931 A2 | 7/2005 |
| WO | WO 2005/112792 A2 | 12/2005 |
| WO | WO 2006/037073 A2 | 4/2006 |
| WO | WO 2006/105008 A1 | 10/2006 |
| WO | WO 2006/105009 A1 | 10/2006 |
| WO | WO 2006/115875 A2 | 11/2006 |
| WO | WO 2006/115876 A2 | 11/2006 |
| WO | WO 2007/047488 A2 | 4/2007 |
| WO | WO 2008/031103 A2 | 3/2008 |
| WO | WO 2009/121001 A1 | 10/2009 |
| WO | WO 2011/082350 A1 | 7/2011 |
| WO | WO 2012/151543 A1 | 11/2012 |
| WO | WO 2014/182797 A1 | 11/2014 |
| WO | WO 2015/061052 A1 | 4/2015 |
| WO | WO 2016/204954 A1 | 12/2016 |
| WO | WO 2017/003606 A1 | 1/2017 |
| WO | WO 2017/023534 A2 | 2/2017 |

OTHER PUBLICATIONS

U.S. Appl. No. 15/662,084, filed Jul. 27, 2017, Prabhu, et al.
U.S. Appl. No. 29/633,930, filed Jan. 17, 2018, Marsot, et al.
U.S. Appl. No. 29/505,404, filed Oct. 9, 2015, Marsot, et al.
U.S. Appl. No. 14/879,726 (U.S. Pat. No. 10,238,495), filed Oct. 9, 2015 (Mar. 26, 2019).
U.S. Appl. No. 14/879,726, Jan. 31, 2019 Issue Fee Payment.
U.S. Appl. No. 14/879,726, Dec. 26, 2018 Notice of Allowance.
U.S. Appl. No. 14/879,726, Nov. 8, 2018 Notice of Allowance.
U.S. Appl. No. 14/879,726, Sep. 26, 2018 Request for Continued Examination (RCE).
U.S. Appl. No. 14/879,726, Sep. 5, 2018 Notice of Allowance.
U.S. Appl. No. 14/879,726, Jul. 20, 2018 Amendment and Request for Continued Examination (RCE).
U.S. Appl. No. 14/879,726, Jul. 10, 2018 Advisory Action.
U.S. Appl. No. 14/879,726, Jun. 20, 2018 Response after Final Action.
U.S. Appl. No. 14/879,726, Apr. 20, 2018 Final Office Action.
U.S. Appl. No. 14/879,726, Jan. 23, 2018 Response to Non-Final Office Action.
U.S. Appl. No. 14/879,726, Dec. 12, 2017 Applicant Initiated Interview Summary.
U.S. Appl. No. 14/879,726, Oct. 2, 2017 Non-Final Office Action.
Agricola et al., "Mitral Valve Reserve in Double Orifice Technique: an Exercise Echocardiographic Study," Journal of Heart Valve Disease, 11(5):637-643 (2002).
Alfieri et al., "An Effective Technique to Correct Anterior Mitral Leaflet Prolapse," J. Card Surg., 14:468-470 (1999).
Alfieri et al., "Novel Suture Device for Beating Heart Mitral Leaflet Approximation," Annals of Thoracic Surgery, 74:1488-1493 (2002).
Alfieri et al., "The double orifice technique in mitral valve repair: a simple solution for complex problems," Journal of Thoracic and Cardiovascular Surgery, 122:674-681 (2001).
Alfieri et al., "The Edge to Edge Technique," The European Association for Cardio-Thoracic Surgery, 14th Annual Meeting, Frankfurt / Germany, Oct. 7-11, 2000, Post Graduate Courses, Book of Proceedings.
Alfieri, "The Edge-to-Edge Repair of the Mitral Valve," [Abstract] 6th Annual New Era Cardiac Care: Innovation & Technology, Heart Surgery Forum, (Jan. 2003) pp. 103.
Arisi et al., "Mitral Valve Repair with Alfieri Technique in Mitral Regurgitation of Diverse Etiology: Early Echocardiographic Results," Circulation Supplement II, 104(17):3240 (2001).
Bailey, "Mitral Regurgitation" in Surgery of the Heart, Chapter 20, pp. 686-737 (1955).
Bernal et al., "The Valve Racket': a new and different concept of atrioventricular valve repair," Eur. J. Cardio-thoracic Surgery 29:1026-1029 (2006).
Bhudia et al., "Edge-to-Edge (Alfieri) Mitral Repair: Results in Diverse Clinical Settings," Ann Thorac Surg, 77:1598-1606 (2004).
Bhudia et al., "Edge-to-edge Mitral Repair: A Versatile Mitral Repair," http://www.sts.org/doc/7007 accessed on Sep. 24, 2008.
Borghetti et al., "Preliminary observations on haemodynamics during physiological stress conditions following 'double-orifice' mitral valve repair," European Journal of Cardio-thoracic Surgery, 20:262-269 (2001).
Castedo, "Edge-to-Edge Tricuspid Repair for Redeveloped Valve Incompetence after DeVega's Annuloplasty," Ann Thora Surg., 75:605-606 (2003).

(56) References Cited

OTHER PUBLICATIONS

Chinese Office Action dated Sep. 9, 2013 in Application No. 200980158707.2 (with English translation).
Communication dated Apr. 16, 2018 from the European Patent Office in counterpart European application No. 04752603.3.
Communication dated Apr. 28, 2017 issued by the European Patent Office in counterpart application No. 16196023.2.
Communication dated Jan. 26, 2017, from the European Patent Office in counterpart European application No. 16196023.2.
Communication dated May 8, 2017, from the European Patent Office in counterpart European Application No. 04752714.8.
Dottori et al., "Echocardiographic imaging of the Alfieri type mitral valve repair," Ital. Heart J., 2(4):319-320 (2001).
Downing et al., "Beating heart mitral valve surgery: Preliminary model and methodology," Journal of Thoracic and Cardiovascular Surgery, 123(6):1141-1146 (2002).
Extended European Search Report, dated Oct. 17, 2014, issued in European Patent Application No. 06751584.1.
Falk et al., "Computer-Enhanced Mitral Valve Surgery: Toward a Total Endoscopic Procedure," Seminars in Thoracic and Cardiovascular Surgery, 11(3):244-249 (1999).
Filsoufi et al., "Restoring Optimal Surface of Coaptation With a Mini Leaflet Prosthesis: A New Surgical Concept for the Correction of Mitral Valve Prolapse," Intl. Soc. for Minimally Invasive Cardiothoracic Surgery 1(4):186-87 (2006).
Frazier et al., "Early Clinical Experience with an Implantable, Intracardiac Circulatory Support Device: Operative Considerations and Physiologic Implications," http://www.sts.org/doc/7007 accessed on Sep. 24, 2008.
Fundaro et al., "Chordal Plication and Free Edge Remodeling for Mitral Anterior Leaflet Prolapse Repair: 8-Year Follow-up," Annals of Thoracic Surgery, 72:1515-1519 (2001).
Garcia-Rinaldi et al., "Left Ventricular Volume Reduction and Reconstruction is Ischemic Cardiomyopathy," Journal of Cardiac Surgery, 14:199-210 (1999).
Gateliene et al., "Early and late postoperative results of mitral and tricuspid valve insufficiency surgical treatment using edge-to-edge central coaptation procedure," Medicina (Kaunas) 38(Suppl. 2):172-175 (2002).
Gatti et al., "The edge to edge technique as a trick to rescue an imperfect mitral valve repair," Eur. J. Cardiothorac Surg, 22:817-820 (2002).
Gillinov et al., "Is Minimally Invasive Heart Valve Surgery a Paradigm for the Future?" Current Cardiology Reports, 1:318-322 (1999).
Gundry et al., "Facile Mitral Valve Repair Utilizing Leaflet Edge Approximation: Midterm Results of the Alfieri Figure of Eight Repair," The Western Thoracic Surgical Association, Scientific Session (May 1999).
Gupta et al., "Influence of Older Donor Grafts on Heart Transplant Survival: Lack of Recipient Effects," http://www.sts.org/doc/7007 accessed on Sep. 24, 2008.
Ikeda et al., "Batista's Operation with Coronary Artery Bypass Grafting and Mitral Valve Plasty for Ischemic Dilated Cardiomyopathy," The Japanese Journal of Thoracic and Cardiovascular Surgery, 48:746-749 (2000).
International Search Report and Written Opinion of PCT Application No. PCT/US2009/068023, dated Mar. 2, 2010, 10 pages total.
Izzat et al., "Early Experience with Partial Left Ventriculectomy in the Asia-Pacific Region," Annals of Thoracic Surgery, 67:1703-1707 (1999).
Kallner et al., "Transaortic Approach for the Alfieri Stitch," Ann Thorac Surg, 71:378-380 (2001).
Kavarana et al., "Transaortic Repair of Mitral Regurgitation," The Heart Surgery Forum, #2000-2389, 3(1):24-28 (2000).
Kaza et al., "Ventricular Reconstruction Results in Improved Left Ventricular Function and Amelioration of Mitral Insufficiency," Annals of Surgery, 235(6):828-832 (2002).
Kherani et al., "The Edge-to-Edge Mitral Valve Repair: The Columbia Presbyterian Experience," Ann. Thorac. Surg., 78:73-76 (2004).

Konertz et al., "Results After Partial Left Ventriculectomy in a European Heart Failure Population," Journal of Cardiac Surgery, 14:129-135 (1999).
Kron et al., "Surgical Relocation of the Posterior Papillary Muscle in Chronic Ischemic Mitral Regurgitation," Annals. of Thoracic Surgery, 74:600-601 (2002).
Kruger et al., "P73—Edge to Edge Technique in Complex Mitral Valve Repair," Thorac Cardiovasc Surg., 48(Suppl. 1):106 (2000).
Langer et al., "Posterier mitral leaflet extensions: An adjunctive repair option for ischemic mitral regurgitation?" J Thorac Cardiovasc Surg, 131:868-877 (2006).
Lorusso et al., "'Double-Orifice' Technique to Repair Extensive Mitral Valve Excision Following Acute Endocarditis," J. Card Surg, 13:24-26 (1998).
Lorusso et al., "The double-orifice technique for mitral valve reconstruction: predictors of postoperative outcome," Eur J. Cardiothorac Surg, 20:583-589 (2001).
Maisano et al., "The Double Orifice Repair for Barlow Disease: A Simple Solution for Complex Repair," Circulation 100(18):I-94 (1999).
Maisano et al., "The double orifice technique as a standardized approach to treat mitral regurgitation due to severe myxomatous disease: surgical technique," European Journal of Cardio-thoracic Surgery, 17:201-205 (2000).
Maisano et al., "The hemodynamic effects of double-orifice valve repair for mitral regurgitation: a 3D computational model," European Journal of Cardio-thoracic Surgery, 15:419-425 (1999).
Maisano et al., "Valve repair for traumatic tricuspid regurgitation," Eur. J. Cardio-thorac Surg, 10:867-873 (1996).
Mantovani et al., "Edge-to-edge Repair of Congenital Familiar Tricuspid Regurgitation: Case Report," J. Heart Valve Dis., 9:641-643 (2000).
McCarthy et al., "Partial left ventriculectomy and mitral valve repair for end-stage congestive heart failure," European Journal of Cardio-thoracic Surgery, 13:337-343 (1998).
Moainie et al., "Correction of Traumatic Tricuspid Regurgitation Using the Double Orifice Technique," Annals of Thoracic Surgery, 73:963-965 (2002).
Morales et al., "Development of an Off Bypass Mitral Valve Repair," The Heart Surgery Forum #1999-4693, 2(2):115-120 (1999).
Nakanishi et al., "Early Outcome with the Alfieri Mitral Valve Repair," J. Cardiol., 37:263-266 (2001) [Abstract in English; Article in Japanese].
Nielsen et al., "Edge-to-Edge Mitral Repair: Tension of the Approximating Suture and Leaflet Deformation During Acute Ischemic Mitral Regurgitation in the Ovine Heart," Circulation, 104(Suppl. I):I-29-I-35 (2001).
Noera et al., "Tricuspid Valve Incompetence Caused by Nonpenetrating Thoracic Trauma", Annals of Thoracic Surgery, 51:320-322 (1991).
Osawa et al., "Partial Left Ventriculectomy in a 3-Year Old Boy with Dilated Cardiomyopathy," Japanese Journal of Thoracic and Cardiovascular Surg, 48:590-593 (2000).
Patel et al., "Epicardial Atrial Defibrillation: Novel Treatment of Postoperative Atrial Fibrillation," http://www.sts.org/doc/7007 accessed on Sep. 23, 2008.
Privitera et al., "Alfieri Mitral Valve Repair: Clinical Outcome and Pathology," Circulation, 106:e173-e174 (2002).
Redaelli et al., "A Computational Study of the Hemodynamics After 'Edge-to-Edge' Mitral Valve Repair," Journal of Biomechanical Engineering, 123:565-570 (2001).
Reul et al., "Mitral Valve Reconstruction for Mitral Insufficiency," Progress in Cardiovascular Diseases, XXXIX(6):567-599 (1997).
Robicsek et al., "The Bicuspid Aortic Valve. How Does It Function? Why Does It Fail," http://www.sts.org/doc/7007 accessed on Sep. 24, 2008.
Supplemental European Search Report of EP Application No. 02746781, dated May 13, 2008, 3 pages total.
Supplementary European Search Report issued in European Application No. 05753261.6 dated Jun. 9, 2011, 3 pages total.

(56) References Cited

OTHER PUBLICATIONS

Tamura et al., "Edge to Edge Repair for Mitral Regurgitation in a Patient with Chronic Hemodialysis: Report of A Case," Kyobu Geka. The Japanese Journal of Thoracic Surgery, 54(9):788-790 (2001).

Tibayan et al., "Annular Geometric Remodeling in Chronic Ischemic Mitral Regurgitation," http://www.sts.org/doc/7007 accessed on Sep. 24, 2008.

Timek et al., "Edge-to-edge mitral repair: gradients and three-dimensional annular dynamics in vivo during inotropic stimulation," Eur J. of Cardiothoracic Surg., 19:431-437 (2001).

Timek, "Edge-to-Edge Mitral Valve Repair without Annuloplasty Ring in Acute Ischemic Mitral Regurgitation," [Abstract] Clinical Science, Abstracts from Scientific Sessions, 106(19):2281 (2002).

Totaro, "Mitral valve repair for isolated prolapse of the anterior leaflet: an 11-year follow-up," European Journal of Cardio-thoracic Surgery, 15:119-126 (1999).

Umana et al., "'Bow-tie' Mitral Valve Repair Successfully Addresses Subvalvular Dysfunction in Ischemic Mitral Regurgitation," Surgical Forum, XLVIII:279-280 (1997).

Votta et al., "3-D Computational Analysis of the Stress Distribution on the Leaflets after Edge-to-Edge Repair of Mitral Regurgitation," Journal of Heart Valve Disease, 11:810-822 (2002).

"Diving watch", Sep. 25, 2014, Retrieved from https://en.wikipedia.org w/index.php?title=Diving_watch&oldid=627082924, Retrieved on Apr. 28, 2016, Chapter: Elapsed time controller pp. 1-13.

"FDA premarket approval—MitraClip Clip delivery system", Oct. 24, 2013, Retrieved from http://www.accessdata.fda.gov/cdrh_docs/pdfl 0/pl 00009a .pdf, Retrieved on Apr. 28, 2016, pp. 1-5.

Leitgeb, "Safety of Electromedical Devices: Law-Risks—Opportunities," May 6, 2010, Springer Science & Business Media ISBN: 978-3-21 1-99682-9, Retrieved from https://books .google.de, Retrieved on Apr. 28, 2016, pp. 66.

"MitraClip Clip Delivery System IFU Instructions for Use MitraClip System Steerable Guide Catheter Ref No. SGC01 ST Clip Delivery System Ref No. CDS02ST MitraClip System Accessories Stabilizer Ref No. SZR01 ST Lift Ref No. LFT01 ST Support Plate Ref No. PLT01ST," Jan. 24, 2014, Retrieved from http://web.archive.org/web/*/http://www.fda.gov/downloads/AdvisoryCommittees/CommitteesMeetingMaterials/MedicalDevices/MedicalDevicesAdvisoryCommittee/CirculatorySystemDevicesPanel/UCM343688.pdf, Retrieved on Apr. 28, 2016, pp. 1-39.

Extended European Search Report dated Oct. 2, 2020 in Application No. EP 20174940.

\* cited by examiner

DELIVERY CATHETER HANDLE AND METHODS OF USE

CROSS-REFERENCE TO RELATED APPLICATIONS

This application is a continuation of U.S. patent application Ser. No. 14/879,726, filed Oct. 9, 2015, now U.S. Pat. No. 10,238,495, which is incorporated herein by this reference.

BACKGROUND

1. The Field of the Disclosure

The present disclosure relates generally to medical methods, devices, and systems. In particular, the present disclosure relates to methods, devices, and systems for the endovascular or minimally invasive surgical repair of the atrioventricular valves of the heart, particularly the mitral valve.

2. The Relevant Technology

Mitral valve regurgitation is characterized by retrograde flow from the left ventricle of a heart through an incompetent mitral valve into the left atrium. During a normal cycle of heart contraction (systole), the mitral valve acts as a check valve to prevent flow of oxygenated blood back into the left atrium. In this way, the oxygenated blood is pumped into the aorta through the aortic valve. Regurgitation of the valve can significantly decrease the pumping efficiency of the heart, placing the patient at risk of severe, progressive heart failure.

Mitral valve regurgitation can result from a number of different mechanical defects in the mitral valve. The valve leaflets, the valve chordae which connect the leaflets to the papillary muscles, or the papillary muscles themselves may be damaged or otherwise dysfunctional. Commonly, the valve annulus may be damaged, dilated, or weakened limiting the ability of the mitral valve to close adequately against the high pressures of the left ventricle.

The most common treatments for mitral valve regurgitation rely on valve replacement or strengthening of the valve annulus by implanting a mechanical support ring or other structure. The latter is generally referred to as valve annuloplasty. A recent technique for mitral valve repair which relies on suturing adjacent segments of the opposed valve leaflets together is referred to as the "bow-tie" or "edge-to-edge" technique. While all these techniques can be very effective, they usually rely on open heart surgery where the patient's chest is opened, typically via a sternotomy, and the patient placed on cardiopulmonary bypass. The need to both open the chest and place the patient on bypass is traumatic and has associated morbidity.

For these reasons, it would be desirable to provide alternative and additional methods, devices, and systems for performing the repair of mitral and other cardiac valves, particularly the tricuspid valve which is the other atrioventricular valve. Such methods, devices, and systems should preferably not require open chest access and be capable of being performed endovascularly, i.e., using devices which are advanced to the heart from a point in the patient's vasculature remote from the heart. Still more preferably, the methods, devices, and systems should not require that the heart be bypassed, although the methods, devices, and systems should be useful with patients who are bypassed and/or whose heart may be temporarily stopped by drugs or other techniques. At least some of these objectives will be met by the inventions described hereinbelow.

BRIEF SUMMARY

Certain embodiments of the present disclosure relate to a medical delivery assembly, including: a housing; a delivery device disposed at least partially within the housing; a lock configured to releasably secure the delivery device relative to the housing when in a locked configuration, and to allow translation of the delivery device within the housing when in an unlocked configuration; a lock actuator configured to engage with the lock to move the lock from the locked configuration toward the unlocked configuration; and a handle coupled to the lock actuator, the handle being configured to move the lock actuator to engage with the lock upon the handle being moved from a default position toward a depressed position.

Certain embodiments relate to a delivery system including: a housing; a delivery device disposed at least partially within the housing; a lock configured to releasably secure the delivery device relative to the housing when in a locked configuration, and to allow translation of the delivery device within the housing when in an unlocked configuration; a lock actuator configured to engage with the lock to move the lock from the locked configuration toward the unlocked configuration; and a handle coupled to the lock actuator, the handle being configured to move the lock actuator to engage with the lock upon the handle being moved from a default position toward a depressed position; a sleeve having a proximal end coupled to the housing; and a catheter having a proximal end coupled to the delivery device, the catheter extending distally from the delivery device through a lumen of the sleeve; wherein depression of the handle allows the delivery device to be translated within the housing so as to translate the catheter within the sleeve.

Certain embodiments of the present disclosure relate to a medical delivery system, including: a delivery assembly having a housing, a delivery device disposed at least partially within the housing, a lock configured to releasably secure the delivery device relative to the housing when in a locked configuration, and to allow translation of the delivery device within the housing when in an unlocked configuration, a lock actuator configured to engage with the lock to move the lock from the locked configuration toward the unlocked configuration, and a handle coupled to the lock actuator, the handle being configured to move the lock actuator to engage with the lock upon the handle being moved from a default position toward a depressed position; a sleeve having a proximal end coupled to the housing; and a catheter having a proximal end coupled to the delivery device, the catheter extending distally from the delivery device through a lumen of the sleeve; wherein depression of the handle allows the delivery device to be translated within the housing so as to translate the catheter within the sleeve.

Certain embodiments relate to a method of positioning a catheter at a target area, the method including: positioning a distal end of a sleeve at a target area, the sleeve having a proximal end coupled to a delivery assembly, the delivery assembly including a housing coupled to the sleeve, a delivery device disposed at least partially within the housing, a lock configured to releasably secure the delivery device relative to the housing when in a locked configuration, and to allow translation of the delivery device within the housing when in an unlocked configuration, a lock actuator configured to engage with the lock to move the lock from the locked configuration toward the unlocked configuration, and a handle coupled to the lock actuator, the handle being configured to move the lock actuator to engage with the lock upon the handle being moved from a default position toward a depressed position; depressing the handle to allow the delivery device to be translated within the housing; and translating the delivery device within the housing so as to translate the catheter within the sleeve.

Certain embodiments relate to a deployment handle for staged deployment of an implantable device from a delivery device, the deployment handle including: a lock cap removably attached to a housing lid; a lock line assembly configured to lock the implantable device by moving from an unlocked position toward a locked position, the lock line assembly including a lock tab configured to lodge within a lock slot disposed on the housing lid so as to hold the lock line assembly in the unlocked position; and an actuator handle at least partially enclosed by the lock cap, the actuator handle being configured to provide decoupling of the implantable device from the delivery device upon actuation of the actuator handle; wherein the lock cap is configured to prevent access to the actuator handle prior to removal, and is configured to engage with the lock tab upon removal of the lock cap so as to dislodge the lock tab to allow the lock line assembly to move toward the locked position.

Certain embodiments are directed to a delivery system for staged deployment of an implantable device at a target area, the delivery system including: a delivery catheter having a proximal end and a distal end; an adjustable implantable device coupled to the distal end of the delivery catheter; and a delivery device coupled to the proximal end of the delivery catheter, the delivery device including a deployment handle and one or more lock lines extending from the deployment handle through the catheter to the implantable device, the one or more lock lines being configured to engage with the implantable device to allow locking of the implantable device, the deployment handle including: a lock cap removably attached to a housing lid; a lock line assembly coupled to the one or more lock lines and configured to lock the implantable device by moving from an unlocked position toward a locked position, the lock line assembly including a lock tab configured to lodge within a lock slot disposed on the housing lid so as to hold the lock line assembly in the unlocked position; and an actuator handle at least partially enclosed by the lock cap, the actuator handle being configured to provide decoupling of the implantable device from the delivery device upon actuation of the actuator handle; wherein the lock cap is configured to prevent access to the actuator handle prior to removal, and is configured to engage with the lock tab upon removal of the lock cap so as to dislodge the lock tab to allow the lock line assembly to move toward the locked position to lock the implantable device.

Certain embodiments relate to a delivery system for staged deployment of an implantable device at a target area, the delivery system including: a catheter having a proximal end and a distal end; an adjustable implantation device coupled to the distal end of the catheter; and a delivery device coupled to the proximal end of the catheter, the delivery device including a deployment handle and one or more lock lines extending from the deployment handle through the catheter to the implantation device, the one or more lock lines being configured to engage with the implantation device to allow locking of the implantation device, the deployment handle including a lock cap removably attached to a housing lid, a lock line assembly coupled to the one or more lock lines and configured to lock the implantation device by moving from an unlocked position toward a locked position, the lock line assembly including a lock tab configured to lodge within a lock slot disposed on the housing lid so as to hold the lock line assembly in the unlocked position, and an actuator handle at least partially enclosed by the lock cap, the actuator handle being configured to provide decoupling of the implantation device from the delivery device upon actuation of the actuator handle; wherein the lock cap is configured to prevent access to the actuator handle prior to removal, and is configured to engage with the lock tab upon removal of the lock cap so as to dislodge the lock tab to allow the lock line assembly to move toward the locked position to lock the implantation device.

Certain embodiments relate to a method of deploying an implantation device at a target area, the method including: positioning the implantation device at a target area, the implantation device being coupled to a distal end of a delivery catheter and a deployment handle being coupled to a proximal end of the delivery catheter, wherein one or more lock lines extend from the deployment handle through the catheter to engage with the implantation device such that application or release of tension in the one or more lock lines provides locking of the implantation device, the deployment handle including a lock cap removably attached to a housing lid, a lock line assembly coupled to the one or more lock lines and configured to apply or release tension in the one or more lock lines by moving from an unlocked position toward a locked position, the lock line assembly including a lock tab configured to lodge within a slot disposed on the housing lid so as to hold the lock line assembly in the unlocked position, and an actuator handle at least partially enclosed by the lock cap, the actuator handle being configured to provide decoupling of the implantation device from the delivery catheter upon actuation of the actuator handle, wherein the lock cap is configured to prevent access to the actuator handle prior to removal, and is configured to engage with the lock tab upon removal of the lock cap so as to dislodge the lock tab to allow the lock line assembly to move toward the locked position; orienting the implantation device in a desired configuration; and removing the lock cap to lock the implantation device.

Certain embodiments relate to a control line assembly for use with a medical delivery device, the control line assembly including: a shuttle slidably disposed within a shaft; a collar configured to be translatable along the shaft, the collar configured to engage with the shuttle upon translation of the collar such that translation of the collar along the shaft causes translation of the shuttle within the shaft; and a hub coupled to the shuttle and configured to receive and secure one or more control lines extending distally from the hub such that translation of the shuttle within the shaft applies or releases tension in the one or more control lines.

Certain embodiments are directed to a medical device delivery system, including: a delivery device, the delivery device including a control line assembly, a catheter, and one or more control lines extending from the control line assembly through the catheter, the control line assembly including: a shuttle slidably disposed within a shaft; a hub coupled to the shuttle and configured to receive and secure the one or more control lines; and a collar configured to be translatable along the shaft, the collar configured to engage with the shuttle upon translation of the collar such that translation of the collar along the shaft causes translation of the shuttle within the shaft so as to apply or release tension in the one or more control lines; and an implantable device attached to a distal end of the catheter, the one or more control lines extending through the catheter and engaging with the implantable device such that translation of the collar adjusts the implantable device.

Certain embodiments relate to a medical device delivery system, including: a delivery device, the delivery device including a control line assembly, a catheter, and one or more control lines extending from the control line assembly through the catheter, the control line assembly including a shuttle slidably disposed within a shaft, a hub coupled to the shuttle and configured to receive and secure the one or more control lines, and a collar configured to be translatable along the shaft, the collar configured to engage with the shuttle upon translation of the collar such that translation of the collar along the shaft causes translation of the shuttle within the shaft so as to apply or release tension in the one or more control lines; and an implantable device attached to a distal end of the catheter, the one or more control lines extending through the catheter and engaging with the implantable device such that translation of the collar adjusts the implantable device.

Certain embodiments relate to a method of actuating an implantable device at a target area, the method including: positioning an implantable device at a target area, the implantable device being coupled to a distal end of a delivery catheter and a control line assembly being coupled to a proximal end of the delivery catheter, wherein one or more control lines extend from the control line assembly through the catheter to engage with the implantable device such that application or release of tension in the one or more control lines actuates the implantable device, the control line assembly including a shuttle slidably disposed within a shaft, a hub coupled to the shuttle and configured to receive and secure the one or more control lines, and a collar configured to be translatable along the shaft, the collar configured to engage with the shuttle upon translation of the collar such that translation of the collar along the shaft causes translation of the shuttle within the shaft so as to apply or release tension in the one or more control lines; and actuating the implantable device by translating the collar along the shaft.

Certain embodiments relate to a control line assembly for use with a medical delivery device, the control line assembly including: a carriage slidably disposed within a shaft; a hub coupled to the carriage and configured to receive and secure one or more control lines extending distally from the carriage such that translation of the carriage within the shaft applies or releases tension in the one or more control lines; a housing lid disposed on a proximal side of the carriage; and a lock tab extending from the carriage toward the housing lid, the housing lid including a slot configured in size and shape to allow passage of the lock tab through the slot and to allow the lock tab to be lodged in the slot so as to restrict translation of the carriage within the shaft.

Certain embodiments are directed to a medical device delivery system, including: a delivery device, the delivery device including a control line assembly, a catheter, and one or more control lines extending from the control line assembly through the catheter, the control line assembly including: a carriage slidably disposed within a shaft; a hub coupled to the carriage and configured to receive and secure the one or more control lines such that translation of the carriage within the shaft applies or releases tension in the one or more control lines; a housing lid disposed on a proximal side of the carriage; and a lock tab extending from the carriage toward the housing lid, the housing lid including a slot configured in size and shape to allow passage of the lock tab through the slot and to allow the lock tab to be lodged in the slot so as to restrict translation of the carriage within the shaft; and an implantable device attached to a distal end of the catheter, the one or more control lines extending through the catheter to the implantable device to provide control of the implantable device, wherein lodging of the lock tab within the slot restricts actuation of the implantable device.

Certain embodiments relate to a medical device delivery system, including: a delivery device, the delivery device including a control line assembly, a catheter, and one or more control lines extending from the control line assembly through the catheter, the control line assembly including a carriage slidably disposed within a shaft, a hub coupled to the carriage and configured to receive and secure the one or more control lines such that translation of the carriage within the shaft applies or releases tension in the one or more control lines, a housing lid disposed on a proximal side of the carriage, and a lock tab extending from the carriage toward the housing lid, the housing lid including a slot configured in size and shape to allow passage of the lock tab through the slot and to allow the lock tab to be lodged in the slot so as to restrict translation of the carriage within the shaft; and an implantable device attached to a distal end of the catheter, the one or more control lines extending through the catheter to the implantable device to provide control of the implantable device, wherein lodging of the lock tab within the slot restricts actuation of the implantable device.

Certain embodiments relate to a method of locking an implantable device in a desired configuration at a target area, the method including: positioning an implantable device at a target area, the implantable device being coupled to a distal end of a delivery catheter and a control line assembly being coupled to a proximal end of the delivery catheter, wherein one or more control lines extend from the control line assembly through the catheter to engage with the implantable device such that application or release of tension in the one or more control lines actuates the implantable device, the control line assembly including a carriage slidably disposed within a shaft, a hub coupled to the carriage and configured to receive and secure the one or more control lines such that translation of the carriage within the shaft applies or releases tension in the one or more control lines, a housing lid disposed on a proximal side of the carriage, and a lock tab extending from the carriage toward the housing lid, the housing lid including a slot configured in size and shape to allow passage of the lock tab through the slot and to allow the lock tab to be lodged in the slot so as to restrict translation of the carriage within the shaft; orienting the implantable device in a desired configuration; and locking the implantable device by lodging the lock tab within the slot to prevent actuation of the implantable device.

Certain embodiments relate to a fluid management system for use with a medical delivery device, the fluid management system including: a flush body, the flush body including an opening, a catheter outlet, and a fluid inlet configured to receive a fluid into an interior space of the flush body; a grommet at least partially housed within the flush body, the grommet having an interior lumen and being configured to be in fluid communication with the interior space such that fluid can pass from the interior space into the interior lumen; and a conducting assembly disposed at the opening, the conducting assembly configured to receive one or more components of the delivery device and direct the one or more components into the interior lumen; wherein the grommet is configured to be couplable to a catheter extending through the catheter outlet so as to allow the catheter to receive the fluid and the one or more components from the interior lumen and transport the fluid and the one or more components through the catheter outlet.

Certain embodiments are directed to a medical device delivery system, including: a delivery device, the delivery device including a fluid management system and a delivery catheter coupled to the fluid management system, the fluid management system including: a flush body, the flush body including an opening, a catheter outlet, and a fluid inlet configured to receive a fluid into an interior space of the flush body; a grommet at least partially housed within the flush body, the grommet having an interior lumen and being configured to be in fluid communication with the interior space such that fluid can pass from the interior space into the interior lumen; and a conducting assembly disposed at the opening, the conducting assembly configured to receive one or more components of the delivery device and direct the one or more components into the interior lumen; wherein a proximal end of the delivery catheter is coupled to the grommet so as to allow the delivery catheter to receive the fluid and the one or more components from the interior lumen and transport the fluid and the one or more components through the catheter outlet; and an implantable device attached to a distal end of the delivery catheter, the delivery catheter being configured to transport the fluid and the one or more components from the fluid management system to the implantable device.

Certain embodiments relate to a medical device delivery system, including: a delivery device, the delivery device including a fluid management system and a delivery catheter coupled to the fluid management system, the fluid management system including a flush body, the flush body including an opening, a catheter outlet, and a fluid inlet configured to receive a fluid into an interior space of the flush body, a grommet at least partially housed within the flush body, the grommet having an interior lumen and being configured to be in fluid communication with the interior space such that fluid can pass from the interior space into the interior lumen, and a conducting assembly disposed at the opening, the conducting assembly configured to receive one or more components of the delivery device and direct the one or more components into the interior lumen, wherein a proximal end of the delivery catheter is coupled to the grommet so as to allow the delivery catheter to receive the fluid and the one or more components from the interior lumen and transport the fluid and the one or more components through the catheter outlet; and an implantable device attached to a distal end of the delivery catheter, the delivery catheter being configured to transport the fluid and the one or more components from the fluid management system to the implantable device.

Certain embodiments relate to a method of directing fluid in a medical delivery device, the method including: injecting a fluid into the medical delivery device, the medical delivery device including a fluid management system and a catheter coupled to the fluid management system, the fluid management system including a flush body, the flush body including an opening, a catheter outlet, and a fluid inlet configured to receive a fluid into an interior space of the flush body, a grommet at least partially housed within the flush body, the grommet having an interior lumen and being configured to be in fluid communication with the interior space such that fluid can pass from the interior space into the interior lumen, a conducting assembly disposed at the opening, the conducting assembly configured to receive one or more components of the delivery device and direct the one or more components into the interior lumen, wherein a proximal end of the catheter passes through the catheter outlet and is coupled to the grommet so as to allow the catheter to receive the fluid and the one or more components from the interior lumen; and transporting the fluid through the catheter to an implantable device at a distal end of the catheter.

BRIEF DESCRIPTION OF THE DRAWINGS

In order to describe the manner in which the above-recited and other features of the disclosure can be obtained, a more particular description will be rendered by reference to specific embodiments thereof which are illustrated in the appended drawings. For better understanding, the like elements have been designated by like reference numbers throughout the various accompanying figures. While some of the drawings may be schematic or exaggerated representations of concepts, at least some of the drawings may be drawn to scale. Understanding that the drawings depict some example embodiments, the embodiments will be described and explained with additional specificity and detail through the use of the accompanying drawings in which.

DETAILED DESCRIPTION

I. Cardiac Physiology

Figure 1:
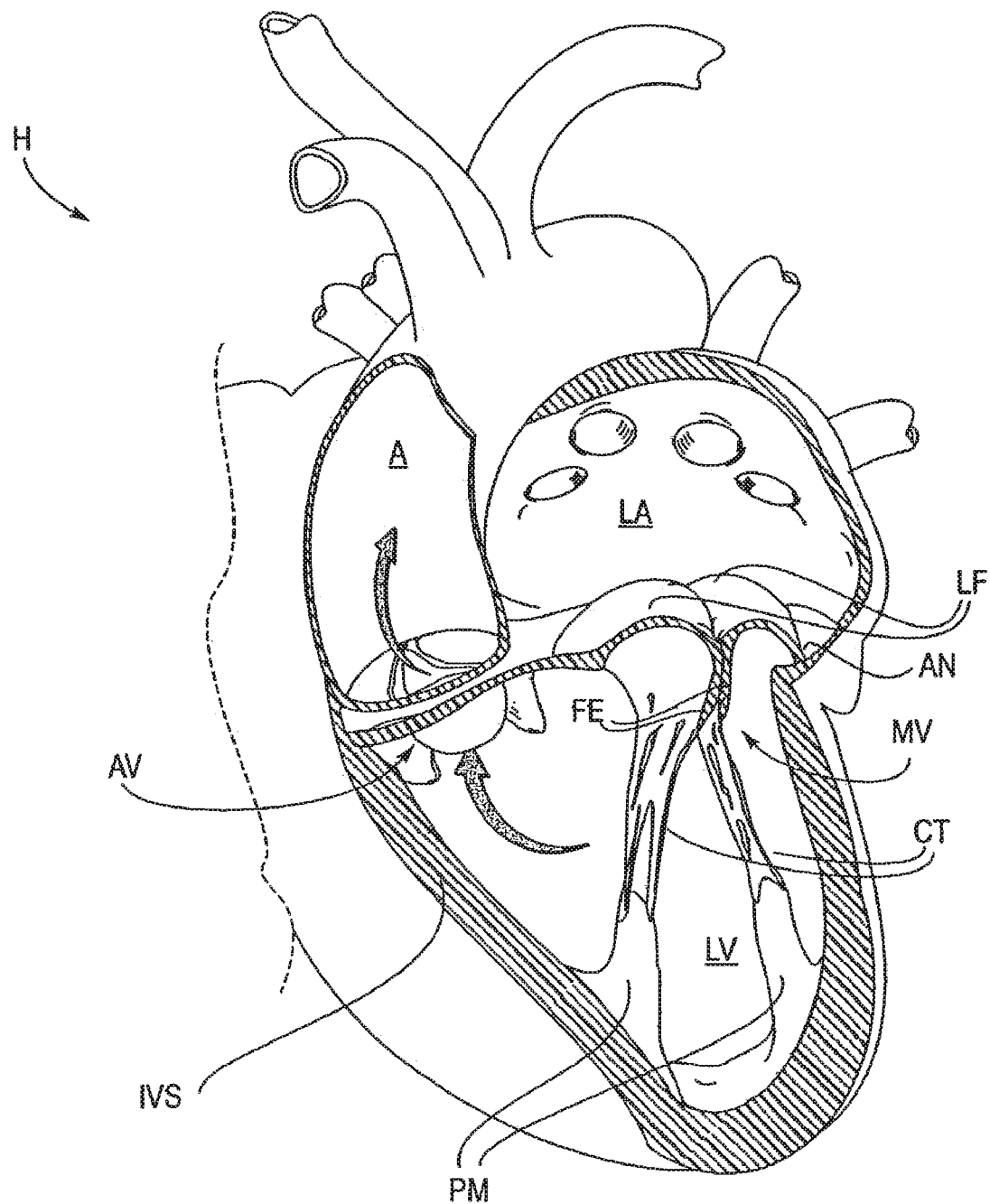
FIG. 1 illustrates cardiac physiology.

The left ventricle LV of a normal heart H in systole is illustrated in FIG. 1. The left ventricle LV is contracting and blood flows outwardly through the tricuspid (aortic) valve AV in the direction of the arrows. Back flow of blood or "regurgitation" through the mitral valve MV is prevented since the mitral valve is configured as a "check valve" which prevents back flow when pressure in the left ventricle is higher than that in the left atrium LA. The mitral valve MV comprises a pair of leaflets having free edges FE which meet evenly to close, as illustrated in FIG. 1. The opposite ends of the leaflets LF are attached to the surrounding heart structure along an annular region referred to as the annulus AN. The free edges FE of the leaflets LF are secured to the lower portions of the left ventricle LV through chordae tendinae CT (referred to hereinafter as the chordae) which include plurality of branching tendons secured over the lower surfaces of each of the valve leaflets LF. The chordae CT in turn, are attached to the papillary muscles PM which extend upwardly from the lower portions of the left ventricle and intraventricular septum IVS.

Figure 2:
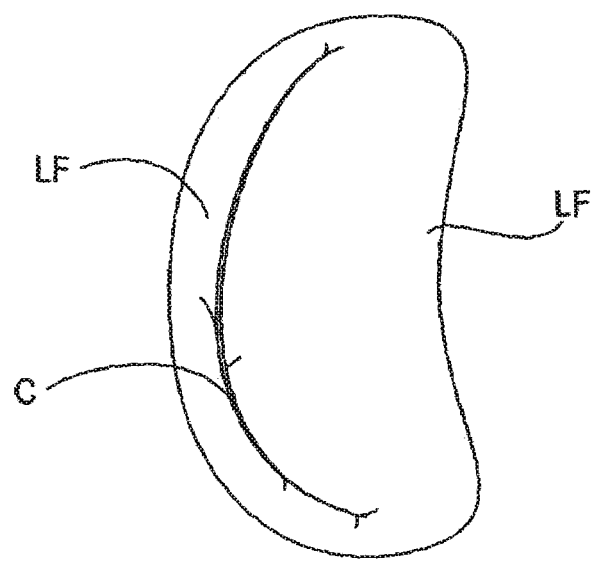
FIG. 2 illustrates free edges of leaflets in normal coaptation.
Figure 3:
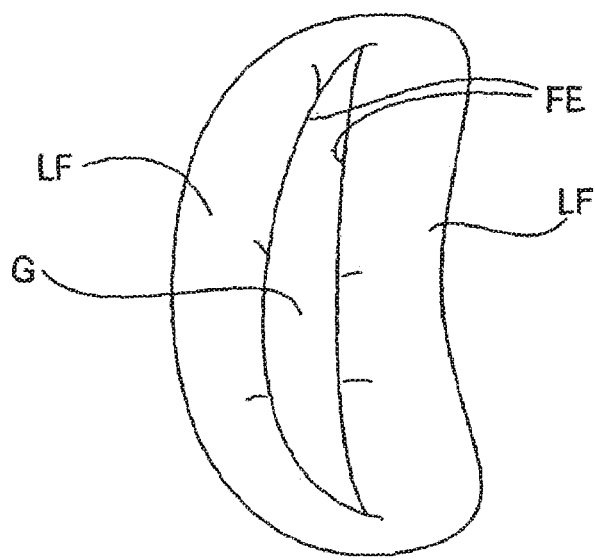
FIG. 3 illustrates the free edges in regurgitative coaptation.

A number of structural defects in the heart can cause mitral valve regurgitation. Regurgitation occurs when the valve leaflets do not close properly allowing leakage from the ventricle into the atrium. As shown in FIG. 2, the free edges of the anterior and posterior leaflets normally meet along a line of coaptation C. An example of a defect causing regurgitation is shown in FIG. 3. Here an enlargement of the heart causes the mitral annulus to become enlarged, making it impossible for the free edges FE to meet during systole. This results in a gap G which allows blood to leak through the valve during ventricular systole. Ruptured or elongated chordae can also cause a valve leaflet to prolapse since inadequate tension is transmitted to the leaflet via the chordae. While the other leaflet maintains a normal profile, the two valve leaflets do not properly meet and leakage from the left ventricle into the left atrium will occur. Such regurgitation can also occur in patients who have suffered ischemic heart disease where the left ventricle does not contract sufficiently to effect proper closure.

II. General Overview

The present disclosure provides methods and devices for grasping, approximating and fixating tissues, such as heart valve leaflets, to treat cardiac valve regurgitation, particularly mitral valve regurgitation. The present disclosure provides methods and devices for delivering an implantable device to a treatment area, such as delivering an implantable heart valve device (e.g., an implantable mitral valve device) to a target heart valve. These and other applications can include, for example, implant, repair, and/or fixation procedures related to functional mitral valve regurgitation or implant, repair, and/or fixation procedures related to the tricuspid valve, pulmonary valve, aortic valve, or other related heart tissues. The present disclosure also provides features that allow repositioning and removal of the implantable device if so desired, particularly in areas where removal may be hindered by anatomical features such as chordae CT. Such removal would allow the surgeon to reapproach the valve in a new manner if so desired.

Grasping can be atraumatic. By atraumatic, it is meant that the devices and methods of the invention may be applied to the valve leaflets and then removed without causing any significant clinical impairment of leaflet (or other tissue) structure or function. For example, the leaflets and valve of a treated mitral valve can continue to function substantially the same or better as before embodiments of the present disclosure have been applied. Thus, some minor penetration or denting of the leaflets may occur using embodiments of the present disclosure while still meeting the definition of "atraumatic." This enables the devices of the present disclosure to be applied to a diseased valve and, if desired, removed or repositioned without having negatively affected valve function. In addition, it will be understood that in some cases it may be necessary or desirable to pierce or otherwise permanently affect the leaflets during grasping, fixing, or both. In some of these cases, grasping and fixation may be accomplished by a single device.

The systems, devices and methods of the present disclosure rely upon the use of an interventional tool (which, in some embodiments, can also function as an implantable device) that is positioned near a desired treatment site and used to grasp the target tissue. In endovascular applications, the interventional tool is typically an interventional catheter. In surgical applications, the interventional tool is typically an interventional instrument. In some embodiments, fixation of the grasped tissue is accomplished by maintaining grasping with a portion of the interventional tool which is left behind as an implant. While embodiments of the disclosure may have a variety of applications for implantation, tissue approximation, and/or fixation throughout the body, it is particularly well adapted for the repair of valves, especially cardiac valves such as the mitral valve.

Figure 4:
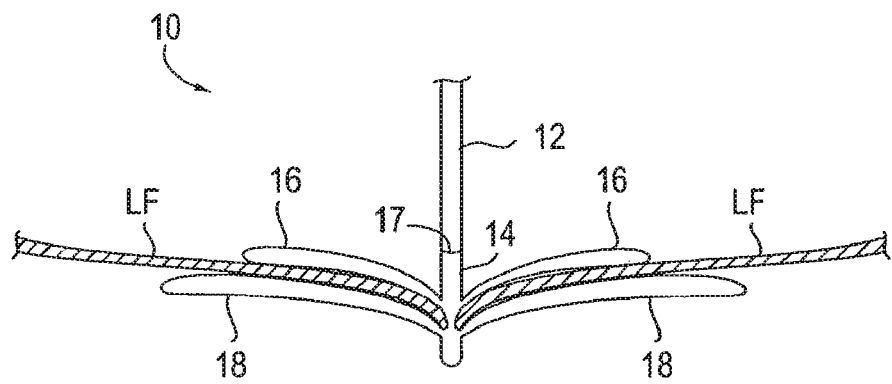
FIGS. 4-6 illustrate an embodiment of grasping heart valve leaflets using a fixation device.

Referring to FIG. 4, an interventional tool 10, having a delivery assembly, such as a shaft 12, and an implantable device 14, is illustrated having approached the mitral valve MV from the atrial side and grasped the leaflets LF. The mitral valve may be accessed either surgically or by using endovascular techniques, and/or either by a retrograde approach through the ventricle or by an antegrade approach through the atrium, as described above. For illustration purposes, an antegrade approach is described.

The implantable device 14 may be releasably attached to the shaft 12 of the interventional tool 10 at its distal end. When describing the devices of the present disclosure herein, "proximal" shall mean the direction toward the end of the device to be manipulated by an operator outside the patient's body, and "distal" shall mean the direction toward the working end of the device that is positioned at the treatment site and away from the operator. With respect to the mitral valve, proximal shall refer to the atrial or upstream side of the valve leaflets and distal shall refer to the ventricular or downstream side of the valve leaflets. As described herein, an implantable device, such as implantable device 14, may include an implantable device and/or a fixation device, such as a valve repair device (e.g., a MITRA-CLIP®), a valve replacement device, or another implantable device.

The implantable device 14 can include gripping elements 16 and distal elements 18 which can protrude radially outward and may be positionable on opposite sides of the leaflets LF as shown so as to be able to capture or retain the leaflets therebetween. The gripping elements 16 may be formed of cobalt chromium, a nickel-titanium alloy, or stainless steel, and the distal elements 18 may be formed of cobalt chromium or stainless steel; however, any suitable materials may be used (e.g., polymers, other metals, and/or biocompatible materials).

The gripping elements 16 may be formed as one integral piece, referred to herein as a "gripper." In other embodiments, the gripping elements may be separately formed and/or otherwise decoupled. The implantable device 14 may be coupleable to the shaft 12 by a coupling mechanism 17. The coupling mechanism 17 can allow the implantable device 14 to detach and be left behind as an implant to hold the leaflets together in the coapted position.

In some situations, it may be desired to reposition and/or remove the implantable device 14 after the gripper elements 16, distal elements 18, or both have been deployed to capture the leaflets LF. Such repositioning and/or removal may be desired for a variety of reasons, such as to reapproach the valve in an attempt to achieve better valve function, more optimal positioning of the device 14 on the leaflets, better purchase on the leaflets, to detangle the device 14 from surrounding tissue (such as chordae), to exchange the device 14 with one having a different design, and/or to abort the fixation procedure, for example.

Figure 5:
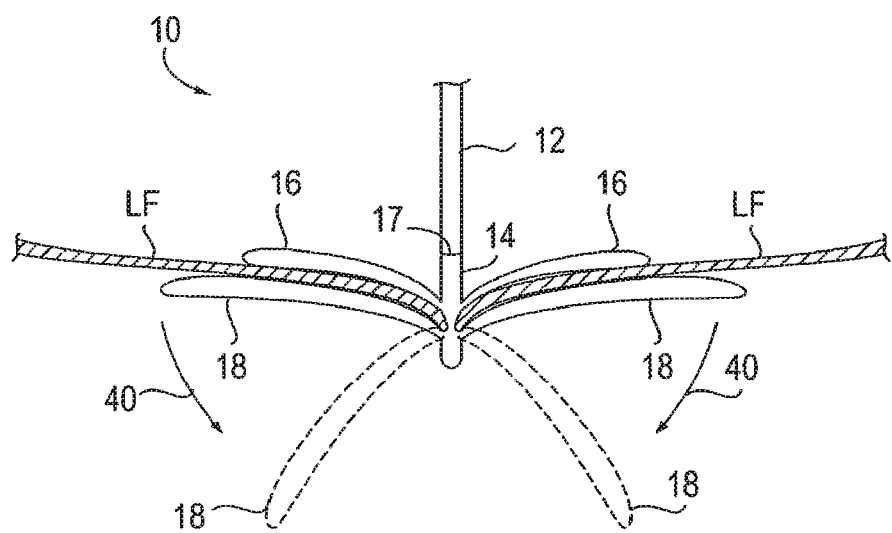
Figure 6:
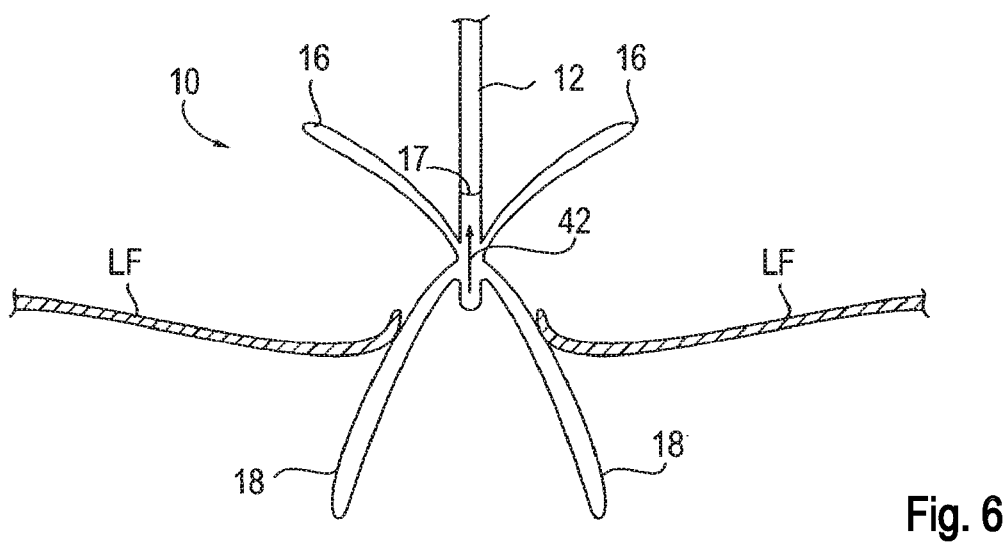

To facilitate repositioning or removal of the implantable device 14 the distal elements 18 can be releasable and optionally invertible to a configuration suitable for withdrawal of the device 14 from the valve without tangling, interfering with, and/or damaging the chordae, leaflets and/or other tissue. FIG. 5 illustrates inversion wherein the distal elements 18 are moveable in the direction of arrows 40 to an inverted position. The gripper elements 16 may be raised, if desired. In the inverted position, the device may be repositioned to a desired orientation wherein the distal elements 18 may then be reverted to a grasping position against the leaflets as in FIG. 4. Alternatively, the implantable device 14 may be withdrawn (indicated by arrow 42) from the target area as shown in FIG. 6. Such inversion can reduce trauma to the leaflets and can minimize any entanglement of the device with surrounding tissues. Once the implantable device 14 has been withdrawn through the valve leaflets, the gripper elements 16 and distal elements 18 may be moved to a closed position or configuration suitable for removal from the body or for reinsertion through the mitral valve.

Figure 7:
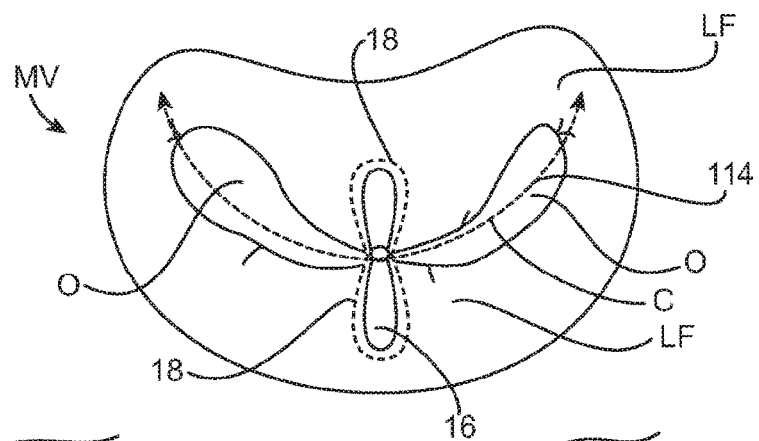
FIG. 7 illustrates a position of the fixation device in a desired orientation relative to the leaflets.

FIG. 7 illustrates the position of the implantable device 14 in one desired orientation in relation to the leaflets LF. This is a short-axis view of the mitral valve MV from the atrial side, therefore, the gripper elements 16 are shown in solid line and the distal elements 18 are hidden from view and shown in dashed line. As shown, the gripper elements 16 and distal elements 18 can be positioned to be substantially perpendicular to the line of coaptation C. The implantable device 14 may be moved roughly along the line of coaptation to the location of regurgitation. The leaflets LF can be held in place so that during diastole, as shown in FIG. 7, the leaflets LF remain in position between the gripper elements 16 and the distal elements 18 surrounded by openings O which result from the diastolic pressure gradient. Advantageously, leaflets LF can be coapted such that their proximal or upstream surfaces are facing each other in a vertical orientation, parallel to the direction of blood flow through mitral valve MV. The upstream surfaces may be brought together so as to be in contact with one another or may be held slightly apart, but will preferably be maintained in the vertical orientation in which the upstream surfaces face each other at the point of coaptation. This simulates the double orifice geometry of a standard surgical bow-tie repair.

Color Doppler echo can show if the regurgitation of the valve has been reduced. If the resulting mitral flow pattern is satisfactory, the leaflets may be fixed together in this orientation. If the resulting color Doppler image shows insufficient improvement in mitral regurgitation, the interventional tool 10 may be repositioned. This may be repeated until an optimal result is produced wherein the leaflets LF are held in place.

Once the leaflets are coapted in the desired arrangement, the implantable device 14 can be detached from the shaft 12 and left behind as an implant to hold the leaflets together in the coapted position. As mentioned previously, the implantable device 14 can be coupled to the shaft 12 by a coupling mechanism 17. FIGS. 8-11 illustrate exemplary embodiments of such coupling mechanisms.

Figure 8:
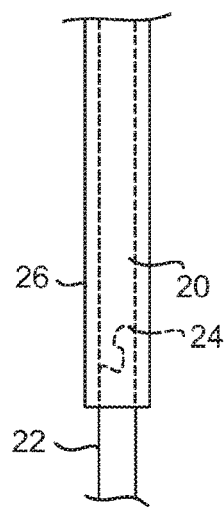
FIGS. 8-11 illustrate embodiments of a coupling mechanism configured to couple a fixation device to an actuator rod.
Figure 9:
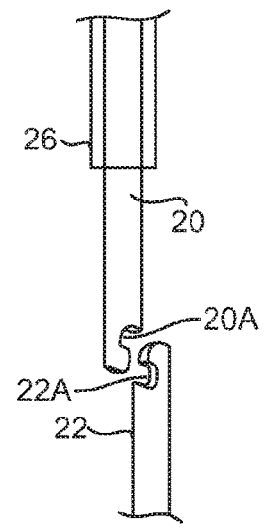

FIG. 8 shows an upper shaft 20 and a detachable lower shaft 22 which are interlocked at a joining line or mating surface 24. The mating surface 24 may have any shape or curvature which will allow or facilitate interlocking and later detachment. A snuggly fitting outer sheath 26 may be positioned over the upper shaft 20 and lower shaft 22 to cover the mating surface 24, as shown. FIG. 9 illustrates detachment of the lower shaft 22 from the upper shaft 20. This may be achieved by retracting the outer sheath 26, so that the mating surface 24 is exposed, which allows the upper shaft 20 and lower shaft 22 to separate.

Figure 10:
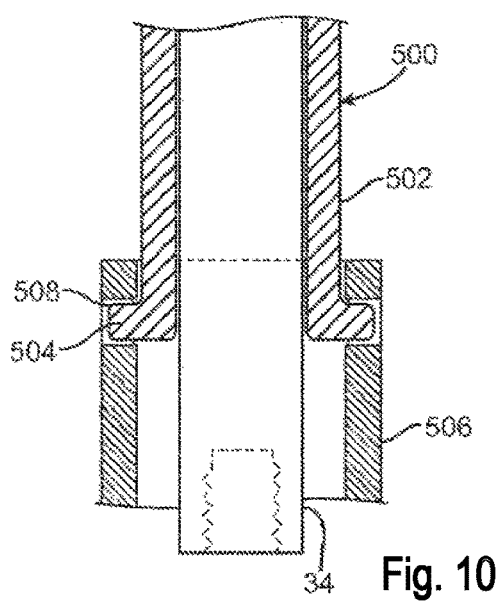
Figure 11:
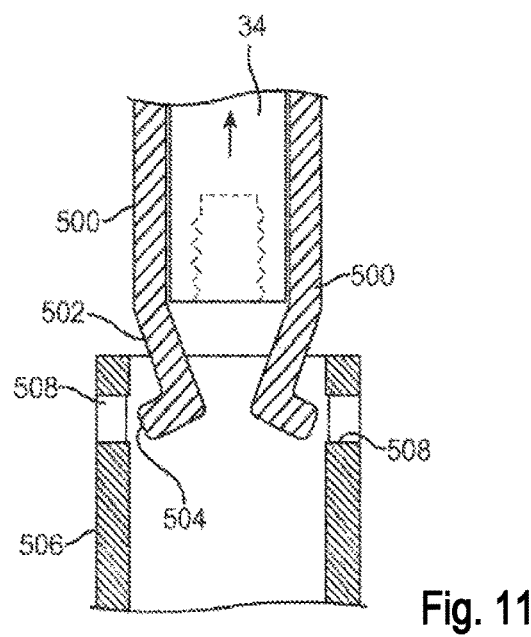

FIGS. 10-11 illustrate another exemplary coupling mechanism. Here, upper shaft 500 is releasably coupled with lower shaft 506 with a detent mechanism 504, 508. The upper and lower shafts in this embodiment are generally tubular shaped although one of skill in the art will appreciate that other configurations are possible. The detent mechanism includes one or more spring arms 502 integrally formed on tubular upper shaft 500 and one or more receptacles 508 sized to receive the spring arms 502. Tubular upper shaft 500 is integrally formed with one or more spring arms 502 having a flange-like engagement surface 504 at a distal end thereof. The spring arms 502 are preferably biased inwardly, i.e., toward the interior of the shaft 500. Detachable tubular lower shaft 506 features one or more receptacles, here apertures 508 configured to receive and mate with the engagement surface 504 of the spring arm 502. The apertures 508 may extend partially or all the way through the wall of the lower shaft 506. A snuggly fitting rod 34 or inner member is inserted through the tubular shafts 500, 506 outwardly deflecting the inwardly biased spring arm(s) 502 such that the engagement surface 504 is pushed into engagement with a corresponding receptacle 508 thereby preventing detachment of the upper shaft 500 from the lower shaft 506. In FIGS. 10-11, two spring arms 502 are illustrated; however, any number of spring arms may be used. Thus the invention should be understood to encompass an embodiment having a single spring arm 50 as well as an embodiment having three or more spring arms 502.

FIG. 11 illustrates detachment of the lower shaft 506 from the upper shaft 500. This is achieved by retracting the rod 34 to a position above the spring arm(s) 502 which allows the inwardly biased engagement surface 504 to disengage from the receptacle 508 allowing the shafts 500, 506 to separate. The embodiment illustrated in FIGS. 10 and 11 depicts the spring arms 502 on the upper shaft 500 and the receptacle 508 on the lower shaft 506. Though not illustrated, these features may be reversed with the spring arms 502 on the lower shaft 506 and the receptacle on the upper shaft 500. In addition, while the spring arms 502 can be biased inwardly as described, the spring arms 502 alternatively can be biased outwardly and application of a proximal force on the shaft 500 is sufficient to release the engagement surface 504 from the receptacle 508, optionally modified with curved or sloping interior corners to aid with disengagement. Other examples of coupling mechanisms are described and illustrated in U.S. Pat. No. 8,216,256, incorporated herein by reference for all purposes.

III. Implantable Device

A. Introduction and Placement of Implantable Device

The implantable device 14 may be delivered to the valve or other target tissue with the use of a medical delivery device configured to deliver an implantable device or other tissue treating device to a target area ("delivery device"). For endovascular applications, the delivery device can include a flexible delivery catheter which will be described in later sections. Such a catheter can include a shaft, having a proximal end and a distal end, and an implantable device releasably attached to the distal end. The shaft may be elongate and flexible, suitable for intravascular introduction. Alternatively, the delivery device may include a shorter and less flexible interventional instrument which may be used for trans-thoracic surgical introduction through the wall of the heart, for example. An implantable device may be releasably coupleable with the delivery device as illustrated in FIG. 4. The implantable device may have a variety of forms, a few embodiments of which will be described herein.

Figure 12:
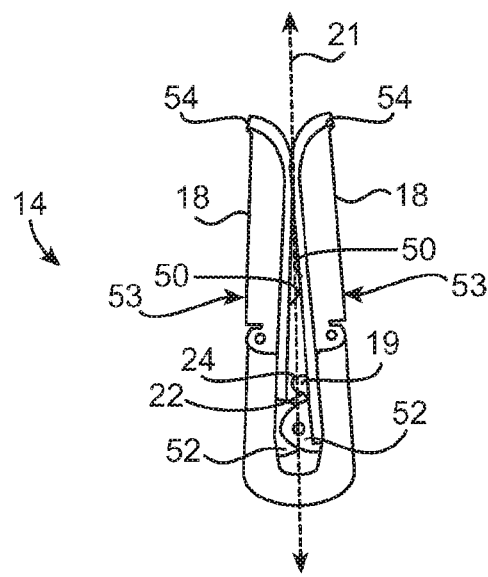
FIGS. 12-27 illustrate an embodiment of a fixation device in various positions.

FIGS. 12-15 illustrate an embodiment of an implantable device 14 in various positions or configurations. FIG. 12 illustrates the implantable device 14 in a closed configuration suitable for delivery through a patient's vasculature and, in this example, through the mitral valve. The implantable device 14 may include a coupling member 19 which allows detachment of the implantable device 14 for implantation. In this example, the coupling member 19 is shown to include the lower shaft 22 and mating surface 24 of FIGS. 8-9, and therefore the coupling member 19 can function similarly as described above. The implantable device 14 may also include a pair of opposed distal elements 18, each distal element 18 having an engagement surface 50 facing inwardly toward the opposed distal element 18 in the closed configuration.

Distal elements 18 may include elongate arms 53, each arm having a proximal end 52 rotatably connected to the coupling member 19, and a free end 54. Suitable connections for arms 53 to coupling member 19 include pins, living hinges, or other known rotational connection mechanisms. In the closed configuration of FIG. 12, free ends can 54 point in a first direction such that the arms 53 and engagement surfaces 50 are nearly parallel to each other and to an axis 21, and may be angled slightly inwardly toward each other. In some embodiments, when tissue is not present between arms 53, the arms 53 may be closed until free ends 54 either touch each other or engage shaft 12 when implantable device 14 is attached thereto, thereby minimizing the profile of the implantable device 14 (e.g., for passage through a delivery device).

Figure 13:
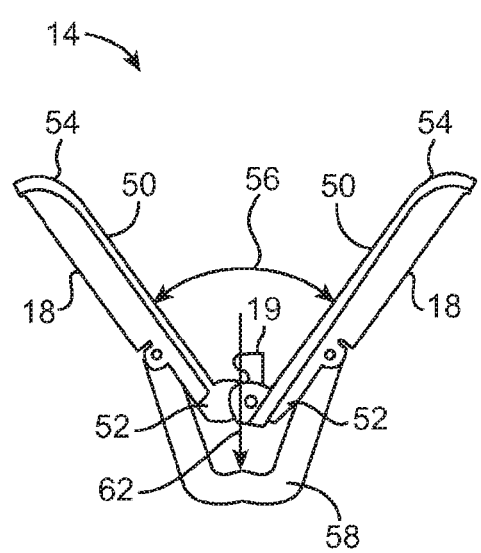
Figure 14:
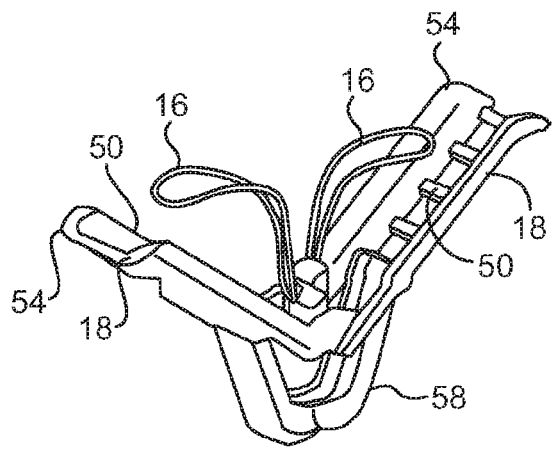

FIGS. 13-14 illustrate the implantable device 14 in an open position wherein the engagement surfaces 50 are disposed apart at a separation angle 56. The separation angle 56 may be up to approximately 180 degrees, such as up to 90-180 degrees, and arms 53 may be disposed generally symmetrically relative to axis 21. The arms 53 may be moveable to the open position by a variety of actuation mechanisms. For example, a plunger or actuator rod may be advanced through the coupling member 19, as indicated by arrow 62, so as to engage a spring or spring loaded actuation mechanism 58 which is attached to the distal elements 18. By exerting a force against the actuation mechanism 58, the distal elements 18 can be rotated relative to coupling member 19. The distal elements 18 may be held in this open position by the actuator rod against the resistance provided by the spring of the actuation mechanism 58, which biases the distal elements 18 toward the closed position of FIG. 12 when the distal elements 18 are less than 180 degrees apart. The spring loading of the actuation mechanism 58 can resist outward movement of the actuation mechanism 58 and/or can urge the device 14 towards the closed position.

In this embodiment, gripper elements 16 comprise resilient loop-shaped wire forms biased outwardly and attached to the coupling member 19 so as to be biased to an open position shown in FIG. 14, but moveable rotationally inwardly when arms 53 are closed. The wire forms may be flexible enough to be rigidly attached to coupling member 19 and resiliently deflectable inwardly, or they may be attached by a rotational coupling such as a pin or living hinge. In use, leaflets LF (or other tissue) are positioned between the gripper elements 16 and distal elements 18. Once the leaflets LF are positioned between the gripper elements 16 and distal elements 18, the distal elements 18 may be closed, compressing the leaflets between engagement surfaces 50 and gripper elements 16. Depending upon the thickness of the leaflets, the arrangements of the leaflets, the position of the implantable device on the leaflets, and other factors, the arms 53 may be maintained in the open position of FIG. 13, moved to the fully closed position of FIG. 12, or placed in any of various positions in between so as to coapt the leaflets LF and hold them in the desired position with the desired degree of force. In most cases, the implantable device 14 will remain in place as an implant following detachment from the delivery catheter.

In some situations, as described above, it may be desirable to reopen the implantable device 14 following initial placement. To reopen the device 14, the actuator rod may be readvanced or reinserted through the coupling member 19 and readvanced to press against the actuation mechanism 58, as previously indicated by arrow 62 in FIG. 13. Again, such advancement applies a force against the actuation mechanism 58 in the manner described above, thus moving arms 53 outwardly to release force against leaflets and move engagement surfaces 50 away from gripper elements 16. The leaflets are then free to move relative to implantable device 14. The implantable device 14 may then be repositioned as desired and the actuator rod retracted to reclose the distal elements 18 to coapt the leaflets.

Figure 15:
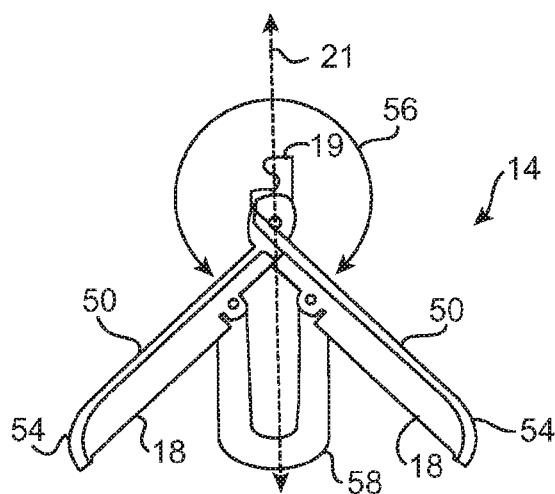

Under some circumstances, it may be desirable to withdraw the implantable device 14 back through the valve or completely from the patient following initial insertion through the valve. Should this be attempted with the clip in the closed or open positions illustrated in FIGS. 12-14, there may be a risk that arms 53 could interfere or become entangled with the chordae, leaflets or other tissues. To avoid this, the fixation element 14 may be adapted for inversion of arms 53 so that free ends 54 point in a second direction, opposite to the first direction in which the free ends 54 pointed in the closed position, each arm 53 forming an obtuse angle relative to axis 21 as illustrated in FIG. 15.

The arms 53 may be rotated so that the engagement surfaces 50 are disposed at a separation angle 56 of up to 360 degrees, or up to 270 degrees. This may be accomplished by exerting a force against actuation mechanism 58 with a push rod or plunger extending through coupling member 19 as described above. In this embodiment, once the distal elements 18 have rotated beyond 180 degrees apart, the spring loading of the actuation mechanism 58 can bias the distal elements 18 toward the inverted position. The spring loading of the actuation mechanism 58 can resist outward movement of the actuation mechanism 58 and can urge the device 14 towards the inverted position.

With arms 53 in the inverted position, engagement surfaces 50 can provide an atraumatic surface to deflect tissues as the implantable device is withdrawn. This allows the device to be retracted back through the valve annulus without risk of injury to valvular and other tissues. In some cases, once the implantable device 14 has been pulled back through the valve, it will be desirable to return the device to the closed position for withdrawal of the device from the body (either through the vasculature or through a surgical opening).

The embodiment illustrated in FIGS. 12-15 can be assembled from separate components composed of biocompatible materials. The components may be formed from the same or different materials, including but not limited to stainless steel or other metals, Elgiloy®, nickel-titanium alloy, titanium, tantalum, metal alloys, or polymers. Additionally, some or all of these components may be made of bioabsorbable materials that can be absorbed by surrounding tissues or can dissolve into the bloodstream following implantation. It has been found that in mitral valve repair applications the implantable devices of the present disclosure are completely surrounded by tissue within a few months of implantation, after which the devices could dissolve or be absorbed without negative impact to the repair.

Figure 16:
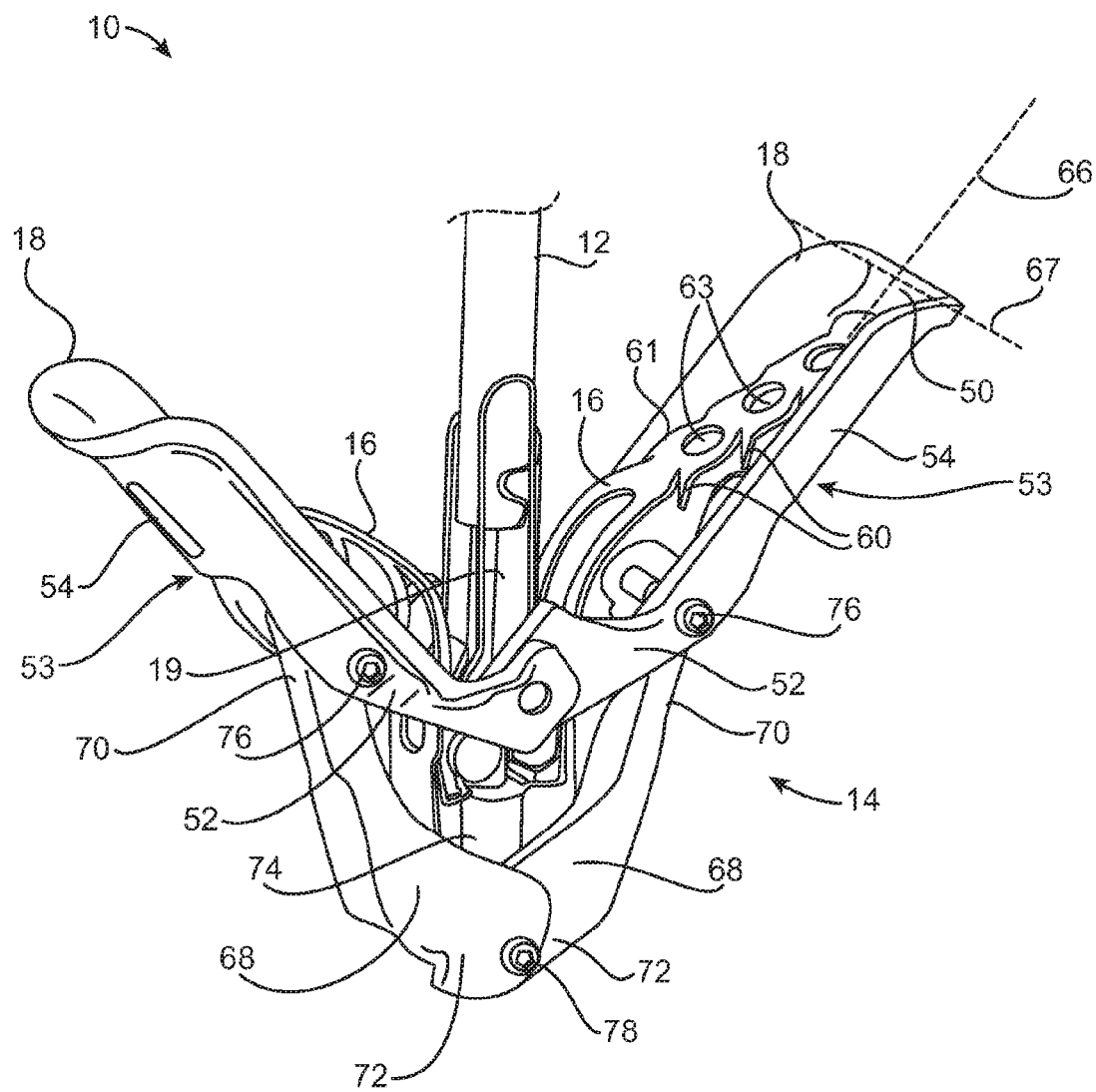

FIG. 16 illustrates an embodiment of an implantable device 14. Here, the implantable device 14 is shown coupled to a shaft 12 to form an interventional tool 10. The implantable device 14 may include a coupling member 19 and a pair of opposed distal elements 18. The distal elements 18 can comprise elongate arms 53, each arm having a proximal end 52 rotatably connected to the coupling member 19 and a free end 54. The free ends 54 can have a rounded shape to minimize interference with and trauma to surrounding tissue structures. In some embodiments, each free end 54 defines a curvature about two axes, one being an axis 66 perpendicular to longitudinal axis of arms 53. The engagement surfaces 50 can have a cupped or concave shape to surface area in contact with tissue and to assist in grasping and holding the valve leaflets. This further allows arms 53 to nest around the shaft 12 in the closed position to minimize the profile of the device.

In some embodiments, arms 53 are at least partially cupped or curved inwardly about their longitudinal axes 66. In some embodiments, each free end 54 defines a curvature about an axis 67 perpendicular to axis 66 or the longitudinal axis of arms 53. This curvature is a reverse curvature along the most distal portion of the free end 54. The longitudinal edges of the free ends 54 may flare outwardly. The reverse curvature and/or flaring can minimize trauma to the tissue engaged therewith.

In some embodiments suitable for mitral valve repair, the transverse width across engagement surfaces 50 (which determines the width of tissue engaged) can be at least about 2 mm, such as 3-10 mm or about 4-6 mm. In some situations, a wider engagement is desired wherein the engagement surfaces 50 can be larger, for example about 2 cm. In some embodiments, multiple implantable devices are used adjacent to each other. Arms 53 and engagement surfaces 50 can be configured to engage a length of tissue of about 4-10 mm, and preferably about 6-8 mm along the longitudinal axis of arms 53. Arms 53 can include a plurality of openings to enhance grip and to promote tissue ingrowth following implantation.

The valve leaflets can be grasped between the distal elements 18 and gripper elements 16. In some embodiments, the gripper elements 16 can be flexible, resilient, and cantilevered from coupling member 19. The gripper elements 16 can be resiliently biased toward the distal elements 18. Each gripper element 16 can be shaped and positioned to be at least partially recessed within the concavity of the distal element 18 when no tissue is present. When the implantable device 14 is in the open position, the gripper elements 16 can be shaped such that each gripper element 16 is separated from the engagement surface 50 near the proximal end 52 of arm 53 and slopes toward the engagement surface 50 near the free end 54 with the free end of the gripper element 16 contacting engagement surface 50, as illustrated in FIG. 16. This shape of the gripper elements 16 can accommodate valve leaflets or other tissues of varying thicknesses.

In the illustrated embodiment, gripper elements 16 can include a plurality of openings 63 and/or scalloped side edges 61 to increase grip on tissue. The gripper elements 16 optionally include frictional accessories, frictional features or grip-enhancing elements to assist in grasping and/or holding the leaflets. In some embodiments, the frictional accessories include barbs 60 having tapering pointed tips extending toward engagement surfaces 50. It may be appreciated that any suitable frictional accessories may be used, such as prongs, windings, bands, barbs, grooves, channels, bumps, surface roughening, sintering, high-friction pads, coverings, coatings or a combination of these.

In some embodiments, magnets may be present in the gripper elements 16 and/or distal elements 18. For example, the mating surfaces can be made from or may include material of opposite magnetic charge to cause attraction by magnetic force. For example, the gripper elements 16 and distal elements 18 may each include magnetic material of opposite charge so that tissue is held under constant compression between the gripper elements 16 and distal elements 18 to facilitate faster healing and ingrowth of tissue. The magnetic force may additionally or alternatively be used to draw the gripper elements 16 toward the distal elements 18. This may assist in deployment of the gripper elements 16. In another example, the distal elements 18 can each include magnetic material of opposite charge so that tissue positioned between the distal elements 18 is held therebetween by magnetic force.

The implantable device 14 can also include an actuation mechanism. In this embodiment, the actuation mechanism comprises two link members or legs 68, each leg 68 having a first end 70 which is rotatably joined with one of the distal elements 18 at a riveted joint 76 and a second end 72 which can be rotatably joined with a stud 74. The legs 68 can be formed of a rigid or semi-rigid metal or polymer such as Elgiloy®, cobalt chromium or stainless steel; however, any suitable material may be used. While in the embodiment illustrated both legs 68 are pinned to stud 74 by a single rivet 78, in other embodiments, each leg 68 may be individually attached to the stud 74 by a separate rivet or pin. The stud 74 may be joinable with an actuator rod (not shown) which extends through the shaft 12 and can be axially extendable and retractable to move the stud 74 and therefore the legs 68 to rotate the distal elements 18 between closed, open and/or inverted positions. Immobilization of the stud 74 can hold the legs 68 in place and therefore hold the distal elements 18 in a desired position. The stud 74 may also be locked in place by a locking feature which will be further described in later sections.

Figure 17:
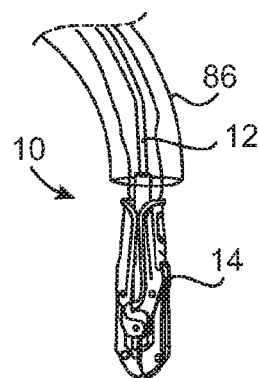

FIGS. 17-27 illustrate embodiments of the implantable device 14 of FIG. 16 in various possible positions during introduction and placement of the device 14 within the body to perform a therapeutic procedure. FIG. 17 illustrates an embodiment of an interventional tool 10 delivered through a catheter 86. It may be appreciated that the interventional tool 10 may take the form of a catheter, and the catheter 86 may take the form of a guide catheter or sheath. In this example the terms interventional tool 10 and catheter 86 will be used. The interventional tool 10 can include an implantable device 14 coupled to a shaft 12. In FIG. 17, the implantable device 14 is shown in the closed position.

Figure 18:
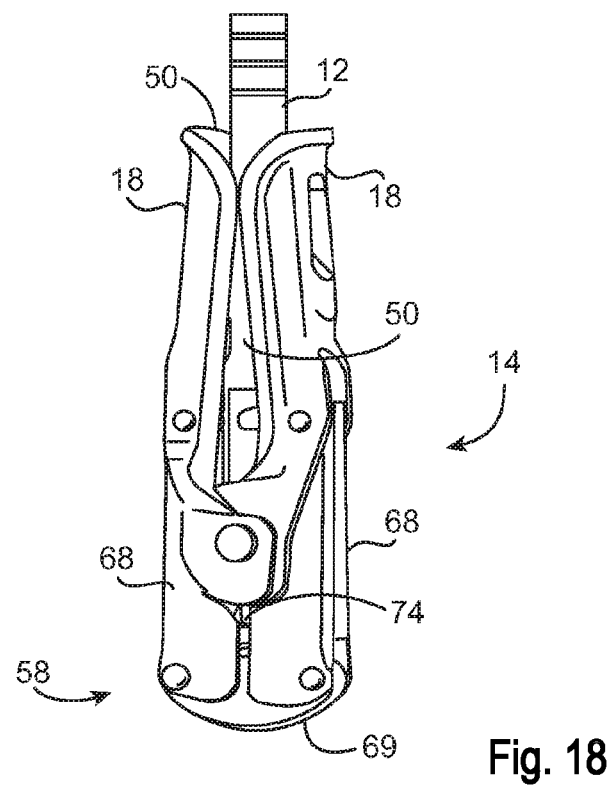

FIG. 18 illustrates a similar embodiment of the implantable device of FIG. 17 in a larger view. In the closed position, the opposed pair of distal elements 18 may be positioned so that the engagement surfaces 50 face each other. Each distal element 18 can include an elongate arm 53 having a cupped or concave shape so that together the arms 53 surround the shaft 12 and can contact each other on opposite sides of the shaft. This provides a low profile for the implantable device 14 which can be readily passable through the catheter 86 and through any anatomical structures, such as the mitral valve.

FIG. 18 illustrates an actuation mechanism. In this embodiment, the actuation mechanism includes two legs 68 which may each be movably coupled to a base 69. The base 69 may be joined with an actuator rod 64 which extends through the shaft 12 and which may be used to manipulate the implantable device 14. In some embodiments, the actuator rod 64 can attach directly to the actuation mechanism, such as the base 69. However, the actuator rod 64 may alternatively attach to a stud 74 which in turn is attached to the base 69. In some embodiments, the stud 74 can be threaded so that the actuator rod 64 attaches to the stud 74 by a screw-type action. However, the rod 64 and stud 74 may be joined by any mechanism which is releasable to allow the implantable device 14 to be detached from shaft 12.

Figure 19:
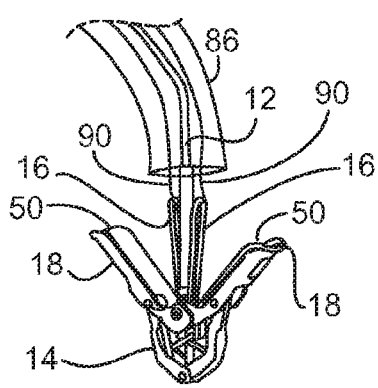
Figure 20:
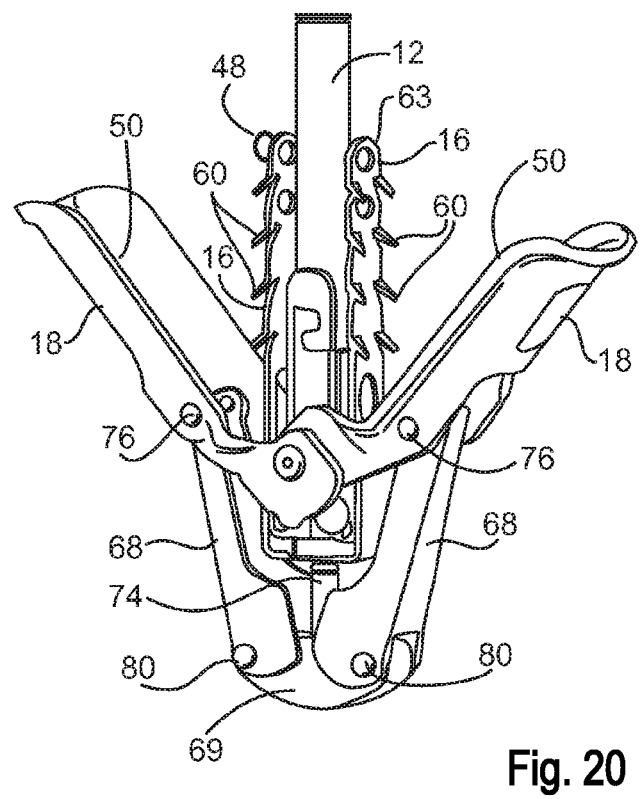

FIGS. 19-20 illustrate the implantable device 14 in the open position. In the open position, the distal elements 18 can be rotated so that the engagement surfaces 50 face a first direction. Distal advancement of the stud 74 relative to coupling member 19 by action of the actuator rod 64 can apply force to the distal elements 18 which begin to rotate around joints 76 due to freedom of movement in this direction. Such rotation and movement of the distal elements 18 radially outward can cause rotation of the legs 68 about joints 80 so that the legs 68 are directed slightly outwards. The stud 74 may be advanced to any desired distance correlating to a desired separation of the distal elements 18. In the open position, engagement surfaces 50 are disposed at an acute angle relative to shaft 12, such as at an angle of between 90 and 180 degrees relative to each other. In some embodiments, in the open position the free ends 54 of arms 53 have a span therebetween of about 10-20 mm, such as about 12-18 mm, and preferably about 14-16 mm.

Gripper elements 16 can be biased outwardly toward arms 53. The gripper elements 16 may be moved inwardly toward the shaft 12 and held against the shaft 12 with the aid of one or more gripper lines 90, which can be in the form of sutures, wires, nickel-titanium alloy wire, rods, cables, polymeric lines, or other suitable structures. The gripper lines 90 may be connected with the gripper elements 16 by threading the gripper lines 90 in a variety of ways. When the gripper elements 16 have a loop shape, as shown in FIG. 19, a gripper line 90 may pass through the loop and double back. When the gripper elements 16 have an elongate solid shape, as shown in FIG. 20, a gripper line 90 may pass through one or more of the openings 63 in the element 16.

A line loop 48 may be included on a gripper element 16, as illustrated in FIG. 20, through which a gripper line 90 may pass and double back. Such a line loop 48 may be useful to reduce friction on gripper line 90 or when the gripper elements 16 are solid or devoid of other loops or openings through which the gripper lines 90 may attach and/or pass through. A gripper line 90 may attach to the gripper elements 16 by detachable means which would allow a single line 90 to be attached to a gripper element 16 without doubling back and/or would allow the single line 90 to be detached directly from the gripper element 16 when desired. Examples of such detachable means include hooks, snares, clips or breakable couplings. By applying sufficient tension to the gripper line 90, the detachable means may be detached from the gripper element 16 such as by breakage of the coupling. Other mechanisms for detachment may also be used. A lock line 92 may be attached and detached from a locking mechanism by similar detachable means.

The interventional tool 10 may be repeatedly manipulated to reposition the implantable device 14 so that the leaflets are properly contacted or grasped at a desired location. Repositioning can be achieved with the implantable device in the open position. In some instances, regurgitation may also be checked while the device 14 is in the open position. If regurgitation is not satisfactorily reduced, the device may be repositioned and regurgitation checked again until desired results are achieved.

Figure 21:
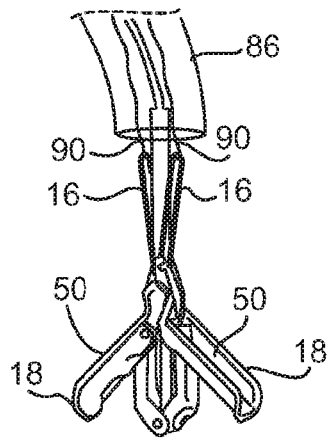
Figure 22:
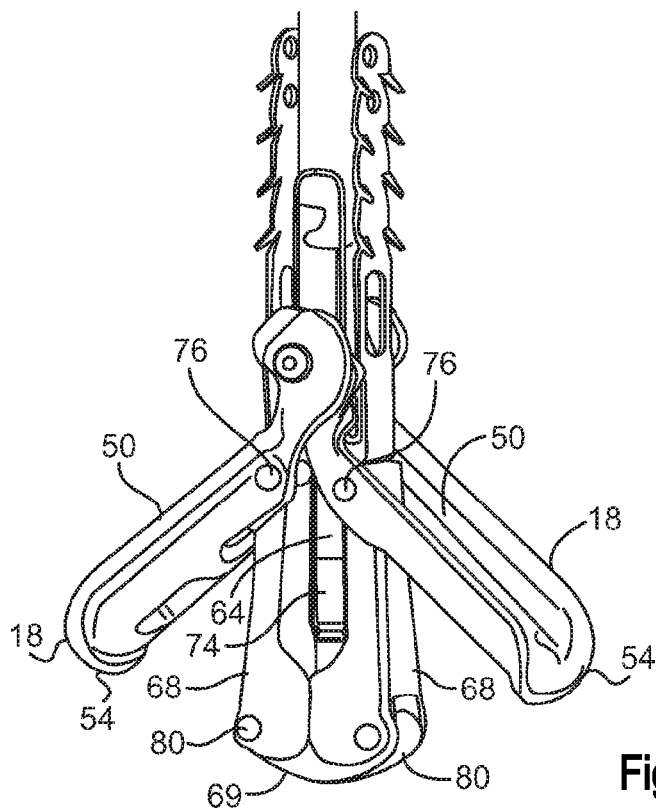

It may also be desired to invert the implantable device 14 to aid in repositioning or removal of the implantable device 14. FIGS. 21-22 illustrate the implantable device 14 in the inverted position. By advancement of stud 74 relative to coupling member 19, the distal elements 18 can be further rotated so that the engagement surfaces 50 face outwardly and free ends 54 point distally, with each arm 53 forming an obtuse angle relative to shaft 12. The angle between arms 53 is preferably in the range of about 270 to 360 degrees. Further advancement of the stud 74 can further rotate the distal elements 18 around joints 76. This rotation and movement of the distal elements 18 radially outward can cause rotation of the legs 68 about joints 80 so that the legs 68 are returned toward their initial position (e.g., generally parallel to each other). The stud 74 may be advanced to any desired distance correlating to a desired inversion of the distal elements 18. Preferably, in the fully inverted position, the span between free ends 54 is no more than about 20 mm, usually less than about 16 mm, and preferably about 12-14 mm.

In this illustration, the gripper elements 16 remain positioned against the shaft 12 by exerting tension on the gripper lines 90. Thus, a relatively large space may be created between the gripper elements 16 and the distal elements 18 for repositioning. In addition, the inverted position allows withdrawal of the implantable device 14 through the valve while minimizing trauma to the leaflets. Engagement surfaces 50 can provide an atraumatic surface for deflecting tissue as the implantable device is retracted proximally. It should be further noted that barbs 60 are angled slightly in the distal direction (away from the free ends of the gripper elements 16), reducing the risk that the barbs will catch on or lacerate tissue as the implantable device is withdrawn.

Figure 23:
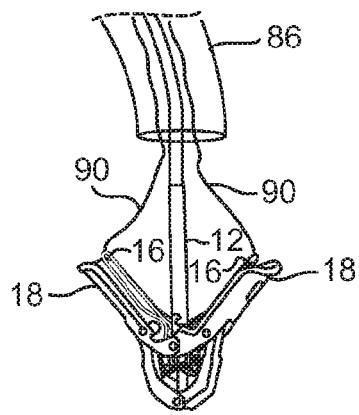
Figure 24:
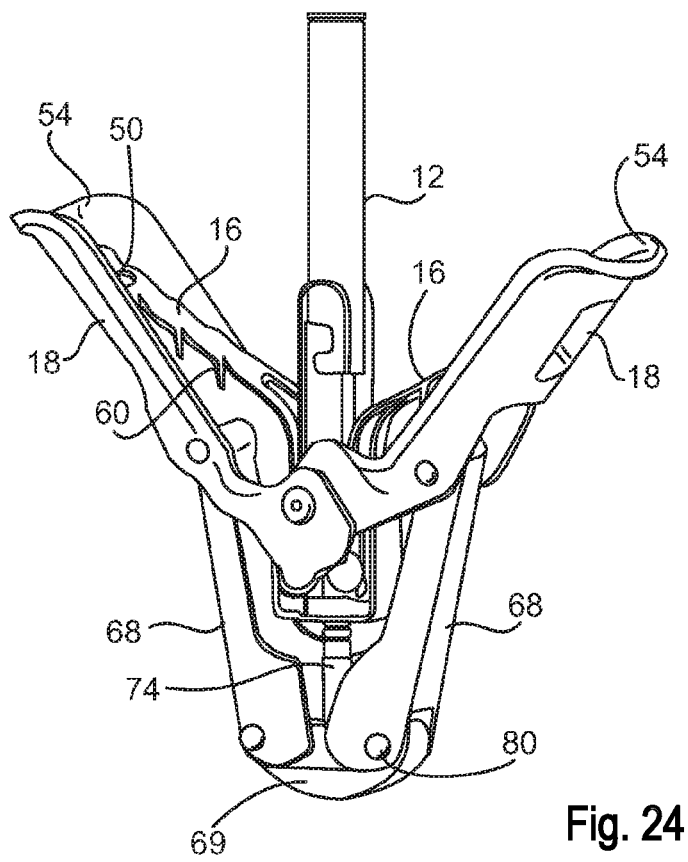

Once the implantable device 14 has been positioned in a desired location against the valve leaflets, the leaflets may then be captured between the gripper elements 16 and the distal elements 18. FIGS. 23-24 illustrate the implantable device 14 in such a position. Here, the gripper elements 16 are lowered toward the engagement surfaces 50 so that the leaflets can be held therebetween. In FIG. 24, the gripper elements 16 are shown to include barbs 60, which may be used to provide atraumatic gripping of the leaflets. Alternatively, larger, more sharply pointed barbs or other penetration structures may be used to pierce the leaflets to more actively assist in holding them in place. This position is similar to the open position of FIGS. 19-20; however, the gripper elements 16 are now lowered toward arms 53 by releasing tension on gripper lines 90 to compress the leaflet tissue therebetween. At any time, the gripper elements 16 may be raised and the distal elements 18 adjusted or inverted to reposition the implantable device 14 (e.g., if regurgitation is not sufficiently reduced).

Figure 25:
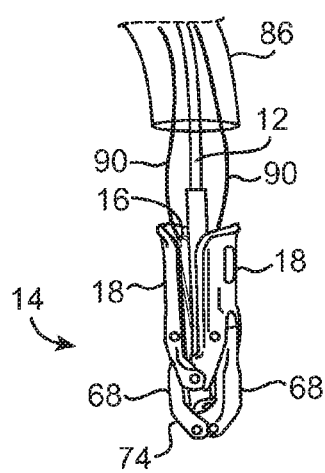

After the leaflets have been captured between the gripper elements 16 and distal elements 18 in a desired arrangement, the distal elements 18 may be locked to hold the leaflets in this position or the implantable device 14 may be returned to or toward a closed position. Such locking will be described in a later section. FIG. 25 illustrates the implantable device 14 in the closed position wherein the leaflets (not shown) can be captured and coapted. This can be achieved by retraction of the stud 74 proximally relative to coupling member 19 so that the legs 68 of the actuation mechanism 58 can apply an upwards force to the distal elements 18, which in turn rotate the distal elements 18 so that the engagement surfaces 50 again face one another. The released gripper elements 16, which are biased outwardly toward distal elements 18, are concurrently urged inwardly by the distal elements 18. The implantable device 14 may then be locked to hold the leaflets in this closed position.

Figure 26:
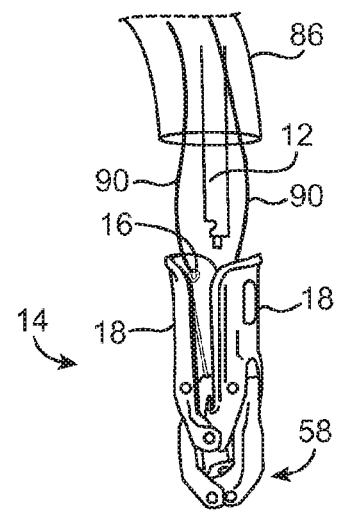

As shown in FIG. 26, the implantable device 14 may then be released from the shaft 12. As mentioned, the implantable device 14 is releasably coupleable to the shaft 12 by coupling member 19. FIG. 26 illustrates the coupling structure, a portion of the shaft 12 to which the coupling member 19 of the implantable device 14 attaches. As shown, the gripper lines 90 may remain attached to the gripper elements 16 following detachment from shaft 12 to function as a tether to keep the implantable device 14 connected with the catheter 86. Optionally, a separate tether coupled between shaft 12 and implantable device 14 may be used expressly for this purpose while the gripper lines 90 are removed. The repair of the leaflets or tissue may be observed by non-invasive visualization techniques, such as echocardiography. If the repair is not desired, the implantable device 14 may be retrieved with the use of the tether and/or gripper lines 90 so as to reconnect coupling member 19 with shaft 12.

The one or more gripper lines 90 may be elongated flexible threads, wire, cable, sutures or lines extending through shaft 12, looping through gripper elements 16, and extending back through shaft 12 to its proximal end. When detachment is desired, one end of each line may be released at the proximal end of the shaft 12 and the other end pulled to draw the free end of the line distally through shaft 12 and through gripper element 16 thereby releasing the implantable device.

Figure 27:
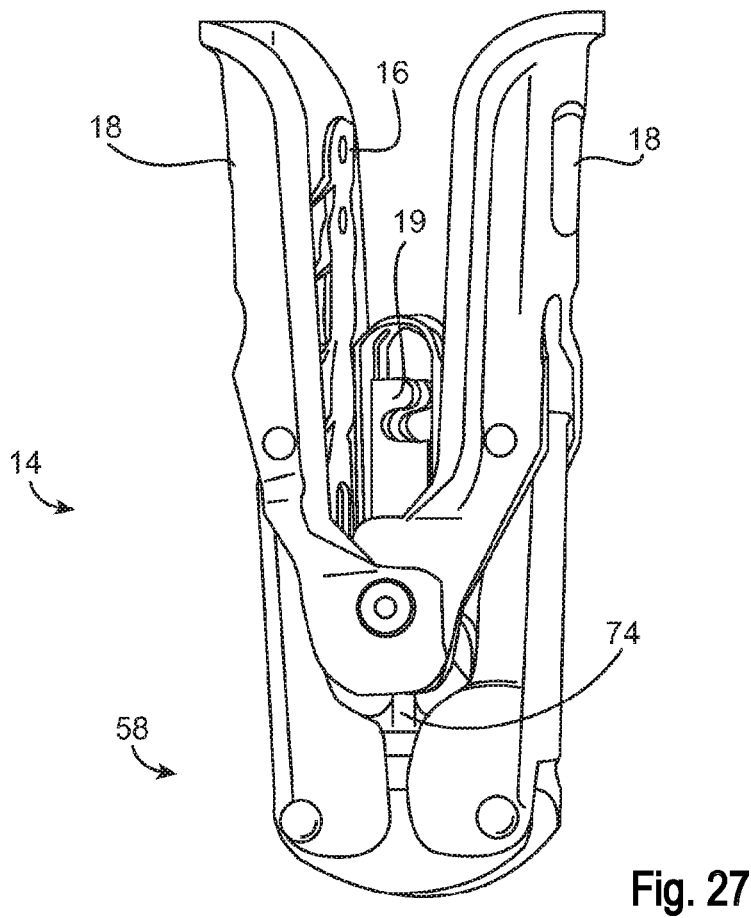

FIG. 27 illustrates a released implantable device 14 in a closed position. As shown, the coupling member 19 remains separated from the shaft 12 of the interventional tool 10 and the gripper elements 16 are deployed so that tissue (not shown) may reside between the gripper elements 16 and distal elements 18.

While the above described embodiments of the invention utilize a push-to-open, pull-to-close mechanism for opening and closing distal elements 18, other embodiments can include a pull-to-open, push-to-close mechanism. For example, distal elements 18 may be coupled at their proximal ends to stud 74 rather than to coupling member 19, and legs 68 may be coupled at their proximal ends to coupling member 19 rather than to stud 74. In this example, when stud 74 is pushed distally relative to coupling member 19, distal elements 18 would close, while pulling on stud 74 proximally toward coupling member 19 would open distal elements 18.

B. Implantable Device Locking Mechanisms

Figure 28:
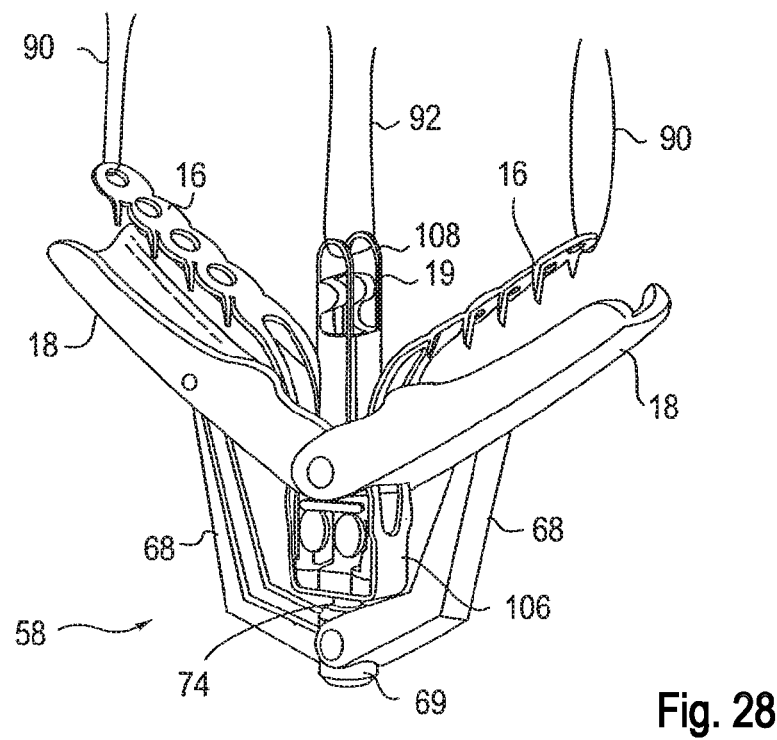
FIGS. 28-31 illustrate an embodiment of a fixation device including a locking mechanism.

The implantable device 14 may include a locking mechanism for locking the device 14 in a particular position, such as an open, closed or inverted position or any position therebetween. FIGS. 28-31 illustrate an embodiment of a locking mechanism 106. Referring to FIG. 28, in this embodiment, the locking mechanism 106 may be disposed between the coupling member 19 and the base 69 of the actuation mechanism 58. The base 69 can be fixedly attached to the stud 74 which extends through the locking mechanism 106. The stud 74 may be releasably attached to the actuator rod 64 which passes through the coupling member 19 and the shaft 12 of the interventional tool 10. The base 69 can also connected to the legs 68 of the actuation mechanism 58 which are in turn connected to the distal elements 18.

FIG. 28 also illustrates the gripper elements 16, which in this embodiment straddle the locking mechanism and join beneath the locking mechanism 106 as an integral gripper. The gripper elements 16 are shown supported by gripper lines 90. The gripper elements 16 may be raised and lowered by manipulation of the gripper lines 90. In addition, lock lines 92 are shown connected with a release harness 108 of the locking mechanism 106. The lock lines 92 may be used to lock and unlock the locking mechanism 106 as will be described below. The gripper lines 90 and lock lines 92 may be formed of any suitable material, such as wire, nickel-titanium alloy wire, cable, suture, or thread, to name a few.

Figure 29:
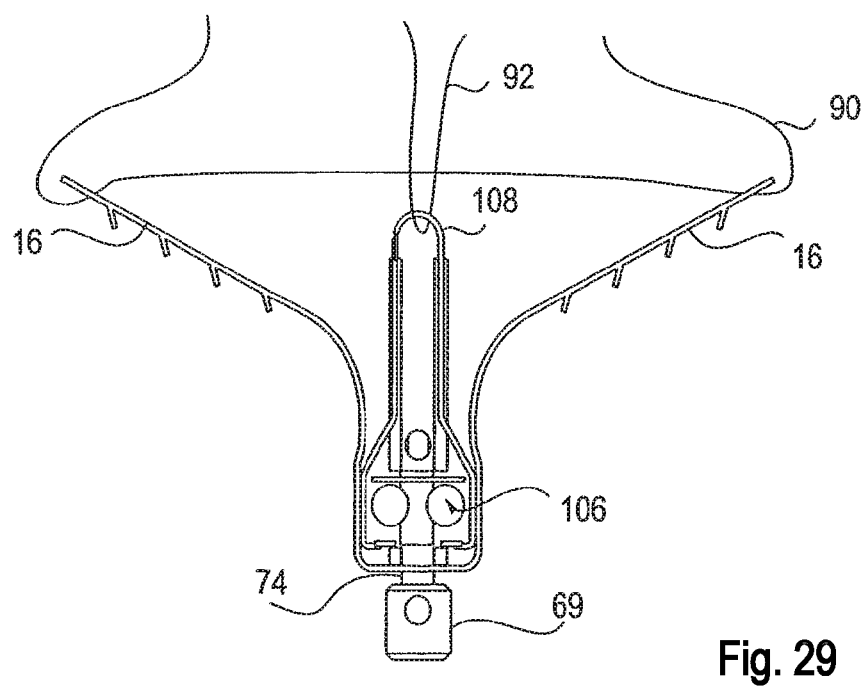

FIG. 29 provides a front view of the locking mechanism 106 of FIG. 28. In this embodiment, the gripper elements 16 are supported by a single gripper line 90 which is passed through both of the gripper elements 16. In this arrangement both of the gripper elements 16 are raised and lowered simultaneously by action of a single gripper line 90. Whether the gripper elements 16 are manipulated individually by separate gripper lines 90 or jointly by a single gripper line 90, the gripper lines 90 may extend directly through openings in the gripper elements and/or through a layer or portion of a covering 100 on the gripper elements, and/or through a suture loop above or below a covering 100.

Figure 30:
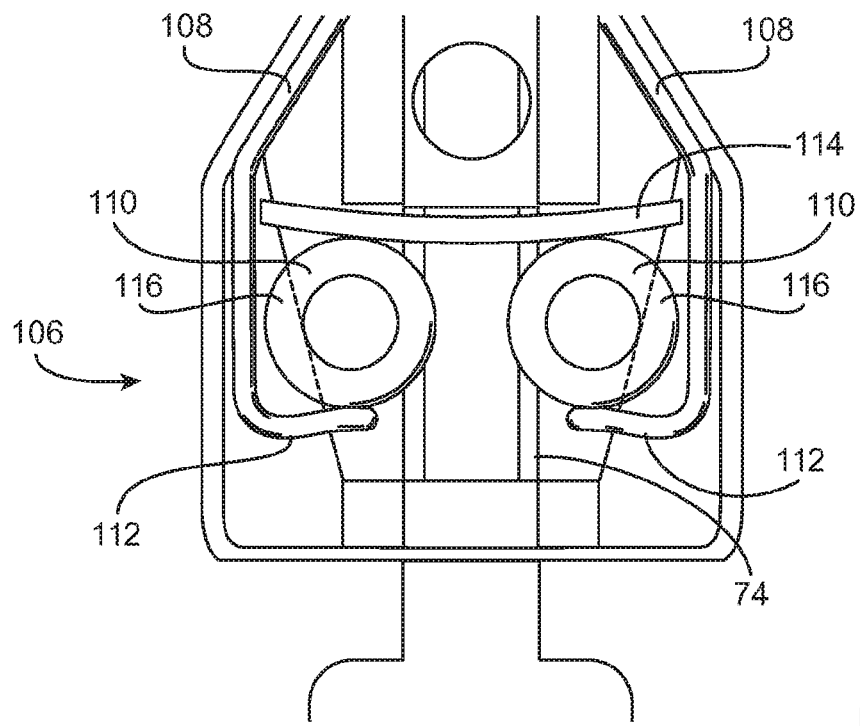
Figure 31:
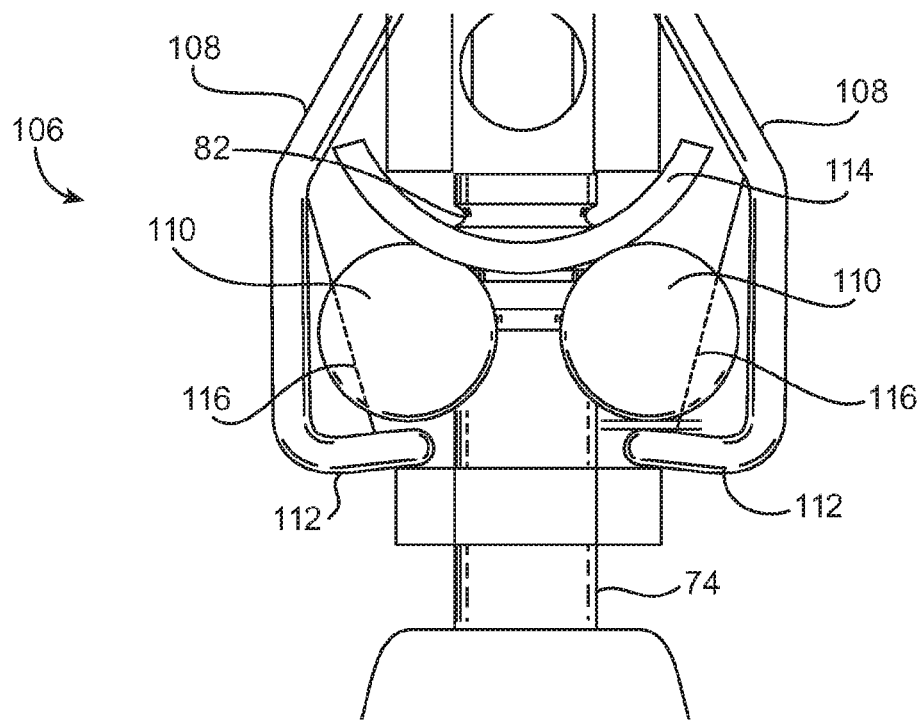

FIGS. 30-31 illustrate an embodiment of a locking mechanism 106 showing the locking mechanism 106 in the unlocked and locked positions, respectively. Referring to FIG. 30, the locking mechanism 106 can include one or more wedging elements, such as rolling elements. In this embodiment, the rolling elements include a pair of barbells 110 disposed on opposite sides of the stud 74, each barbell having a pair of generally cylindrical caps and a shaft therebetween. The barbells 110 and the stud 74 can be formed of cobalt chromium or stainless steel, however any suitable material may be used.

The barbells 110 may be manipulated by hooked ends 112 of the release harness 108. When an upwards force is applied to the harness 108 by the lock line 92 (illustrated in FIG. 28), the hooked ends 112 can raise the barbells 110 against a spring 114, as shown in FIG. 30. This draws the barbells 110 up along a sidewall or sloping surface 116 which unwedges the barbells 110 from against the stud 74. In this position, the stud 74 is free to move. Thus, when the lock line 92 raises or lifts the harness 108, the locking mechanism 106 is placed in an unlocked position wherein the stud 74 is free to move the actuation mechanism 58 and therefore the distal elements 18 to any desired position.

Release of the harness 108 by the lock line 92 transitions the locking mechanism 106 to a locked position, illustrated in FIG. 31. By releasing the upwards force on the barbells 110 by the hooked ends 112, the spring 114 forces the barbells 110 downwards and wedges the barbells 110 between the sloping surface 116 and the stud 74. This restricts motion of the stud 74, which in turn locks the actuation mechanism 58 and therefore distal elements 18 in place. The stud 74 may include one or more grooves 82 or indentations which receive the barbells 110. This may provide more rapid and positive locking by causing the barbells 110 to settle in a definite position, increase the stability of the locking feature by further preventing movement of the barbells 110, as well as providing a tangible indication to the user that the barbell has reached a locking position.

The grooves 82 may be used to indicate the relative position of the distal elements 18, such as the distance between the distal elements 18. For example, each groove 82 may be positioned to correspond with a 0.5 or 1.0 mm (or other size) decrease in distance between the distal elements 18. As the stud 74 is moved, the barbells 110 can contact the grooves 82; by counting the number of grooves 82 that are felt as the stud 74 is moved, the user can determine the distance between the distal elements 18 and can provide the desired degree of coaptation based upon leaflet thickness, geometry, spacing, blood flow dynamics and/or other factors. Thus, the grooves 82 may provide tactile feedback to the user.

The illustrated locking mechanism 106 allows the implantable device 14 to remain in an unlocked position when attached to the interventional tool 10 during grasping and repositioning and then maintain a locked position when left behind as an implant. The locking mechanism 106 may be repeatedly locked and unlocked throughout the placement of the implantable device 14, if desired. Once the final placement is determined, the lock line 92 and gripper line 90 are removed and the implantable device can be left behind.

IV. Delivery Device

A. Overview of Delivery Device

Figure 32:
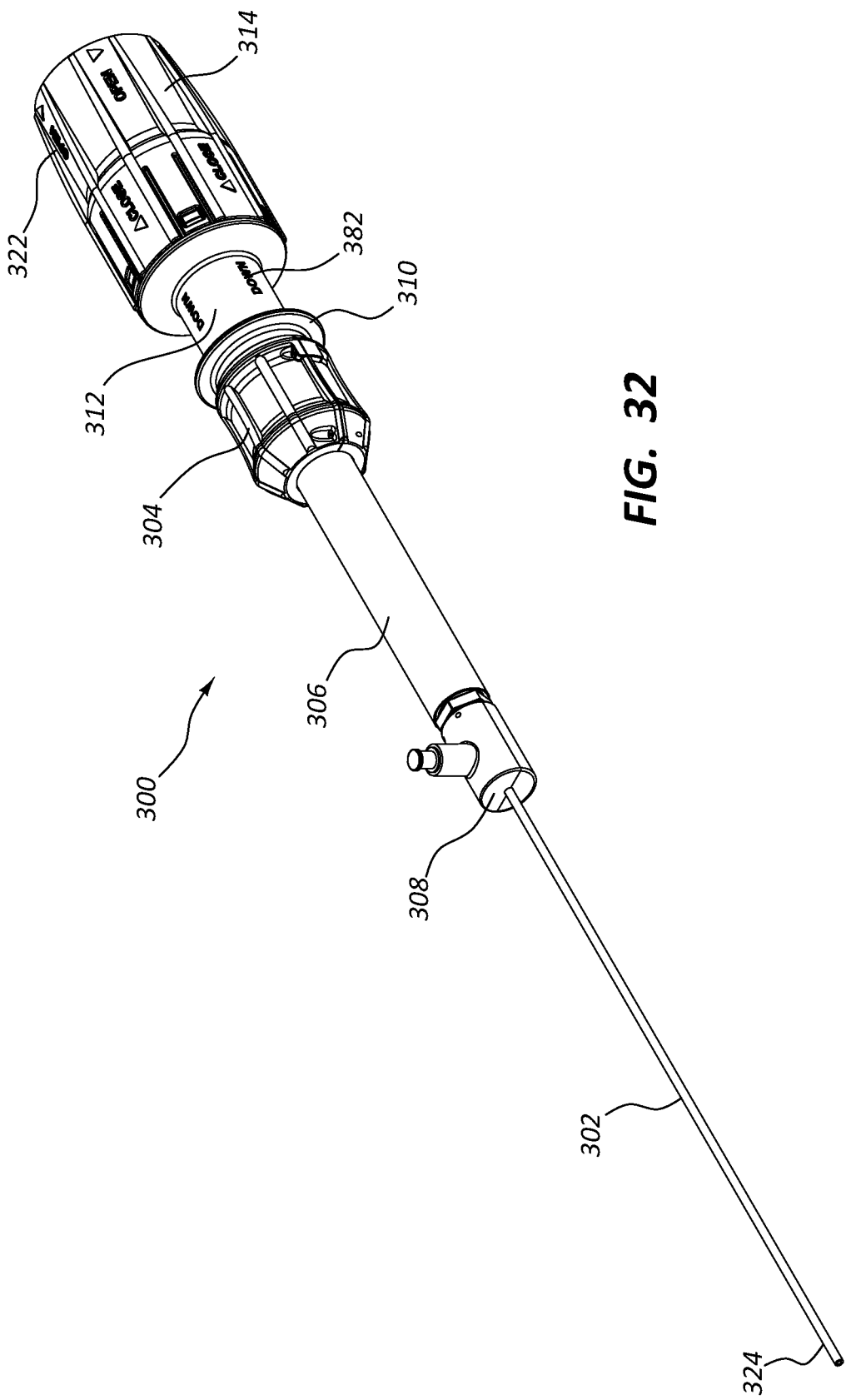
FIG. 32 illustrates a delivery device according to the present disclosure.

FIG. 32 illustrates an embodiment of a delivery device 300 which may be used to introduce and position an implantable device at a target location as described above. As illustrated, the delivery device 300 can include a proximal end 322 and a distal end 324, and a shell 306 disposed between the proximal end 322 and distal end 324. As described in further detail below, the shell 306 can be configured to hold and/or position various components passing from the proximal end 322 toward the distal end 324, such as lock lines, gripper lines, actuator rod components, and the like.

As shown, a fluid management system 308 can be coupled to the shell 306 and can extend distally from the shell 306. A delivery catheter 302 can be coupled to the fluid management system 308 and can extend distally from the fluid management system 308. As described in further detail below, the fluid management system 308 can be configured to gather and/or direct various components (e.g., lock lines, gripper lines, actuator rod) passing from the proximal side 322 to the distal side 324 so as to position the various components within the delivery catheter 302. The fluid management system 308 can be configured to receive a fluid to be flushed into the delivery catheter 302 and/or to seal off other components of the delivery device 300 (e.g., shell 306 and/or other components located proximal to the fluid management system 308) in order to provide dry operation of the other components of the delivery device 300.

The illustrated delivery device 300 can include a translation knob 304 coupled to the shell 302 and extending proximally from the shell 302. The translation knob 304 may be configured as a handle and/or gripping surface. For example, the translation knob 304 can allow a user to position the delivery device 300 (e.g., by rotating and/or translating) by providing a surface for gripping and/or handling the delivery device 300. As shown, the translation knob 304 may include one or more fins and/or grooves arranged to aid a user in manipulating the delivery device 300.

The delivery device 300 may include a collar 310, at least a portion of which may be positioned proximal to the translation knob 304. As described in further detail below, the collar 310 may be configured as a control for one or more gripper lines (not shown) and/or lock lines (not shown) in order to, for example, position the gripper elements and/or adjust the locking of an attached implantable device (e.g., the implantable device 14 shown in FIGS. 16-31). For example, the collar 310 can be configured so as to be translatable along a shaft 312, and the collar 310 can be configured to apply or release tension in one or more gripper lines and/or to apply or release tension in one or more lock lines by sliding of the collar 310 proximally or distally along the shaft 312.

The delivery device 300 may include a deployment handle 314 disposed proximal to the shaft 312. As described in further detail below, the deployment handle 314 may be configured to actuate movement of an actuator rod (not shown) in order to, for example, position the distal elements of an attached implantable device (e.g., the implantable device 14 shown in FIGS. 16-31). In addition, as described in further detail below, the deployment handle 314 may be configured to provide staged deployment of an attached implantable device. For example, the deployment handle can be configured to ensure proper deployment of an implantable device by forcing and/or reminding an operator to follow the proper procedure for deploying the implantable device. Further, the deployment handle 314 may be configured to provide control over the locking and/or unlocking of an attached implantable device (e.g., by working in conjunction with the collar 310).

Figure 33:
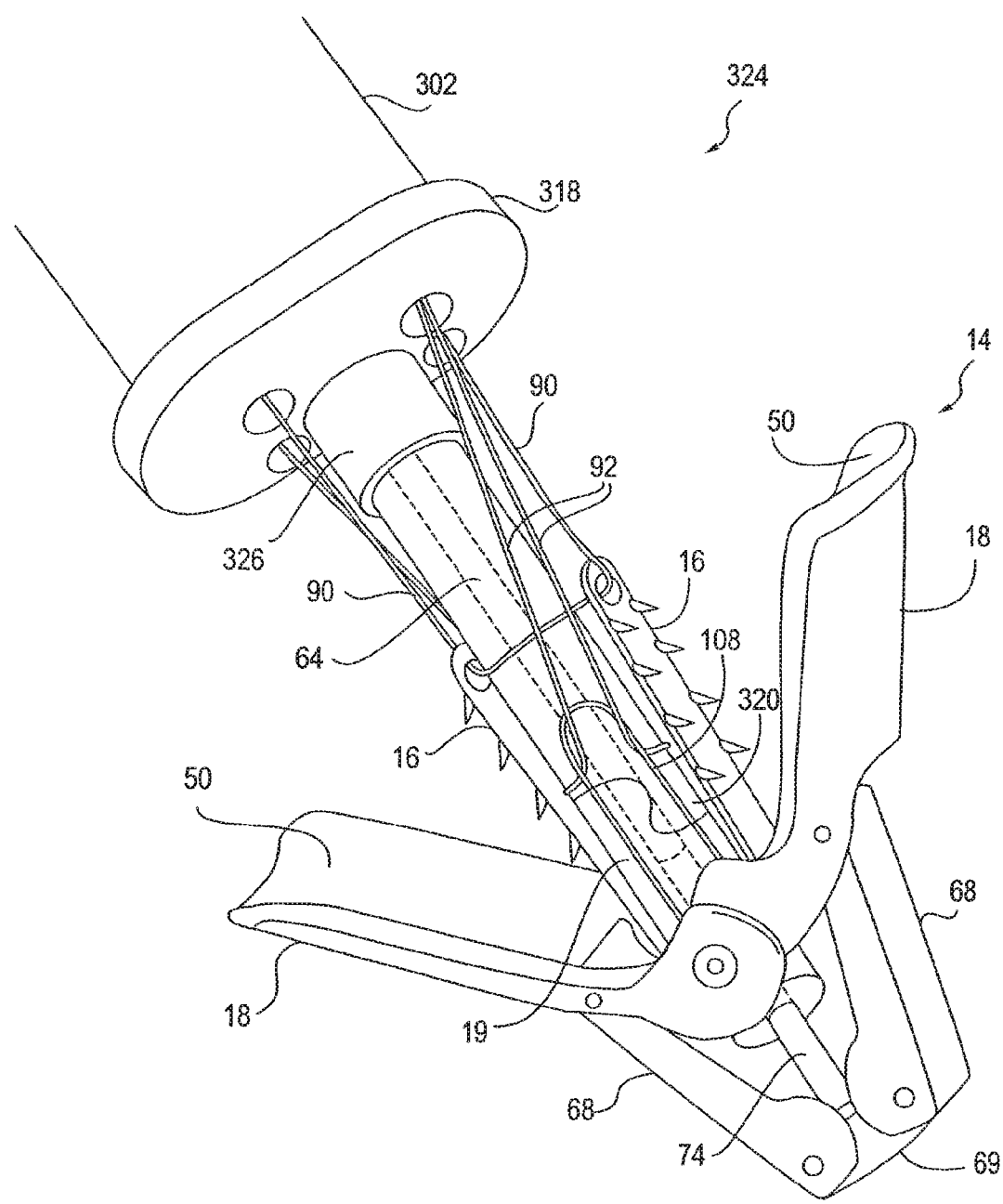
FIGS. 33-34 illustrate a fixation device that is coupleable to a delivery catheter.

FIG. 33 illustrates an embodiment of an implantable device 14 coupled to the distal end 324 of a delivery catheter 302. The delivery catheter 302 is shown having a nose 318 near its distal end 324. In this embodiment, the nose 318 has a flanged shape. Such a flanged shape prevents the nose 318 from being retracted into a guiding catheter or introducer. In other embodiments, the nose 318 may have any shape including bullet, rounded, blunt, or pointed, to name a few. A compression coil 326 can extend from the nose 318, through which the coupling structure 320 and/or actuator rod 64 can pass. The actuator rod 64 may be coupleable, as shown, with the stud 74 of the implantable device 14. Such coupling is illustrated in FIG. 34.

Figure 34:
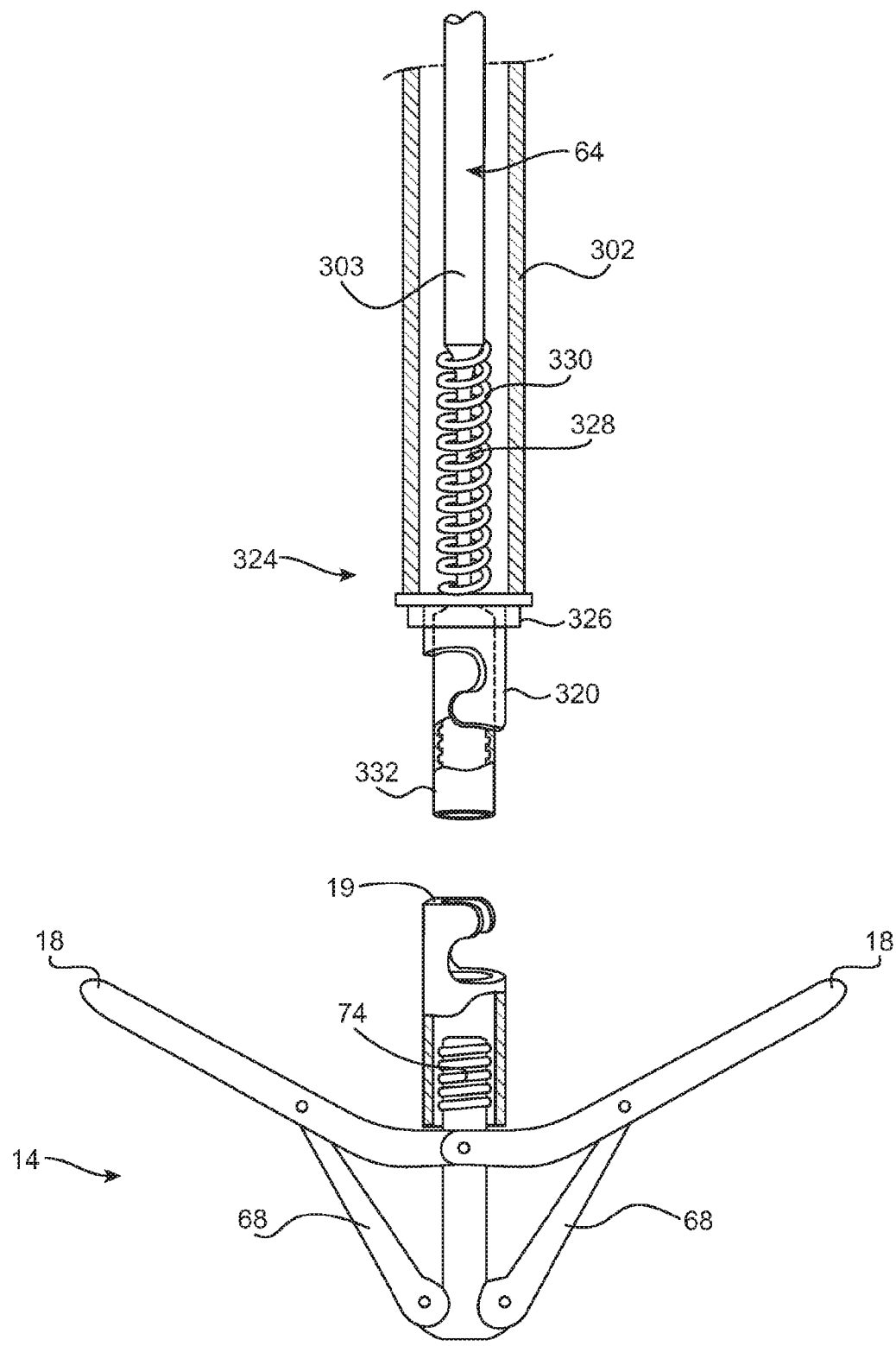

FIG. 34 illustrates a portion of the delivery catheter 302 and an implantable device 14 which is coupleable with a delivery catheter 302. The actuator rod 64 can pass through the delivery catheter 302. In this embodiment, the actuator rod 64 comprises a proximal extremity 303 and a distal extremity 328. The distal extremity 328 may be surrounded by a coil 330. The proximal extremity 303 may be formed of stainless steel, nickel-titanium alloy, and/or ELGILOY®, to name a few, and may have a diameter in the range of 0.010 in. to 0.040 in., preferably 0.020 in. to 0.030 in., more preferably 0.025 in., and a length in the range of 48 to 72 in. The distal extremity 328 may be tapered, is typically formed of stainless steel, nickel-titanium alloy, and/or ELGILOY®, to name a few, and may have a diameter in the range of 0.011 to 0.025 in and a length in the range of 4 to 12 in. Such narrowing increases flexibility of the distal end 324 of the actuator rod 64.

The actuator rod 64 may include a joiner 332 attached to the distal extremity 328. The joiner 332 may be removably attachable with stud 74 of the implantable device 14. In this embodiment, the joiner 332 has internal threads which can mate with external threads on the stud 74 of the implantable device 14. As described previously, the stud 74 may be connected with the distal elements 18 so that advancement and retraction of the stud 74, by means of the actuator rod 64, manipulates the distal elements. The coupling member 19 of the implantable device 14 can mate with the coupling structure 320 of the catheter 300. Thus, the coupling member 19 and coupling structure 320 can function as previously described in relation to FIGS. 10-11.

Referring back to FIG. 33, the implantable device 14 may also include a locking mechanism which includes a release harness 108, as previously described in relation to FIGS. 28-31. Lock lines 92 may be connected with the release harness 108 to lock and unlock the locking mechanism 106. The lock lines 92 may extend through the delivery catheter 302 and may connect with the release harness 108 in various arrangements as described in further detail below. Gripper lines 90 may extend through the delivery catheter 302 and connect with the gripper elements 16. The gripper elements 16 can be raised and lowered by manipulation of the gripper lines 90 as previously described. The gripper lines 90 may connect with the gripper elements 16 in various arrangements as described in further detail below.

B. Lock Line Arrangements

Figure 35:
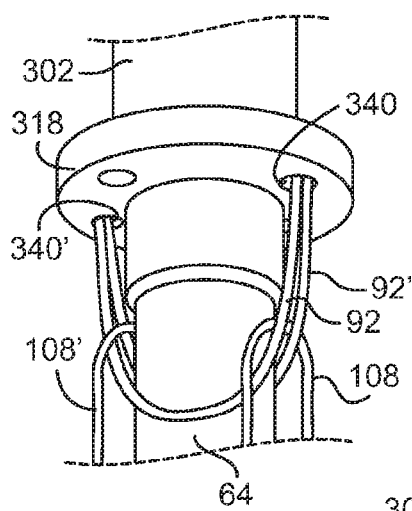
FIGS. 35-37 illustrate various arrangements of lock lines engaging a locking mechanism.
Figure 36:
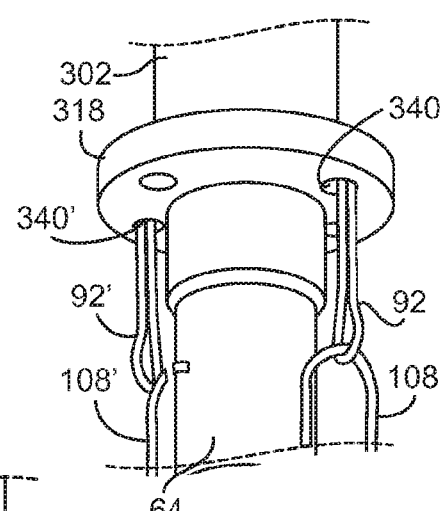
Figure 37:
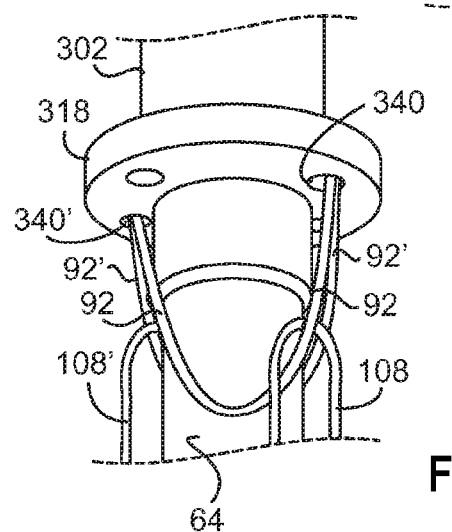

In embodiments including one or more lock lines 92, the lock lines 92 can pass through at least one lock line lumen 340 in the delivery catheter 302. The lock lines 92 may engage the release harnesses 108 in various arrangements, examples of which are illustrated in FIGS. 35-37. In the illustrated embodiments, two lock line lumens 340 are present within the delivery catheter 302 terminating at the nose 318. The lumens 340 can be disposed on alternate sides of the actuator rod 64 so that each lumen 340 is directed toward a release harness 108.

FIG. 35 illustrates an embodiment wherein two lock lines 92, 92' pass through a single lock line lumen 340 and are threaded through a release harness 108 on one side of the actuator rod 64 (the actuator rod 64 is shown without surrounding housing such as coupling structure, for clarity). The lock lines 92, 92' can then be separated so that each lock line passes on an opposite side of the actuator rod 64. The lock lines 92, 92' can then pass through the release harness 108' on the opposite side of the actuator rod 64 and continue together passing through a another single lock line lumen 340'. This lock line arrangement is also illustrated in FIG. 33.

FIG. 36 illustrates an embodiment wherein one lock line 92 can be passed through a single lock line lumen 340, can be threaded through a release harness 108 on one side of the actuator rod 64, and can be returned to the lock line lumen 340. Another lock line 92' can be passed through another single lock line lumen 340', can be threaded through a different release harness 108' located on the opposite side of the actuator rod 64, and can be returned to the another single lock line lumen 340'.

FIG. 37 illustrates an embodiment wherein both lock lines 92, 92' can be passed through a single lock line lumen 340. One lock line 92 can be threaded through a release harness 108 on one side of the actuator rod 64 and can then be passed through another lock line lumen 340' on the opposite side of the actuator rod 64. The other lock line 92' can be threaded through another release harness 108' on the other side of the actuator rod 64 and can then be passed through the another lock line lumen 340' with the previous lock line 92.

Other embodiments may include a variety of lock line arrangements. Various arrangements can be configured to allow the harnesses 108 to be manipulated independently or jointly, to allow various amounts of tension to be applied, and/or to vary the force required for removal of the lock lines when the implantable device is to be left behind. For example, a single lock line passing through one or two lumens may be connected to both release harnesses for simultaneous application of tension.

C. Gripper Line Arrangements

Figure 38:
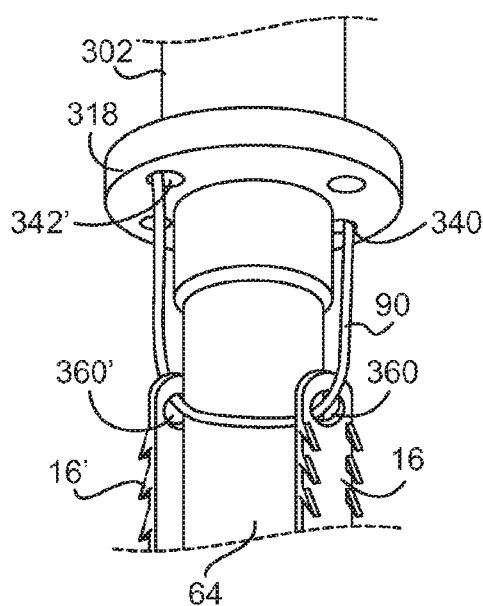
FIGS. 38-39 illustrate various arrangements of gripper lines engaging grippers.
Figure 39:
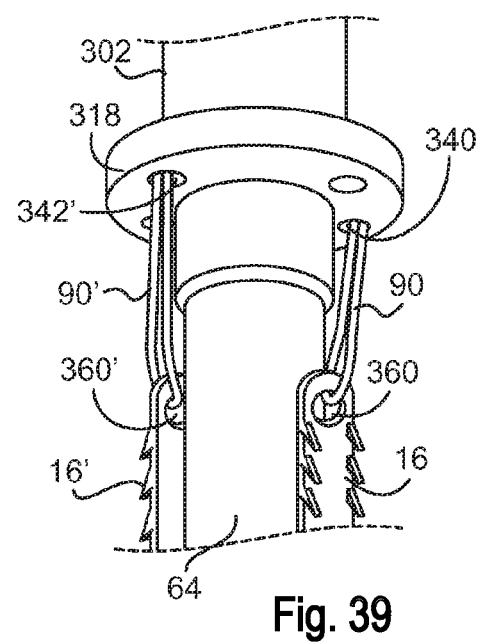

In embodiments including gripper lines 90, the gripper lines 90 can be passed through at least one gripper line lumen 342 in the delivery catheter 302 and at least one gripper element 16. The gripper lines 90 may engage the gripper elements 16 in various arrangements, examples of which are illustrated in FIGS. 38-39. In the illustrated embodiments, two gripper line lumens 342 are present within the delivery catheter 302 terminating at the nose 318. The lumens 342 can be disposed on alternate sides of the actuator rod 64 (the actuator rod 64 is shown without surrounding housing such as coupling structure, for clarity) so that each lumen 342 is directed toward a separate gripper element 16.

FIG. 38 illustrates an embodiment wherein one gripper line 90 passes through a single gripper line lumen 342. The gripper line 90 can be threaded through an eyelet 360 of a gripper element 16 on one side of the actuator rod 64, passed over the actuator rod 64, and be threaded through an eyelet 360' of another gripper element 16' on the other side of the actuator rod 64. The gripper line 90 can then be passed through another single gripper line lumen 342'. This gripper line arrangement is the same arrangement illustrated in FIG. 33.

FIG. 39 illustrates an embodiment wherein one gripper line 90 can be passed through a single gripper line lumen 342, can be threaded through an eyelet 360 of a gripper element 16 on one side of the actuator rod 64, and can then be returned to the gripper line lumen 342. Optionally, another gripper line 90' can be passed through another single gripper line lumen 342' on the opposite side of the actuator rod 64, and can be returned to the another single gripper line lumen 342'.

Other embodiments may include a variety of gripper line arrangements. The various arrangements can allow the gripper elements to be manipulated independently or jointly, allow various amounts of tension to be applied, and/or can vary the force required for removal of the gripper lines when the implantable device is to be left behind. For example, a single gripper line passing through one or two lumens in the delivery catheter 302 may be used for simultaneous actuation of both gripper elements 16. In addition, snares or hooks may be mounted within delivery catheter 302 so as to be movable distally to engage gripper elements 16 and draw them away from distal elements 18.

D. Fluid Management System

Figure 40:
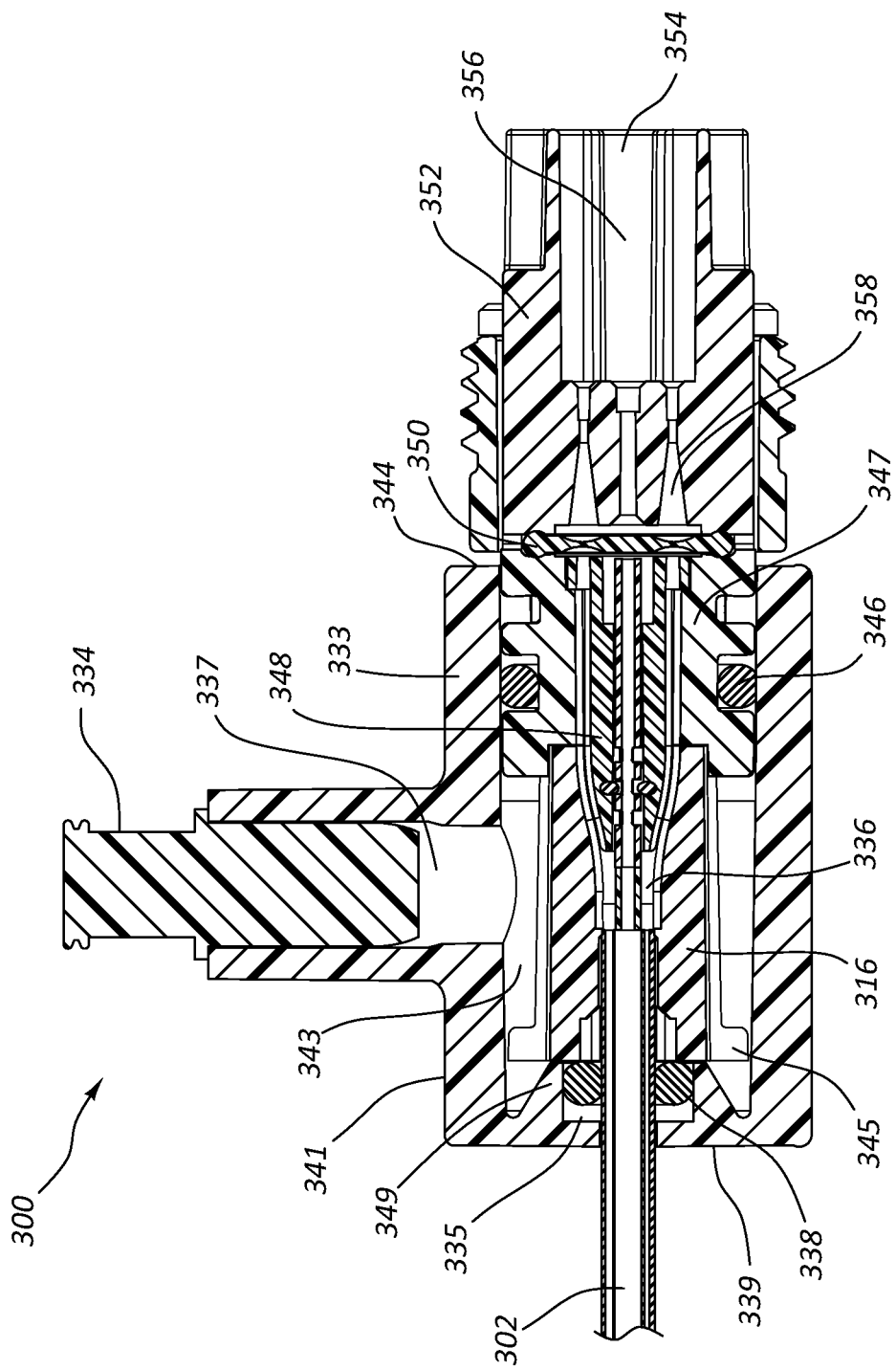
FIGS. 40-41 illustrate various components of a fluid management system according to the present disclosure.

FIG. 40 illustrates a cutaway view of the fluid management system 308 illustrated in FIG. 32. As illustrated, the fluid management system 308 can include a grommet 316. The delivery catheter 302 can be coupled to the grommet 316 and can extend distally from the grommet 316 (e.g., out of the delivery catheter outlet 335). As shown in the illustrated embodiment, the grommet 316 can be formed with an interior lumen configured in size and shape to engage with the delivery catheter 302 in order to allow the delivery catheter 302 to be coupled to the grommet 316. For example, the proximal end of the delivery catheter 302 may be inserted into an interior lumen 336 of the grommet 316.

The grommet 316 may be housed inside a flush body 333. As shown in the illustrated embodiment, the flush body 333 can be formed with a cylindrical shape. The flush body 333 can include a delivery catheter outlet 335, a fluid inlet 337, and an opening 344. The fluid inlet 337 can be configured to receive fluids (e.g., saline, heparinized saline, and/or other fluids with or without other drugs) for delivery into the delivery catheter 302. In the illustrated embodiment, the flush body 333 is formed with a cylindrical shape. In other embodiments, the flush body 333 may be formed in other shapes, such as shapes having triangular, square, rectangular, or other polygonal cross-sections, or ovoid or ellipsoid cross-sections.

In the illustrated embodiment, the delivery catheter outlet 335 and the fluid inlet 337 are positioned with longitudinal axes that are transverse to each other, with the delivery catheter outlet 335 being positioned on a distal face 339 of the flush body 333 and the fluid inlet 337 is positioned on a side portion 341 of the flush body 333. In other embodiments, the flush body 333 may include a delivery catheter outlet 335 and/or a fluid inlet 337 that are oriented in an alternative arrangement. For example, some embodiments may include a delivery catheter outlet and a fluid inlet that are both oriented on a distal face of a flush body. Other embodiments may include a delivery catheter outlet and a fluid inlet that are both oriented on a side portion of a flush body. Other embodiments may include a delivery catheter outlet oriented on a side portion of a flush body and a fluid inlet oriented on a distal face of the flush body, for example.

The opening 344 can be disposed at a proximal end of the flush body 333, as shown. In other embodiments, the opening can be disposed at the side portion 341 or the distal face 339 of the flush body 333.

The fluid inlet 337 may be configured to allow the introduction of a fluid into an interior space 343 within the flush body 333. As shown, a valve 334 may be positioned within and/or above the fluid inlet 337. The valve 334 may be configured to check fluid flow across the valve, such as by preventing the introduction and/or release of fluid into or from the interior space 343. For example, the valve 334 can be a Luer activated valve configured to check fluid flow until mechanically opened with a Luer standard connection and/or device (e.g., a Luer connection associated with tubing and/or other fluid delivery line).

The grommet 316 can be configured to be in fluid communication with the interior space 343, such that fluid introduced into the interior space 343 can move from the interior space 343 into the interior lumen 336 of the grommet 316. Fluid within the interior lumen 336 can then be introduced into the delivery catheter 302 for delivery, for example, to a tissue treatment site (e.g., at or near the location of an attached implantable device coupled to the distal end of the delivery catheter 302). For example, in some embodiments, the grommet 316 can include one or more holes (not shown) allowing fluid to pass from the interior space 343 into the interior lumen 336. Additionally, or alternatively, the grommet 336 can be formed (or partially formed) of a fluid-permeable substance that allows fluid transfer across the grommet 336.

As shown in the illustrated embodiment, the fluid management system 308 can include an outlet seal 338 disposed at or near the delivery catheter outlet 335. The outlet seal 338 can be configured to prevent the passage of fluid from the interior space 343 through the delivery catheter outlet 335 without being passed through the delivery catheter 302.

As shown, the outlet seal 338 can be positioned between the interior portion of the distal face 339 and the grommet 316. In the illustrated embodiment, the outlet seal 338 is formed as an O-ring positioned around the delivery catheter 302. Other embodiments can include other sealing means, such as one or more gaskets, plugs, stoppers, and/or caulked or other filled-in areas.

FIG. 40 illustrates that the fluid management system 308 can include additional structures for preventing unwanted passage of fluid through the delivery catheter outlet 335. In the illustrated embodiment, the outlet seal 338 is positioned within an outlet seal cavity defined by a rim 349. The rim 349 can, for example, position the outlet seal 338 in the proper orientation relative to the grommet 316, the delivery catheter 302, and/or the delivery catheter outlet 335 to ensure the integrity of the resulting fluid seal. The rim 349 can extend from the interior side of the distal face 339 to the grommet 316, thereby forming an additional barrier that can separate the outlet seal 338 from fluid contained in the interior space 343.

As illustrated, the grommet 316 can include a lip 345 extending to the interior wall of the flush body 333. The lip 345 can be positioned so as to separate a portion of the interior space 343 that is in fluid communication with the fluid inlet 337 from a portion closer to the distal face 339 of the flush body 333. Such a configuration can, for example, provide a barrier (e.g., in addition to a barrier provided by the outlet seal 338 and/or rim 349) between fluid within the interior space 343 and the delivery catheter outlet 335.

The illustrated embodiment can include an insert 347 disposed at the opening 344 of the flush body 333. The insert 347 may extend through the opening 344 to the grommet 316 and/or may be configured to engage with the grommet 316 (e.g., by coupling to the grommet 316 via matching push fit structures, threads, tabs, and/or other coupling means). As shown, the insert 347 can include an opening seal 346 configured to prevent the passage of fluid from the interior space 343 out through the opening 344. The opening seal 346 can be positioned within a slot formed in the exterior of the insert 347. The opening seal 346 can be formed as an O-ring, as in the illustrated embodiment. Other embodiments can include other sealing means, such as one or more gaskets, plugs, stoppers, and/or caulked or otherwise filled-in areas.

As illustrated, the fluid management system 308 can include a core 348 disposed at least partially within the interior lumen 336 of the grommet 316. The core 348 can extend through the insert 347 and into the interior lumen 336 of the grommet 316. The core 348 can be configured to receive various components of the delivery device 300 (e.g., one or more gripper lines, lock lines, and/or actuator rods) passing through the fluid management system 308 to gather and/or direct the components toward the delivery catheter 302. For example, the core 348 can include one or more interior lumens configured to receive one or more components of the delivery device 300 and direct it/them into the interior lumen 336 and toward the delivery catheter 302.

The illustrated embodiment can include a diaphragm 350 positioned proximal to the core 348 and/or insert 347. The diaphragm 350 can be configured to allow passage of various components (e.g., one or more gripper lines, lock lines, and/or actuator rods) into the interior of the flush body 333 (e.g., into the core 348 and/or into coinciding lumens within the core 348). The diaphragm 350 can be configured to form a fluid seal separating fluid on a distal side of the diaphragm 350 (e.g., fluid within the grommet 316 and/or core 348) from areas on a proximal side of the diaphragm 350, such as manifold 352 described below.

The manifold 352 can be positioned proximal to the diaphragm 350 and the proximal opening 344 (e.g., such that it is exterior to the flush body 333). The manifold 352 can be configured to receive various components (e.g., one or more gripper lines, lock lines, and/or actuator rods) at a manifold opening 354 and direct the components toward the diaphragm 350 and/or interior space 343. As shown in the illustrated embodiment, the manifold can include an inner cavity 356 extending from the manifold opening 354 a distance toward the diaphragm 350. One or more conduits 358 can extend between the inner cavity 356 and the diaphragm 350. Each of the one or more conduits 358 can be configured to receive a gripper line, lock line, actuator rod, etc. and direct it/them toward a receiving portion of the diaphragm 350.

The core 348, insert 347, and/or manifold 352 can be configured as a conducting assembly. For example, the core 348, insert 347, and/or manifold 352 (independently, as a pair, or in conjunction) can be configured to gather one or more components of the delivery device 300 (e.g., gripper line, lock line, actuator rod) and direct it/them into the interior lumen 336 of the grommet 316. In some embodiments, the conducting assembly can include one or more lumens configured to receive the one or more components of the delivery device 300. In some embodiments, the conducting assembly can be disposed at and/or through the opening 344 of the flush body 333.

The illustrated embodiment includes various adjoining and/or coupled components which are formed separately. In other embodiments, coupled and/or adjoining components may be integrally formed as one component. For example, in some embodiments, a grommet 316, an insert 347, a core 348, and/or a diaphragm 350 may be formed as one integral piece. In some embodiments, one or more of the components of a conducting assembly can be formed as one integral piece.

Embodiments of a fluid management system according to the present disclosure can provide a number of benefits. For example, the configuration of the flush body 333 relative to the diaphragm 350, insert 347, core 348, grommet 316, and/or delivery catheter 302 can eliminate the need for a large fluid reservoir (e.g., a fluid reservoir extending into the shell 306 or other components of the delivery device 300 located proximal to the fluid management system 308). Relative to configurations requiring a large fluid reservoir, embodiments of the present disclosure can minimize the area to be fluidly sealed from the remainder of the device and/or minimize the amount of fluid required to be held within the device at a given time. Accordingly, with less area to be sealed and/or less fluid present, the risk of leaks, spills, and/or associated equipment failure resulting from unwanted fluid transport can be beneficially reduced.

In addition, at least some of the fluid management system embodiments of the present disclosure can eliminate the need for a visual fluid reservoir (e.g., one including and/or requiring viewing windows to monitor fluid levels) located on and/or within the delivery device. For example, a fluid management system according to the present disclosure can allow a fluid reservoir and/or fluid monitoring system to be decoupled from the delivery device (e.g., detached from the delivery device and fluidly connected to the fluid management system via one or more tubes, lines, etc.).

Figure 41:
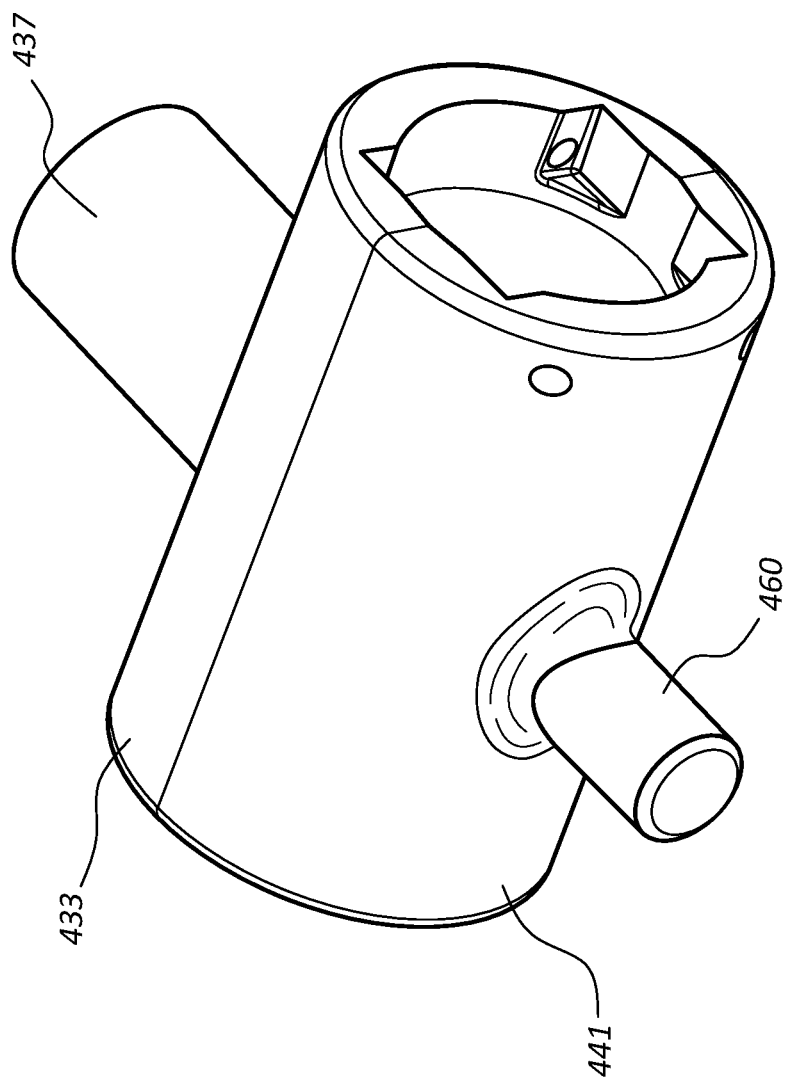

FIG. 41 illustrates another embodiment of a flush body 433 including a fluid inlet 437, a side portion 441, and a position indicator 460. The position indicator 460 can be configured to extend through a housing positioned over a portion of the delivery device 300 (see, e.g., FIG. 61), allowing a user to gauge the position of the delivery device 300 relative to the housing. As shown in FIG. 41, the position indicator 460 can extend from the side portion 441. The position indicator 460 may be positioned on the side portion 441 at a location opposite the fluid inlet 437, as illustrated. In other embodiments, the position indicator 460 and the fluid inlet 437 may be offset by 30, 60, 90, 120, or 150 degrees, for example. The position indicator 460 and the fluid inlet 437 may be circumferentially aligned, as illustrated. In other embodiments, the position indicator 460 and the fluid inlet 437 may be offset, such that one or the other is disposed closer to a proximal end or a distal end.

E. Gripper line Control

Embodiments of the present disclosure can include one or more control line assemblies for managing one or more control lines (e.g., gripper lines 90 and/or lock lines 92). As described in more detail below, a line assembly can be configured as a gripper line assembly or a lock line assembly.

Figure 42:
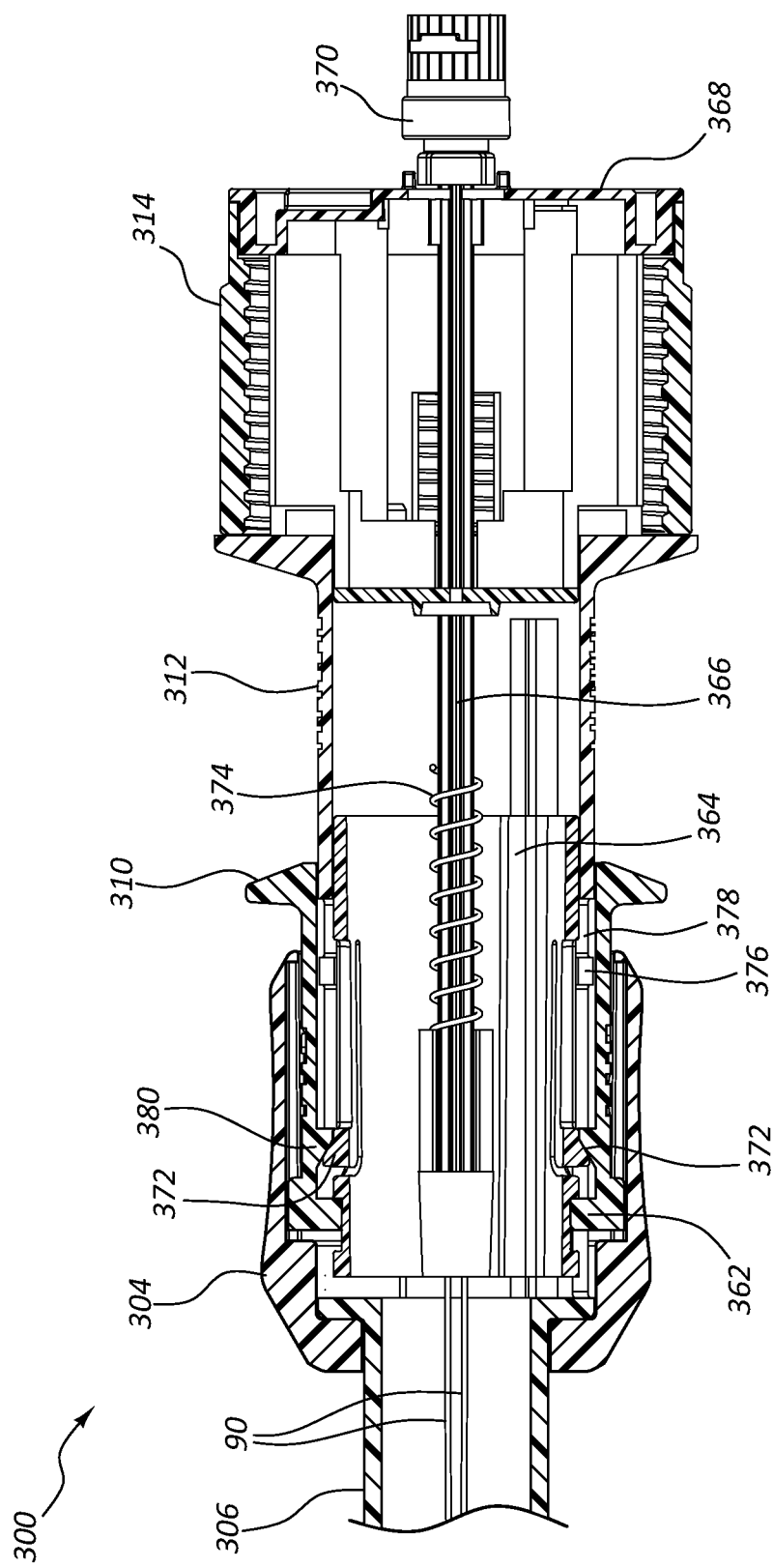
FIGS. 42-43 illustrate various components of a gripper line management system according to the present disclosure.
Figure 43:
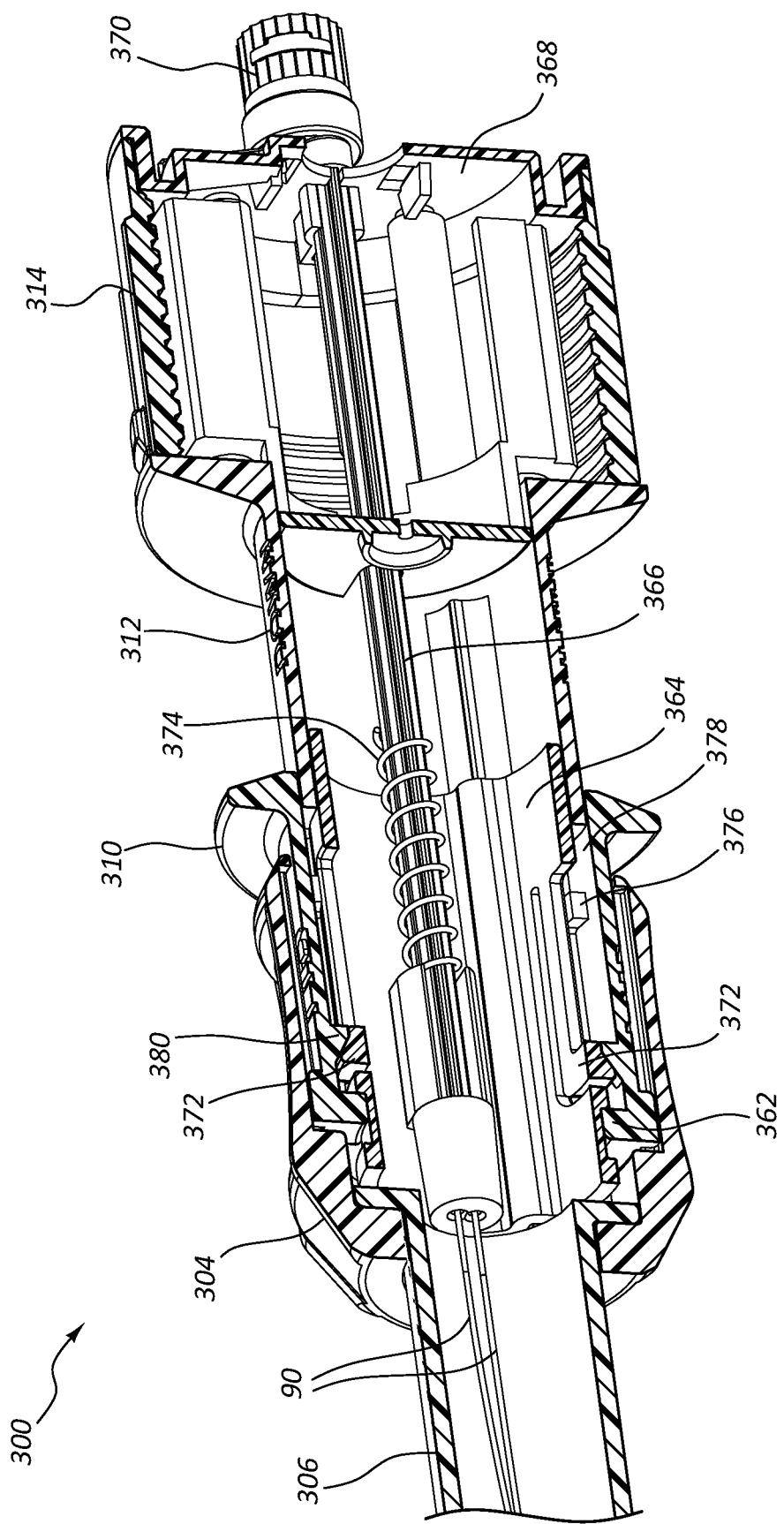
Figure 46:
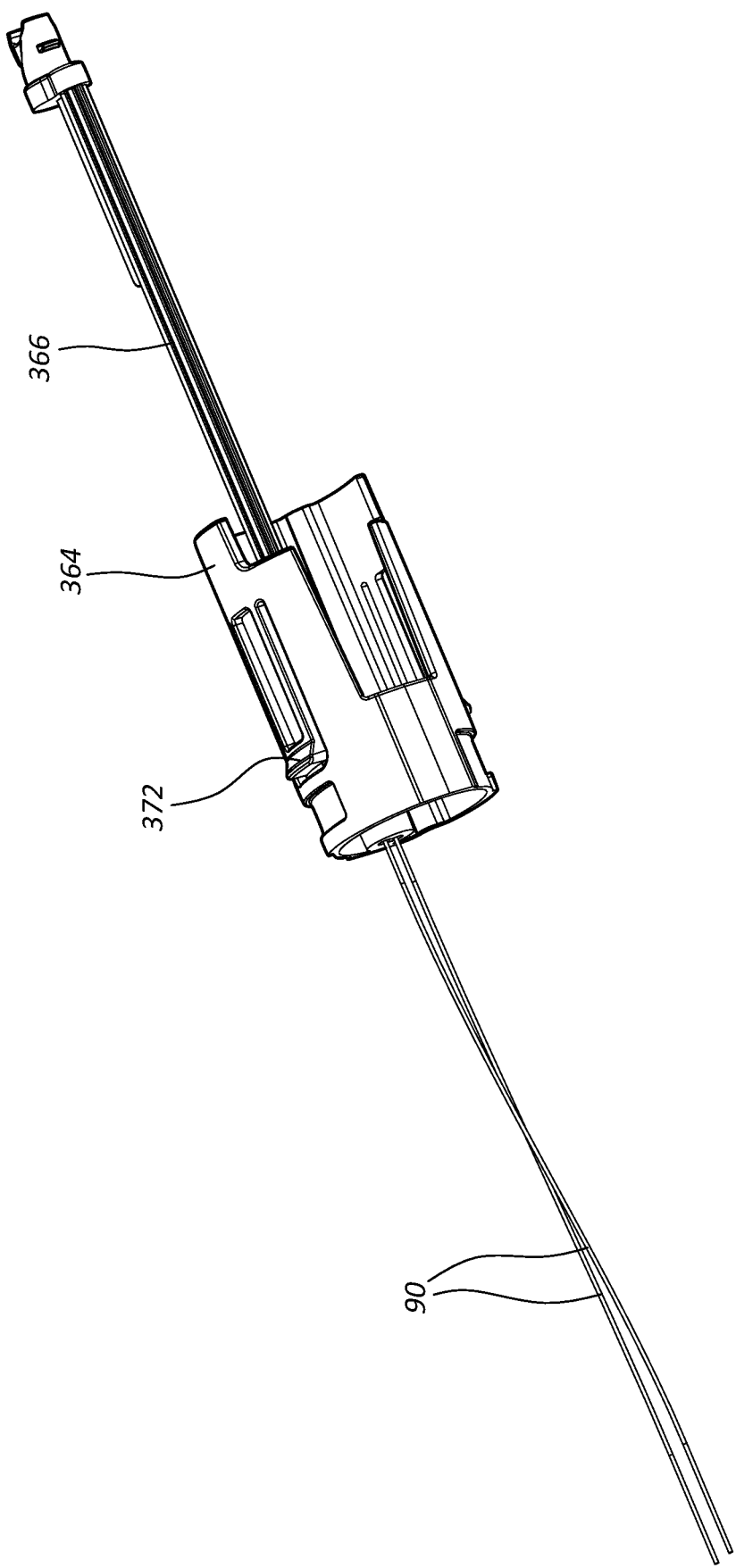
FIG. 46 illustrates gripper lines attached to a gripper line shuttle.

FIGS. 42-43 illustrate an embodiment of a line assembly useful for managing one or more gripper lines. FIGS. 42-43 show a cutaway view of a first side of the delivery device 300 shown in FIG. 32, showing the shell 306, collar 310, shaft 312, translation knob 304, and a portion of the deployment handle 314. As illustrated, the delivery device 300 can include a shuttle 364 slidably disposed within the shaft 312. The shuttle 364 can be coupled to a gripper line hub 366 that extends proximally from the shuttle 364 through the shaft 312 and through a housing lid 368. FIG. 46 illustrates the shuttle 364, gripper line hub 366, and gripper line 90, with other components of the delivery device removed for clarity. As shown, and as described in more detail below, the shuttle 364 can include one or more tabs 372.

Referring to FIGS. 42-43, a gripper line cap 370 may be coupled to the proximal end of the gripper line hub 366. As shown, the ends of a gripper line 90 (or in alternative embodiments, more than one gripper line) may be passed through the gripper line hub 366 before terminating at the gripper line cap 370. The gripper line cap 370 can be configured to secure the gripper line 90. For example, the gripper line cap 370 can be formed as a threaded cap configured to mate with matching threads on the gripper line hub 366. In such embodiments, the terminating portions of the gripper line 90 can be secured between the gripper line hub 366 and the gripper line cap 370.

In some embodiments, at least a portion of the gripper line 90 can be housed in a gripper line sheath. For example, one or more gripper line sheaths can be positioned over the gripper line 90 at the portion of the gripper line 90 secured by the threads of the gripper line cap 370. The one or more sheaths can be attached to the gripper line at desired locations, such as by using an adhesive and/or overmolding the sheaths. The one or more sheaths may be formed of a polymer material providing anti-slippage and/or greater attachment strength when the gripper line 90 is coupled to the gripper line cap 370. In some embodiments, one or more gripper line sheaths may also be attached at other portions of the gripper line 90, such as at or near areas of the gripper line 90 contacting the shuttle 364 and/or other components of the delivery device 300.

The gripper line 90 may be manipulated by actuation of the collar 310. As shown in the illustrated embodiment, the collar 310 can be configured to be translatable along the shaft 312. Translation of the collar 310 upon the shaft 312 can cause the shuttle 364 to translate within the shaft 312, thereby applying or releasing tension to the gripper line 90. For example, the embodiment illustrated in FIGS. 42-43 shows the collar 310 and shuttle 364 in a "down" configuration. In this configuration, the shuttle 364 is positioned distally within the shaft 312.

From the illustrated configuration, the collar 310 can be actuated so as to translate upon the shaft 312 (e.g., distally and/or proximally). As shown, the collar 310 can include an outer flange extending radially outward at an angle transverse to the longitudinal axis of the collar and configured to provide a gripping area for actuating the collar 310. Proximal movement of the collar 310 can cause an inner flange 362 of the collar 310 to engage with one or more tabs 372 formed in and/or extending outward from the shuttle 364. Engagement of the inner flange 362 against the one or more tabs 372 can thereby cause the shuttle 364 to translate with the collar 310. For example, as the inner flange 362 engages against the tabs 372, further proximal movement of the collar 310 along the shaft 312 will coincide with proximal movement of the shuttle 364 within the shaft 312.

As shown, proximal movement of the collar 310 can move the shuttle 364 until the tabs 372 reach one or more stops 376 disposed within a sidewall and/or formed as part of a sidewall of the shaft 312. Further proximal movement of the shuttle 364 (e.g., via further proximal movement of the collar 310) can cause the tabs 372 to flex inwardly, allowing the tabs 372 to move proximally past the stops 376. Upon moving proximally past the stops 376, the tabs 372 can flex outwardly back toward a relaxed configuration, allowing the tabs 372 to extend into tab slots 378 disposed in the sidewall of the shaft 312. Thus, as shown, the tabs 372 can be configured to flex outwardly into the tab slots 378 when positioned adjacent to the tab slots 378.

As illustrated, the tabs 372 can be formed with an angled and/or tapered surface (e.g., tapering from a larger width to a smaller width along a proximal direction), allowing the shuttle 364 to move proximally past the stops 376 but preventing the shuttle 364 from moving distally backwards after the tabs 372 have extended into the tab slots 378.

In other embodiments, additional and/or alternative securing means may be included, such as clamps, catches, stops, detents, and the like. In some embodiments, a plurality of lock tabs may be included. In some embodiments, one or more lock tabs may be configured as a hook, plug, insert, press-fit element, or other structure capable of lodging within and/or fastening against a lock slot. In some embodiments, one or more lock slots may be configured as a hole, aperture, receiving cavity, press-fit element, or other structure capable of lodging within and/or fastening against a lock tab. In some embodiments, a lock tab and/or lock slot can include magnetic properties so as to form a magnetic coupling for holding the lock tab against and/or within the lock slot.

In this configuration, the collar 310 and shuttle 364 can be in an "up" configuration. In such a configuration, the shuttle 364 can be positioned proximally within the shaft 312. Positioning of the shuttle 364 in a proximal position can cause the gripper line 90 to be moved proximally. Such proximal movement of the gripper line may adjust an implantable device associated with and/or attached to the gripper line. For example, proximal movement of the gripper line 90 may raise gripper elements of an implantable device attached to the distal end of the delivery catheter, as described above.

Referring back to FIG. 32, the shaft 312 and/or collar 310 can include one or more gripper position indicators 382. The embodiment illustrated in FIG. 32 shows, for example, that the shaft can provide an indication to a user that the gripper line is in a distal and/or down configuration when the position indicator 382 is visible. Additionally, or alternatively, the collar 310 can include one or more position indicators (not shown). For example, the collar 310 can include one or more position indicators that are only visible when the collar 310 has been moved proximally into an open configuration. The collar 310 can thereby indicate to a user that the gripper line is in a proximal and/or up configuration when a position indicator located on the collar 310 is visible and/or when the gripper position indicator(s) 382 of the shaft 312 have been covered by the collar 310.

As illustrated in FIGS. 42-43, the collar 310 can include an interior projection 380. The interior projection 380 can be configured to engage with the tabs 372 and/or press the tabs 372 inwards. As shown, when the collar 310 is moved distally, an angled surface of the interior projection 380 can press against the tabs 372 and force the tabs 372 inwards. For example, when the shuttle 364 and collar 310 are in an up configuration, the collar 310 may be moved distally. Distal movement of the collar 310 can allow the interior projection 380 to press against the tabs 372, moving the tabs 372 out of their respective tab slots 378. As the tabs 372 are removed from the tab slots 378, the shuttle 364 can be further moved distally (e.g., to the down configuration).

The delivery device 300 can include a shuttle return spring 374 configured to apply a force for positioning and/or maintaining the shuttle 364 toward a default position within the shaft 312 (e.g., toward the down configuration as in the illustrated embodiment). For example, upon releasing the tabs 372 from the tab slots 378 so as to allow the shuttle 364 to be moved distally from the up configuration toward the down configuration, the shuttle return spring 374 can expand to push the shuttle 364 distally toward the down configuration. As shown, the shuttle return spring 374 can be positioned around the gripper line hub 366. In other embodiments, one or more coil springs, leaf springs, and/or other resilient members may be included at other locations in order to push and/or pull a shuttle into a default position.

F. Lock Line Control

Figure 44:
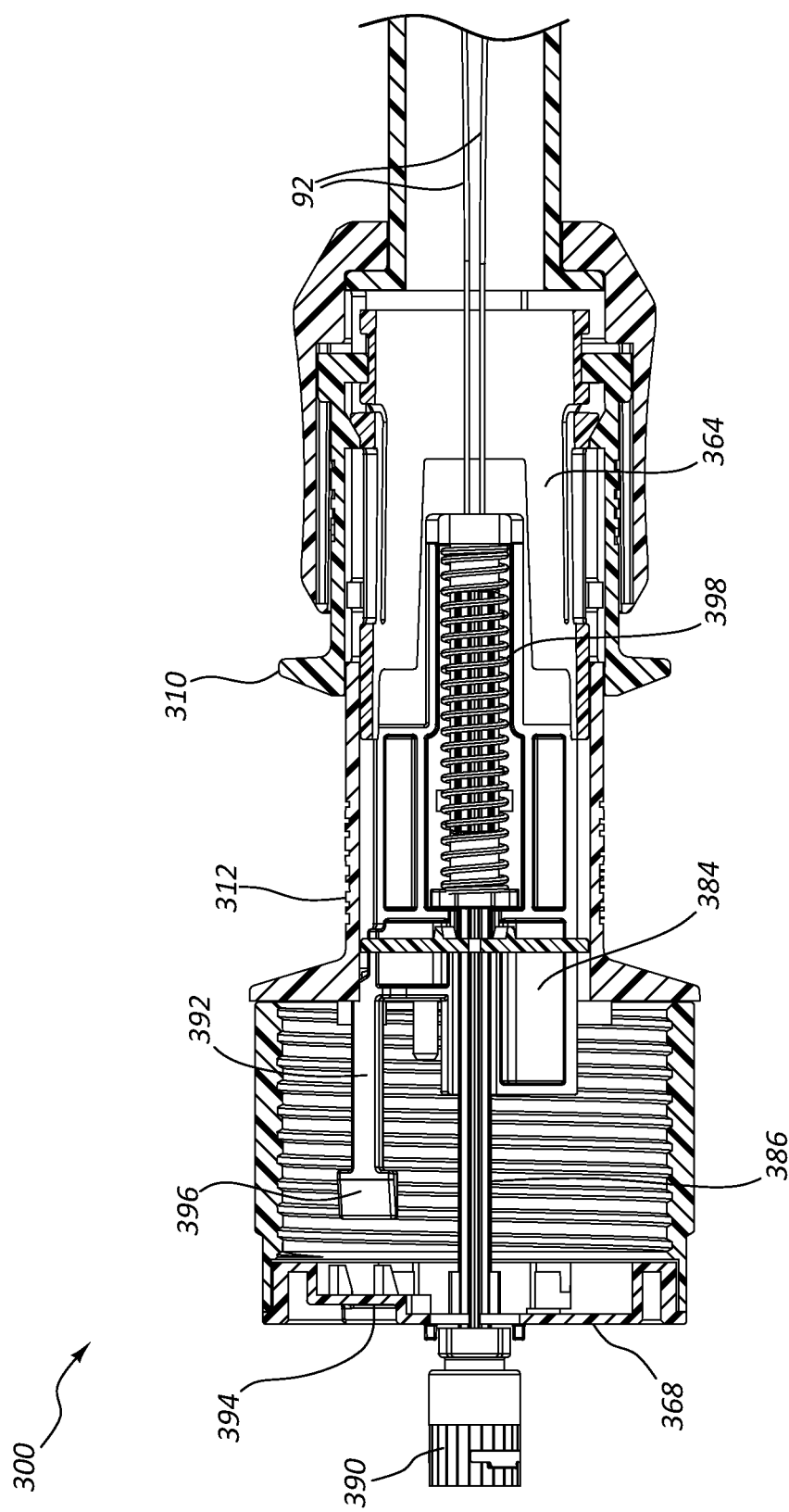
FIGS. 44-45 illustrate various components of a lock line management system according to the present disclosure.
Figure 45:
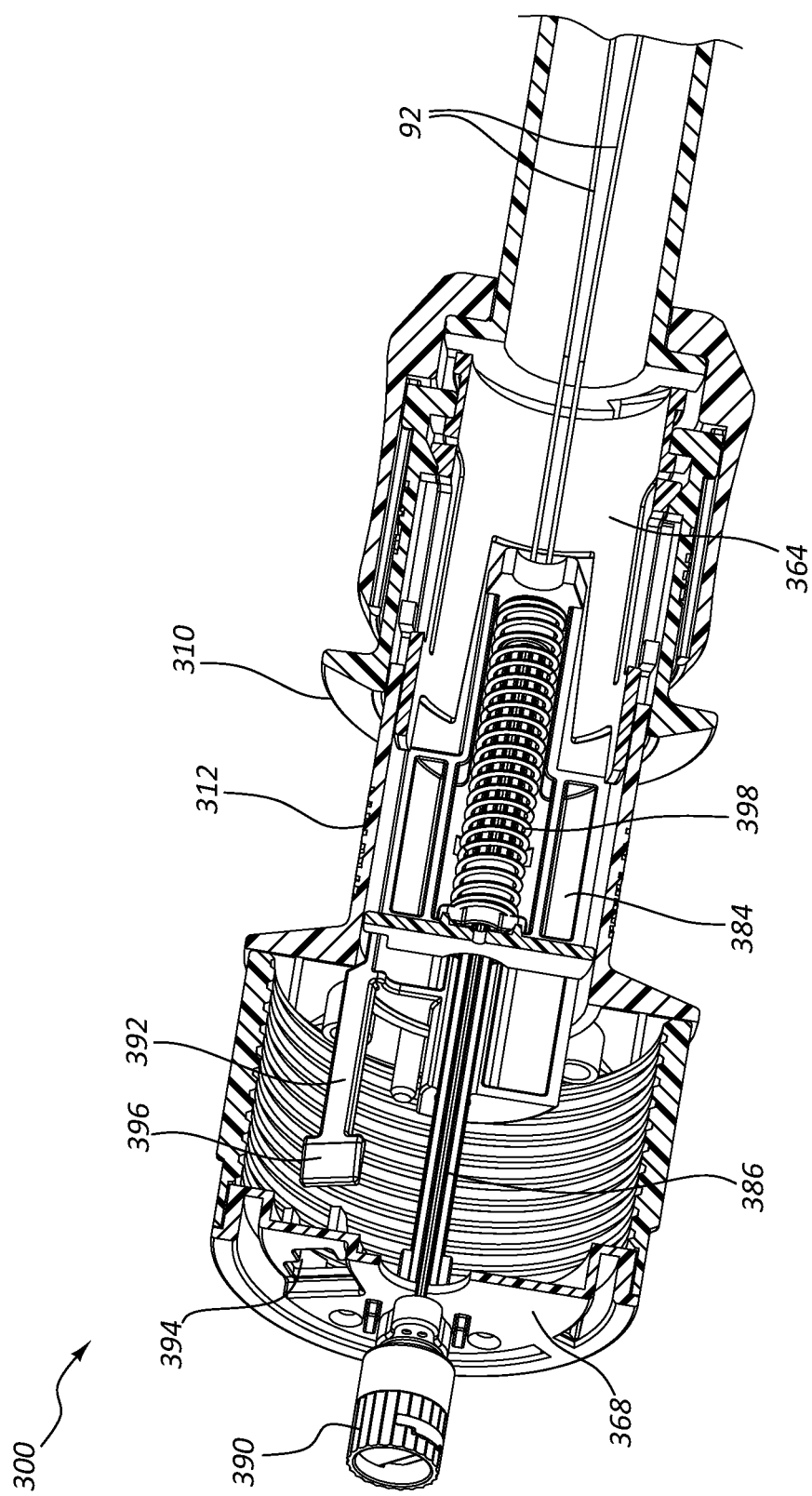

FIGS. 44-45 illustrate an embodiment of a line assembly useful for managing one or more lock lines. FIGS. 44-45 show a cutaway view of a second side of the delivery device 300 shown in FIG. 32. As illustrated, delivery device 300 can include a carriage 384 slidably disposed within the shaft 312. The carriage 384 may be positioned proximal to the shuttle 364. As shown, the carriage 384 may be configured in size and shape to engage with the shuttle 364, such that when the shuttle 364 is moved proximally, the shuttle 364 abuts against and translates the carriage 384 proximally and/or such that when the carriage 384 is moved distally, the carriage 384 abuts against and translates the shuttle 364 distally.

The illustrated carriage 384 can be coupled to a lock line hub 386 that extends proximally from the carriage 384 through the housing lid 368. A lock line 92 may be coupled to the proximal end of the lock line hub 386. As shown, a lock line 92 (or in alternative embodiments, more than one lock line) may be passed through the lock line hub 386 before terminating at the lock line cap 390. The lock line cap 390 can be configured to secure the lock line 92. For example, the lock line cap 390 can be formed as a threaded cap configured to mate with matching threads on the lock line hub 386. In such embodiments, the terminating portions of the lock line 92 can be secured between the lock line hub 386 and the lock line cap 390.

In some embodiments, at least a portion of the lock line 92 can be housed in a lock line sheath. For example, one or more lock line sheaths can be positioned over the lock line 92 at the portion of the lock line 92 secured by the threads of the lock line cap 390. The one or more sheaths can be attached to the lock line at desired locations, such as by using an adhesive and/or overmolding the sheaths to the lock line 92. The one or more sheaths may be formed of a polymer material providing anti-slippage and/or greater attachment strength when the lock line 92 is coupled to the lock line cap 390. In some embodiments, one or more lock line sheaths may also be attached at other portions of the lock line 92, such as at or near areas of the lock line 92 contacting the carriage 384 and/or other components of the delivery device 300.

The lock line 92 may be manipulated by actuation of the collar 310. As described above, translation of the collar 310 upon the shaft 312 can cause the shuttle 364 to translate within the shaft 312. Proximal movement of the shuttle 364 can cause proximal movement of the carriage 384 (e.g., via mechanical communication between the shuttle 364 and the carriage 384), thereby applying or releasing tension to the lock line 92. Thus, in such embodiments, actuation of the gripper and/or gripper line 90 into the up configuration can also cause locking of an implantable device (e.g., via the locking mechanism 106 shown in FIGS. 28-31) attached to the delivery device 300.

The carriage 384 may include a lock tab 392. The lock tab 392 may be configured to be passable through a lock slot 394 disposed in the housing lid 368, as illustrated. The lock tab 392 and/or lock slot 394 can be configured such that the lock tab 392 can be lodged and/or otherwise held in position by the lock slot 394 after passing through the lock slot 394. For example, after the lock tab 392 has passed through the lock slot 394, the lock tab 392 can be positioned such that a flared portion 396 of the lock tab 392 resists and/or prevents the lock tab 392 from passing back through the lock slot 394. In the illustrated embodiment, the lock slot 394 includes a narrow width section (e.g., narrower than the section in which the lock tab 392 passes freely) that can provide this function. For example, the flared portion 396 of the lock tab 392 can prevent the lock tab 392 from passing through the lock slot 394 when the lock tab 392 is positioned in the narrow width section.

In other embodiments, additional and/or alternative securing means may be included, such as clamps, catches, stops, detents, and the like. In some embodiments, a plurality of lock tabs may be included. In some embodiments, one or more lock tabs may be configured as a hook, plug, insert, press-fit element, or other structure capable of lodging within and/or fastening against a lock slot. In some embodiments, one or more lock slots may be configured as a hole, aperture, receiving cavity, press-fit element, or other structure capable of lodging within and/or fastening against a lock tab. In some embodiments, a lock tab and/or lock slot can include magnetic properties so as to form a magnetic coupling for holding the lock tab against and/or within the lock slot.

As shown, the lock tab 392 may be configured in size and shape so as to extend through the housing lid 368 when the carriage 384 is positioned in a proximal-most position, and to not extend through the housing lid 368 when the carriage 384 is positioned in a distal-most position.

In the illustrated embodiment, the lock line assembly may be moved from a locked position into an unlocked position by manipulating the portion of the lock tab 392 extending proximally through the lock slot 394. For example, adjusting the lock tab 392 to allow the lock tab 392 to pass through the lock slot 394 (e.g., by positioning the flared portion 396 so as to fit through a wider portion of the lock slot 394) can allow the carriage 384 to be moved distally, thereby moving the lock line 92 distally (e.g., to unlock an attached implantable device). In some embodiments, the lock line assembly may be moved toward an unlocked configuration by dislodging the lock tab 392 from the lock slot 394.

The delivery device 300 can also include a carriage return spring 398 configured to apply a force for positioning the carriage 384 toward a default (e.g., toward the unlocked configuration). For example, upon adjusting the lock tab 392 so as to allow the carriage to be moved distally from the locked configuration toward the unlocked configuration, the carriage return spring 398 can expand to push the carriage 384 distally toward the unlocked configuration. As shown, the carriage return spring 398 can be positioned around the lock line hub 386. In other embodiments, one or more coil springs, leaf springs, and/or other resilient members may be included to push and/or pull a carriage into position.

F. Actuator Rod Control

Figure 47:
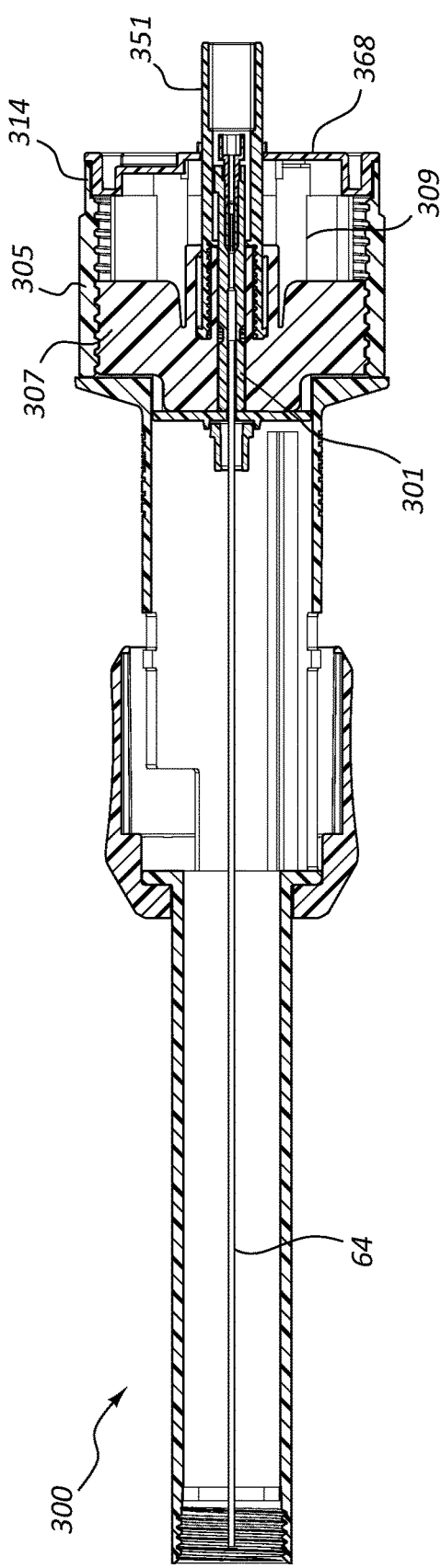
FIGS. 47-49 illustrate various components of an actuator assembly according to the present disclosure.

FIG. 47 illustrates a cutaway view of a first side of the delivery device 300 shown in FIG. 32, showing various components of an actuator rod control system disposed within the deployment handle 314. As illustrated, the delivery device 300 can include an actuator rod 64 that is coupled to a crimp 301 and that extends from the crimp 301 distally to the delivery catheter 302 (not shown). As shown in the illustrated embodiment, the crimp 301 can be secured within an actuator handle 351. The actuator handle 351 may extend through and beyond the housing lid 368. As shown, the actuator handle 351 may be coupled to a slider 307, the slider 307 having threads configured to match with internal threads of an actuator knob 305. In this configuration, rotation of the actuator knob 305 can cause the slider 307 to translate along the actuator knob 305 by action of the threading.

Rotation of the actuator knob 305 can extend or retract (depending on the direction of rotation) the actuator rod 64 in order to manipulate the distal elements 18 of the implantable device 14. Rotation of the slider 307 itself is prevented by a first end piece 309 that may be positioned adjacent to the slider 307. Because the crimp 301 can be coupled to the slider 307, the crimp 301 can translate along with the slider 307.

The actuator rod 64 may be rotated by rotation of the actuator handle 351. As illustrated, the actuator handle 351 may be coupled to the slider 305 by threading into the slider 305. In this configuration, rotation of the actuator handle 351 allows the actuator handle 351 to translate proximally away from the slider 305, thereby translating actuator rod 64 proximally. As described above, rotation of the actuator rod 64 can engage or disengage a threaded joiner 332 of the delivery catheter 302 from the threaded stud 74 of the implantable device 14 (e.g., to attach or detach the implantable device 14 from the delivery catheter 302). In addition, when the actuator rod 64 is in a disengaged state, the actuator rod 64 may optionally be retracted and optionally removed from the delivery device 300 by pulling the actuator handle 351 and withdrawing the actuator rod 64 from the delivery device 300 (e.g., after unthreading the actuator handle 351 from the slider 307).

Figure 48:
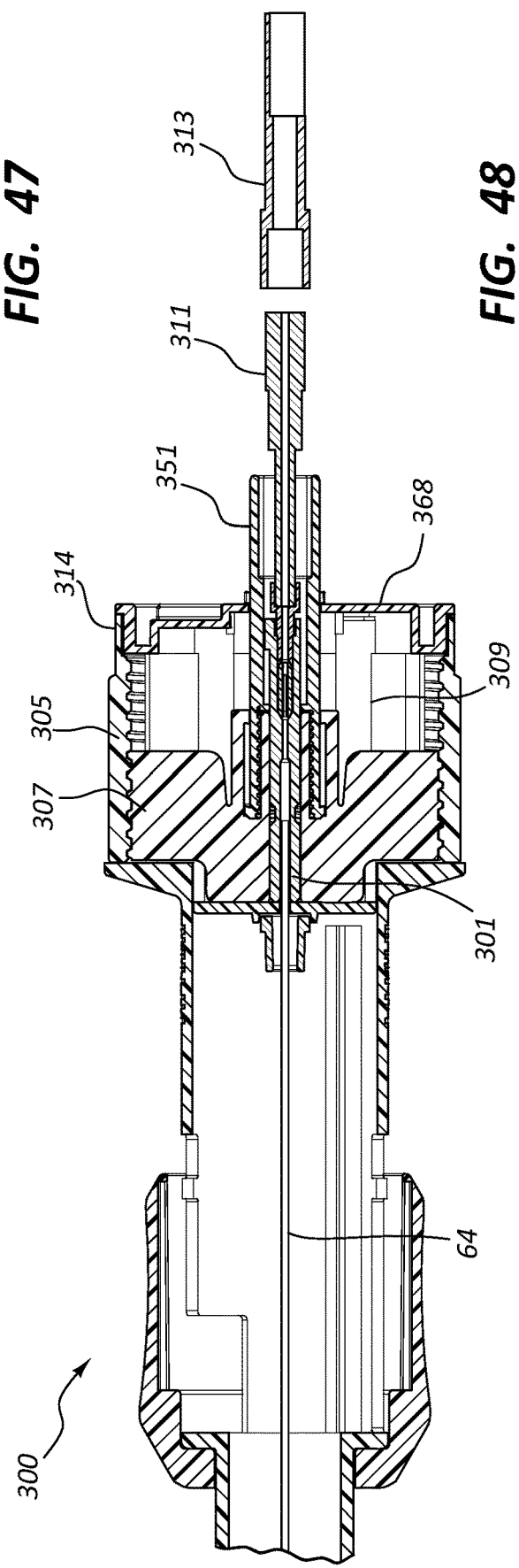

Some embodiments may include one or more removal tools configured to provide removal and/or adjustment of the actuator rod 64 and/or crimp 301. As illustrated in FIG. 48, for example, the crimp 301 may be configured to receive a first removal tool 311. The first removal tool 311 can optionally be coupled to a second removal tool 313. The first removal tool 311 and/or second removal tool 313 can be used to adjust and/or remove the crimp 301 from within the actuator handle 351.

Figure 49:
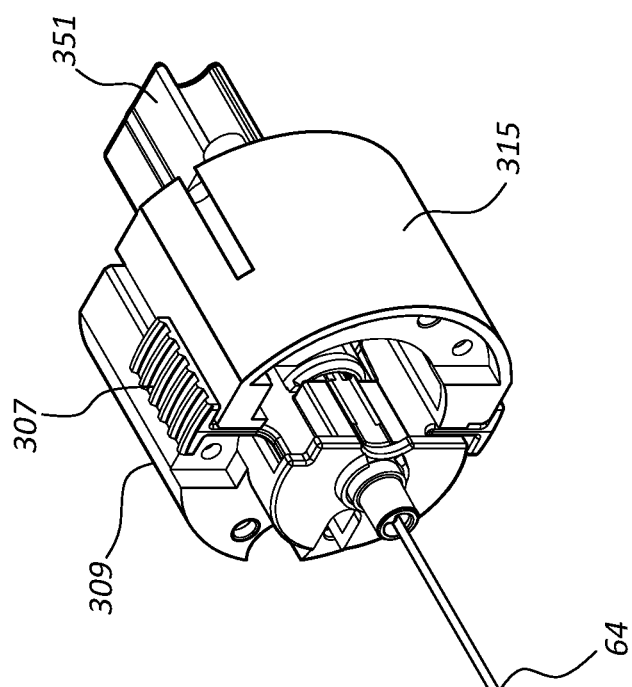

FIG. 49 illustrates the slider 307, first end piece 309, actuator handle 351, actuator rod 64, and a second end piece 315, with the actuator knob 305, shell 306, and other components removed for clarity. As illustrated, the first end piece 309 and/or second end piece 315 can be configured to prevent rotation of the slider 307, allowing the slider to translate distally or proximally upon engagement of the threaded portion of the slider 307 with the inner threads of the actuator knob.

G. Staged Deployment

Figure 50:
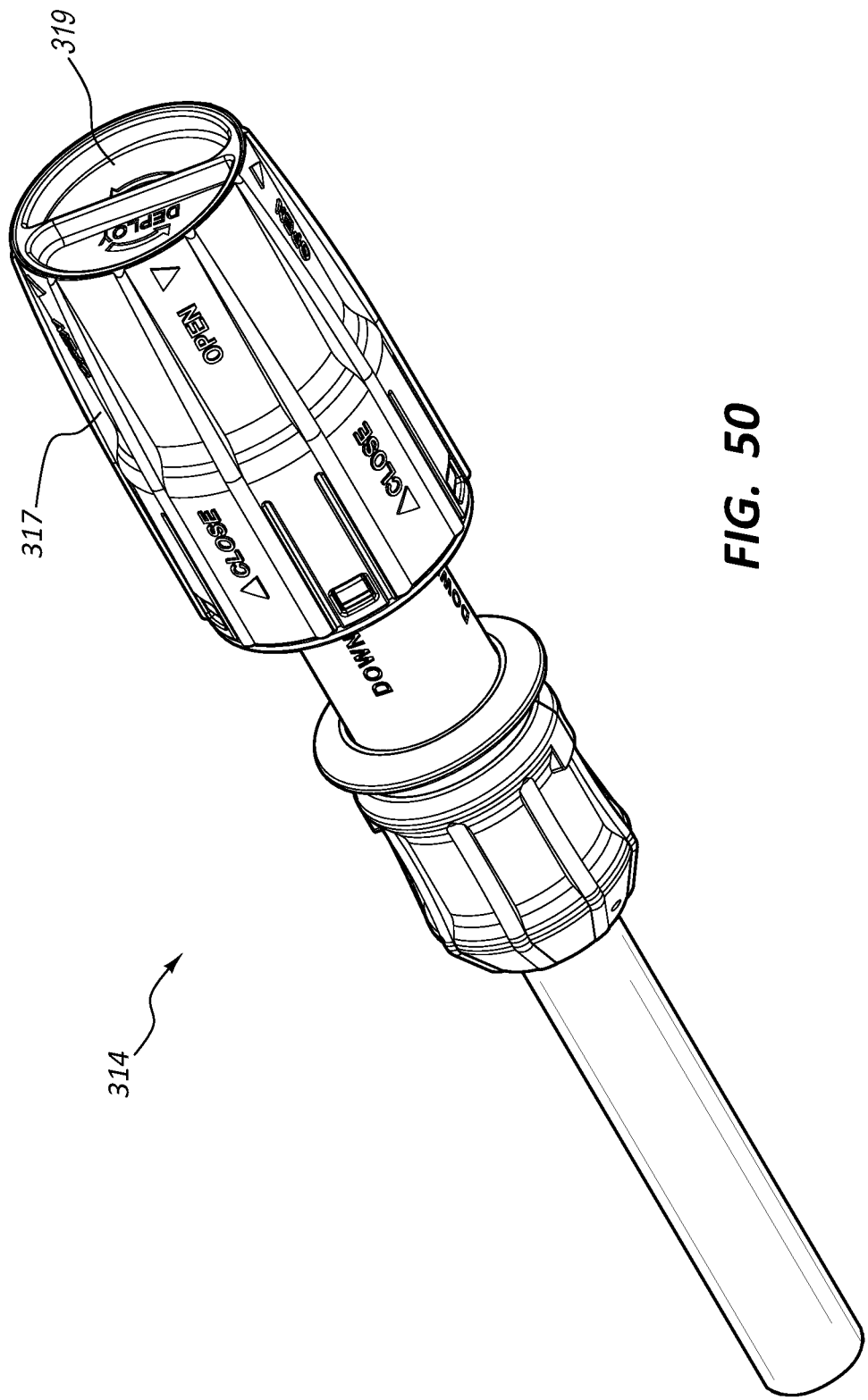
FIGS. 50-54 illustrate an embodiment of a deployment handle configured to provide staged deployment of a fixation device.
Figure 51:
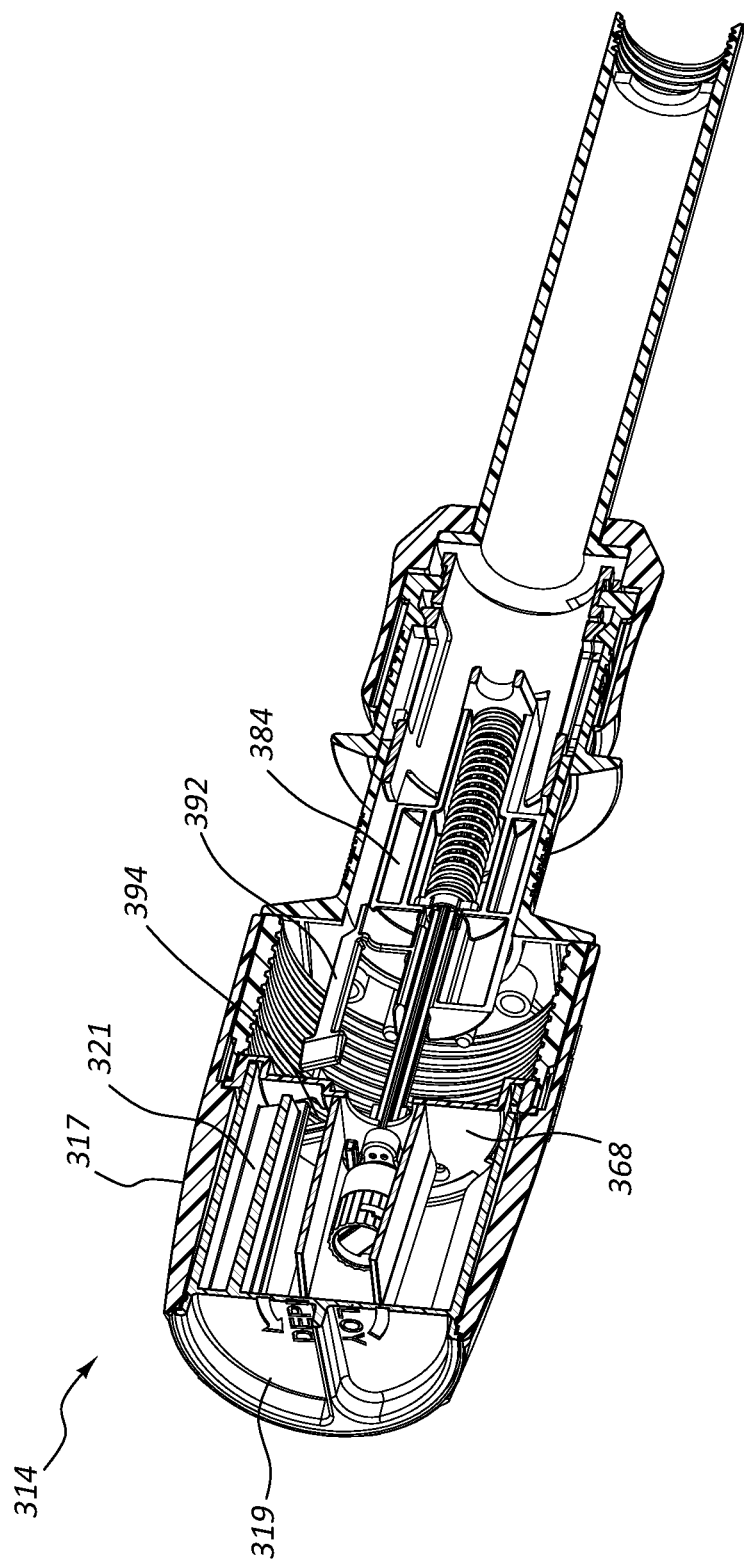

FIGS. 50-54 illustrate one embodiment of a deployment handle 314 and its components. As shown in FIG. 50, the deployment handle 314 can include an outer handle cap 317 and an inner handle cap 319. Rotation of the outer handle cap 317 can cause rotation of the underlying actuator knob 305, which, as described above, can cause the actuator rod 64 to translate distally and proximally in response (e.g., in order to open and close the distal elements 18 or the implantable device 14).

The illustrated embodiment of the deployment handle 314 can be configured to provide a staged deployment sequence. The staged deployment sequence can, for example, prevent accidental and/or incorrect deployment steps that could potentially disrupt or prolong a medical procedure and/or which could cause harm to a patient. For example, the deployment handle 314 can be configured so as to force and/or remind a user to perform certain deployment steps prior to other deployment steps. In some embodiments, for example, some steps will not be able to be performed without first removing and/or actuating one or more components of the deployment handle 314, with the removing and/or actuating ensuring that required and/or preferred prior steps are taken first.

For example, during a tissue repair procedure (e.g., mitral valve fixation), an operator may manipulate the distal elements 18 and/or the gripper 16 (shown, for example, in FIGS. 4-7 and 12-28) to grasp the targeted tissue, as described above. After obtaining a desired grasp of the target tissue, the user can then close the implantable device 14 (shown, for example, in FIGS. 4-7 and 12-28) by rotating the outer handle cap 317 so as to actuate the actuator knob 305 and cause the actuator rod (e.g., actuator rod 64) to translate, as described above. Upon determining a suitable grasp, the operator can begin a staged deployment process by actuating the inner handle cap 319. As illustrated in FIG. 50, the inner handle cap 319 can be accessed at the proximal end of the deployment handle 314. The inner handle cap 319 can be configured to rotate within the outer handle cap 317.

In the illustrated embodiment, actuation of the inner handle cap 319 causes the implantable device 14 to enter a locked configuration (e.g., as shown in FIG. 4). As shown in the cutaway view of FIG. 51, actuation of the inner handle cap 319, such as by rotating the inner handle cap 319 counterclockwise (as viewed from a perspective proximal to the deployment handle 314) causes an inner handle cap tab 321 to pass over the lock slot 394. This motion can ensure that the implantable device 14 is placed in a locked configuration. For example, if the carriage 384 is in an unlocked configuration with the lock tab 392 extending through the lock slot 394, actuation of the inner handle cap 319 can disengage the lock tab 392 from the lock slot 394, allowing the carriage 384 to translate distally to place the implantable device 14 in the locked configuration.

After the inner handle cap 319 has been actuated, the outer handle cap 317 and inner handle cap 319 can be removed from the deployment handle 314. In some embodiments, grooves, channels, stops, detents, and/or other structures can be included in the inner handle cap 319, the outer handle cap 317, and/or the housing lid 368 to prevent removal of the outer handle cap 317 and/or inner handle cap 319 until after the inner handle cap 319 has been actuated. For example, the inner handle cap 319 may include grooves that prevent the inner handle cap 319 from being detached from the housing lid 368 until the inner handle cap 319 has been rotated to an actuated position.

Figure 52:
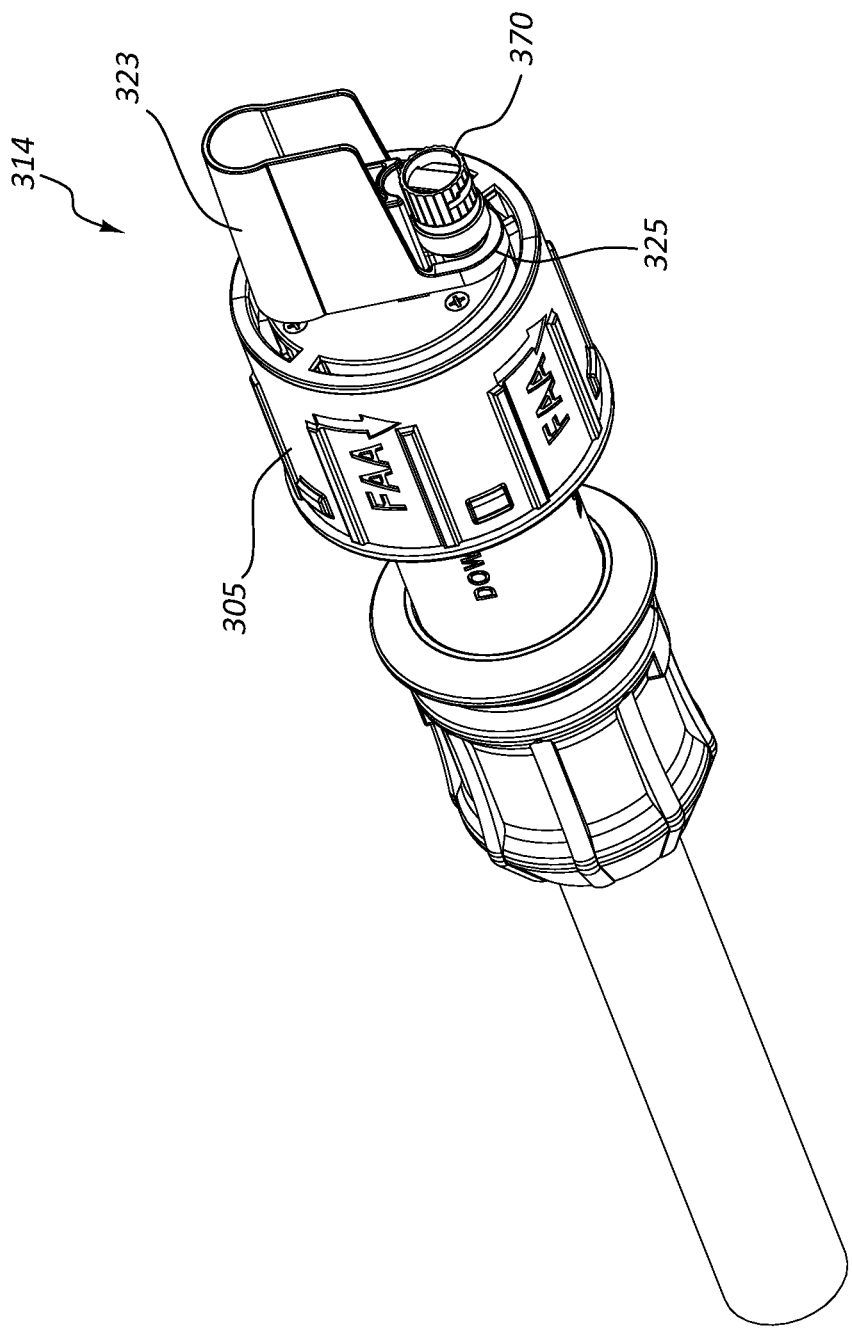

FIG. 52 illustrates the deployment handle 314 after the outer handle cap 317 and inner handle cap 319 have been removed. From this configuration, an operator can test rotation of the exposed actuator knob 305 in order to perform a final arm angle check (FAA check). For example, an operator can attempt to rotate the actuator knob 305 to open the distal elements 18 of the implantable device 14 as part of the FAA check. If the implantable device 14 has been properly placed in a locked configuration by the prior deployment steps, then the operator will be unable to or be limited in rotating the actuator knob 305. Additionally, or alternatively, an operator may use the actuator knob 305 to perform an FAA check at other times during deployment, such as after actuating the inner handle cap 319 but prior to removing the outer handle cap 317 and inner handle cap 319, and/or after removing the lock line 92, for example.

As shown, in FIG. 52, the deployment handle 314 can include a lockout 323 configured to prevent an operator from accessing the lock line cap 390 (hidden by the lockout 323 in FIG. 52) prior to performing steps associated with the gripper line cap 370. In this embodiment, the lockout 323 can prevent an operator from inadvertently and/or mistakenly accessing the lock line cap 390 and/or lock line 92 prior to performing preferred and/or required steps involving the gripper line 90 and/or gripper line cap 370. As shown, the lockout 323 can include a lockout lip 325 positioned underneath (i.e., distal to) the gripper line cap 370. This configuration can prevent the lockout 323 from being removed prior to removal of the gripper line cap 370. For example, the lockout lip 325 can be configured in size and shape so as to prevent movement of the lockout prior to removal of the first control line cap.

For example, from the configuration shown in FIG. 52, an operator can disengage the gripper line cap 370 to reveal the gripper line 90. The gripper line 90 can then be examined. For example, it may be preferred to perform a removability check to ensure that the gripper line 90 can be freely moved back and forth within the closed clip before proceeding with subsequent deployment steps, though the gripper line may not be completely removed at this point.

Figure 53:
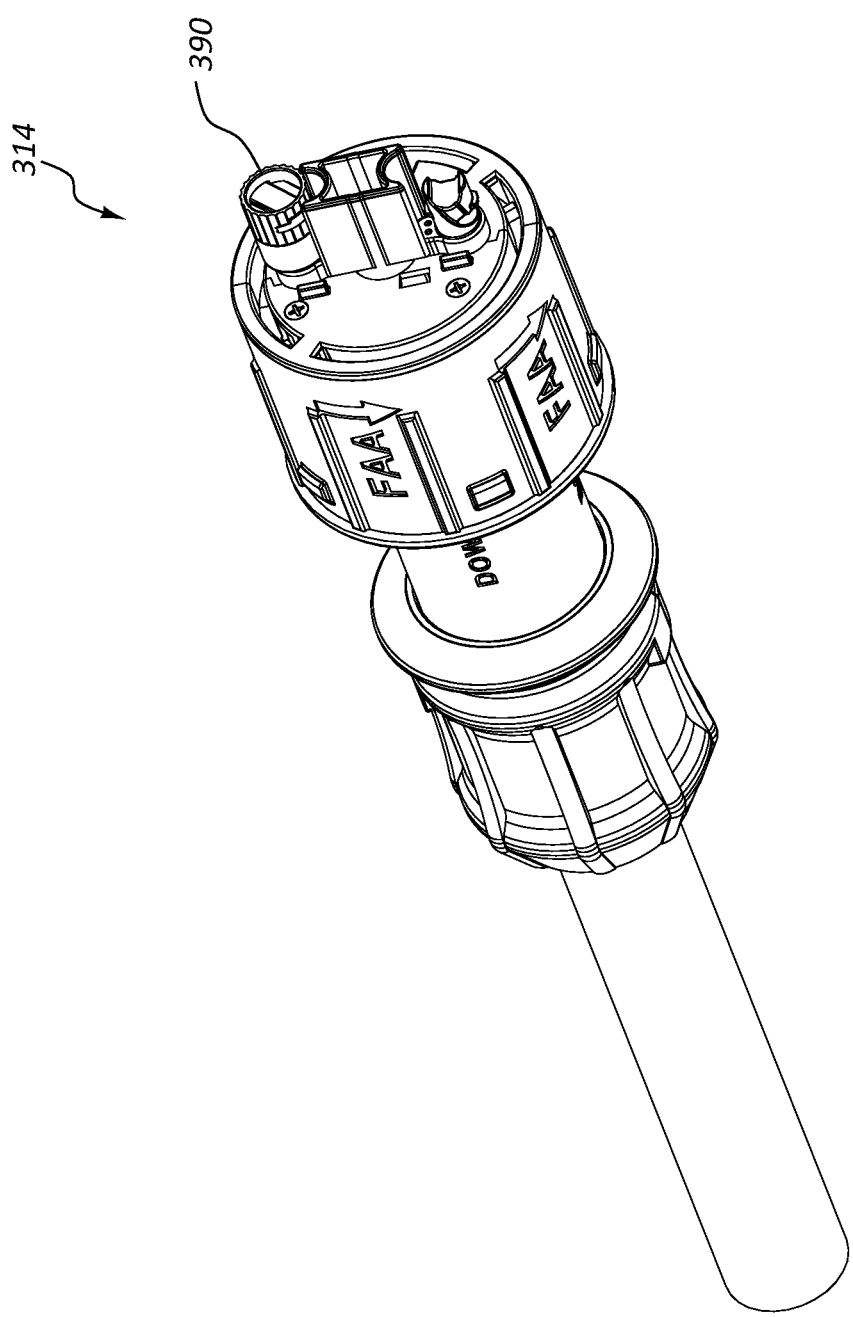

After the gripper line cap 370 has been removed, the lockout 323 may be removed to provide access to the lock line cap 390, as shown in FIG. 53. From this configuration, an operator may remove the lock line cap 390 to gain access to the lock line 92. An operator can remove the lock line 92 from the delivery device 300 by pulling the lock line 92 proximally out of the delivery device 300 (e.g., by pulling on one end and allowing the opposite end to follow through the delivery device 300).

Figure 54:
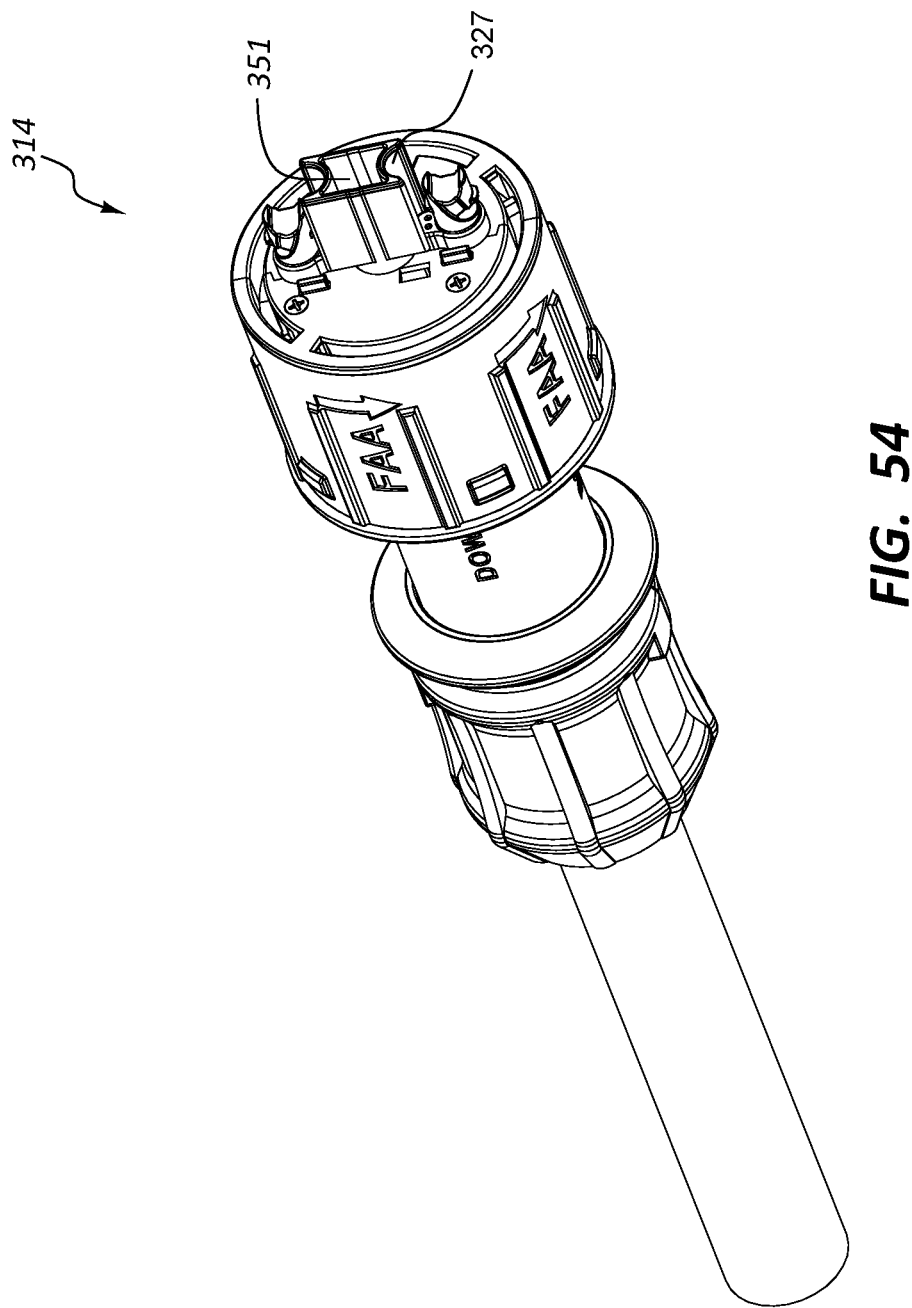

FIG. 54 illustrates the deployment handle 314 after the lock line cap 390 has been removed. From this configuration, an operator can actuate the actuator handle 351 (e.g., to decouple the implantable device 14 from the delivery catheter 302). As illustrated, the actuator handle 351 can have one or more indented portions 327 that prevent the actuator handle 351 from being rotated before the gripper line cap 370 and/or lock line cap 390 have been removed. For example, the indented portions 327 can be configured such that the gripper line cap 370 and/or lock line cap 390 fit or partially fit within the indented portions 327, preventing the actuator handle 351 from rotating past the gripper line cap 370 and/or lock line cap 390 until the gripper line cap 370 and/or lock line cap 390 have been removed. After disengagement of the implantable device 14, an operator may remove the gripper line 90 by pulling the gripper line proximally from the deployment handle 314 (e.g., as with removal of the lock line 92).

Figure 55:
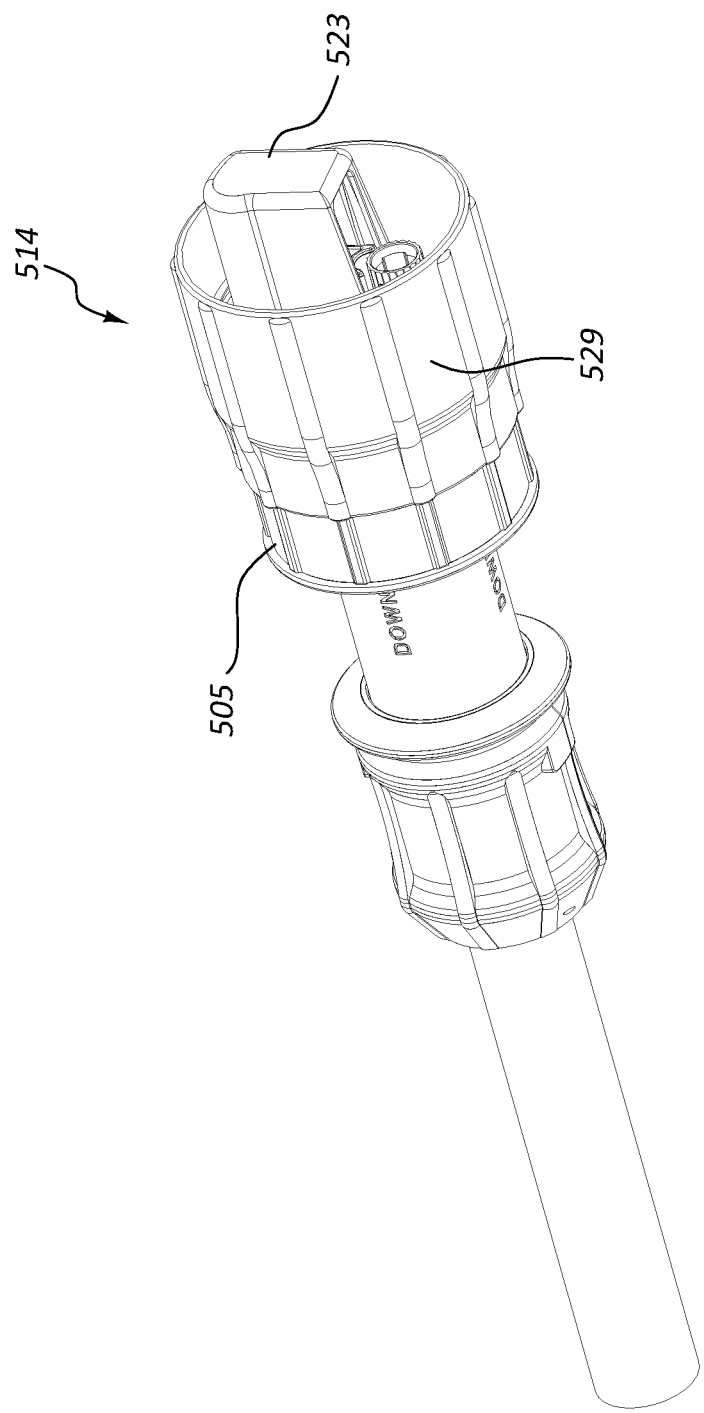
FIGS. 55-59 illustrate another embodiment of a deployment handle configured to provide staged deployment of a fixation device.

FIG. 55 illustrates another embodiment of a deployment handle 514 configured to provide staged deployment of an attached implantable device. As shown, the deployment handle 514 can include a telescopic cap 529 configured to slidably move along an actuator knob 505. For example, upon determining that the attached implantable device has a suitable grasp of targeted tissue, an operator can slide or otherwise position the telescopic cap 529 from a first (e.g., proximal) position at least partially preventing access to the housing lid (not shown), lockout 523, and other components of the deployment handle 514 into a second (e.g., distal) position providing access to the housing lid, lockout 523, and other components of the deployment handle 514.

Figure 56:
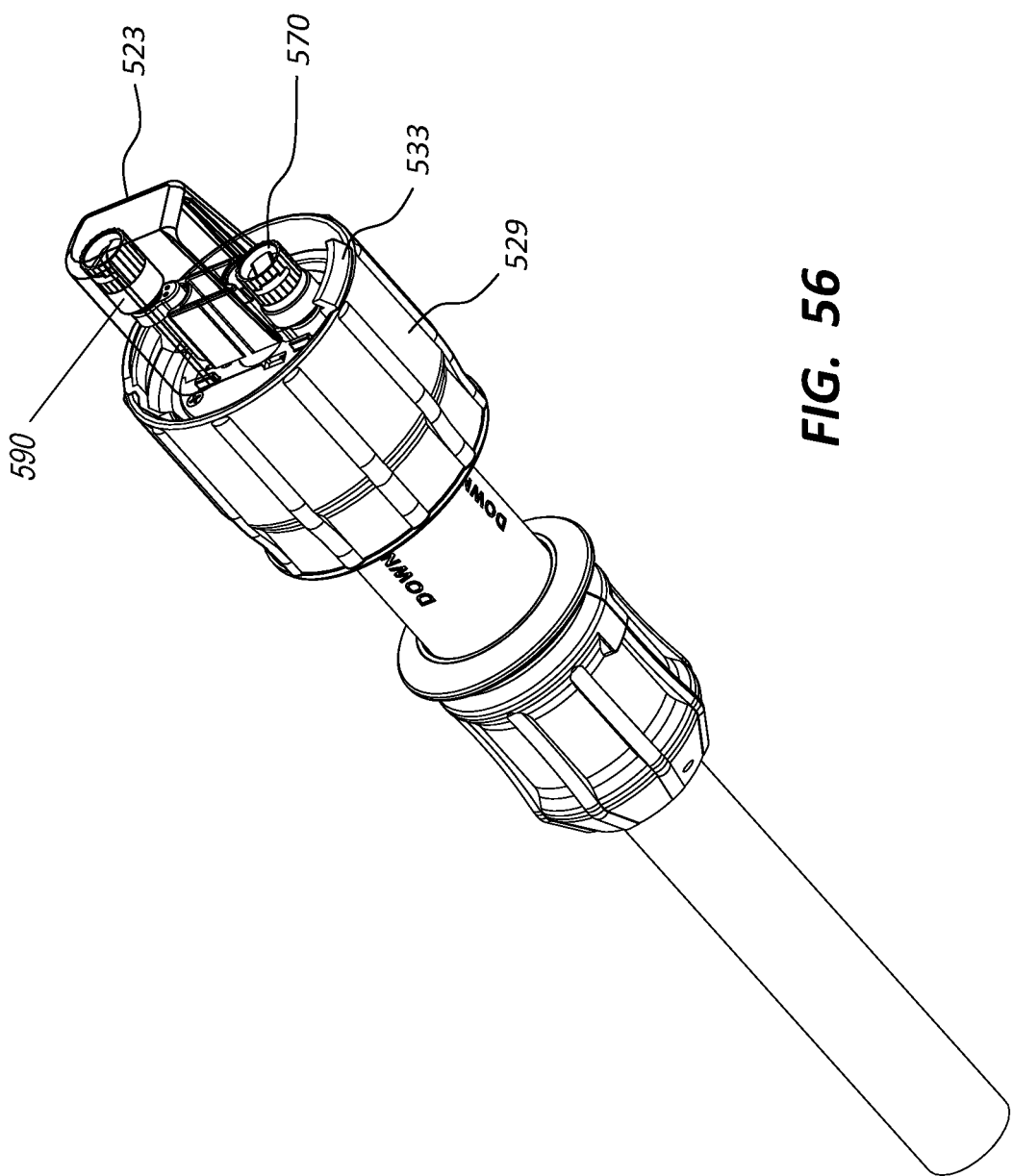

An example of the telescopic cap 529 in the second position is shown in FIG. 56. The telescopic cap 529 can be held in a distal position by one or more cap tabs 533 (e.g., providing a snap-fit function), as shown. In other embodiments, a deployment handle can include one or more stops, detents, clips, catches, or other fastening structures for keeping the telescopic cap in a proximal and/or distal position. In other embodiments, a telescopic cap can include a threaded inner surface and can be positioned on threads, such that translation of the telescopic cap results from rotating the telescopic cap upon the threads.

From the configuration shown in FIG. 56, an operator can remove a gripper line cap 570 to expose a gripper line. An operator may then optionally perform a gripper line removability check by ensuring the gripper line is moveable, though an operator may leave the gripper line in position until subsequent deployment steps (e.g., as a backup in case further manipulation of the gripper line is desired). As shown, the deployment handle 514 can include a lockout 523 (shown as transparent in this view) positioned so as to prevent an operator from gaining access to a lock line cap 590 prior to removing the gripper line cap 570.

Figure 57:
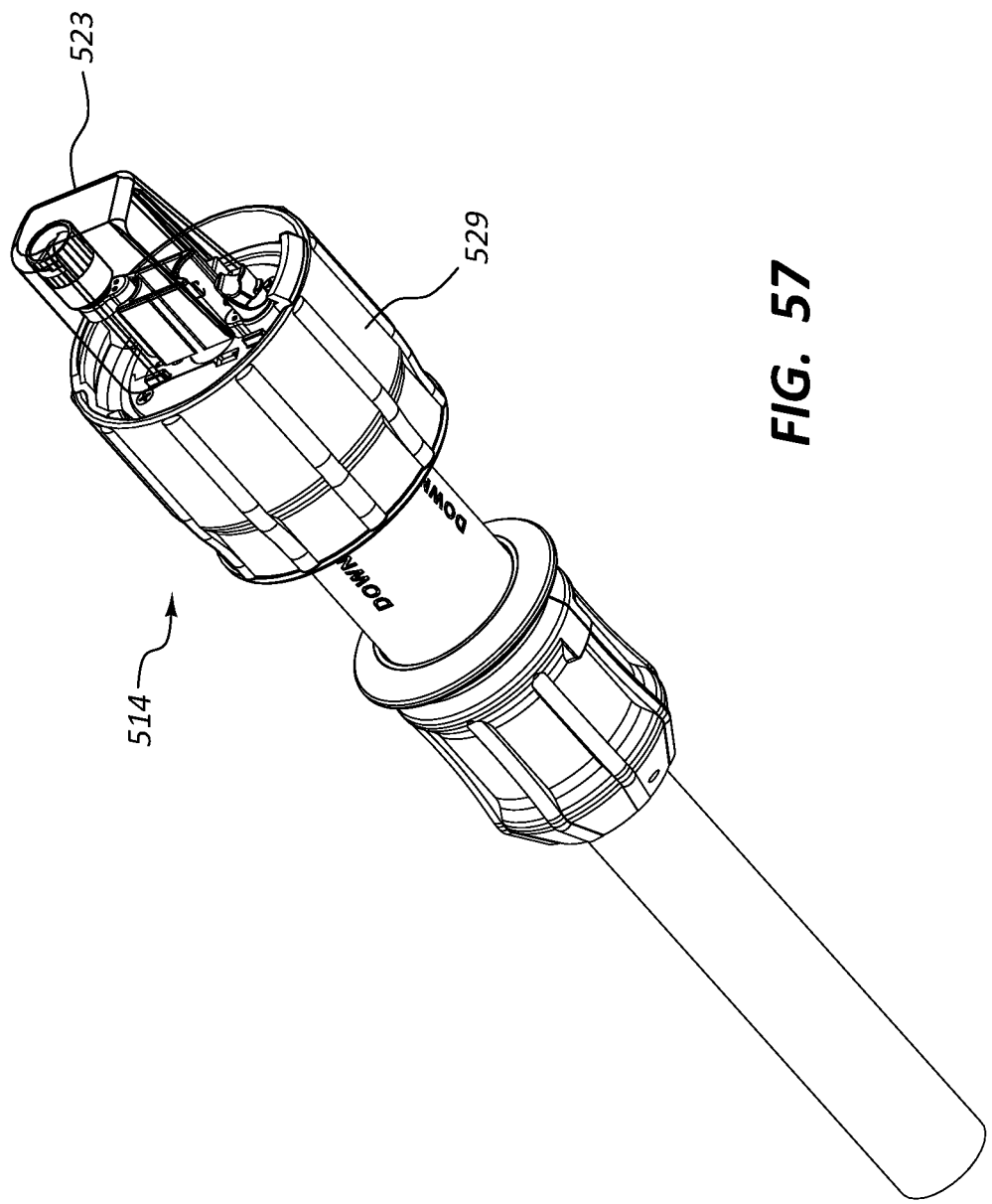
Figure 58:
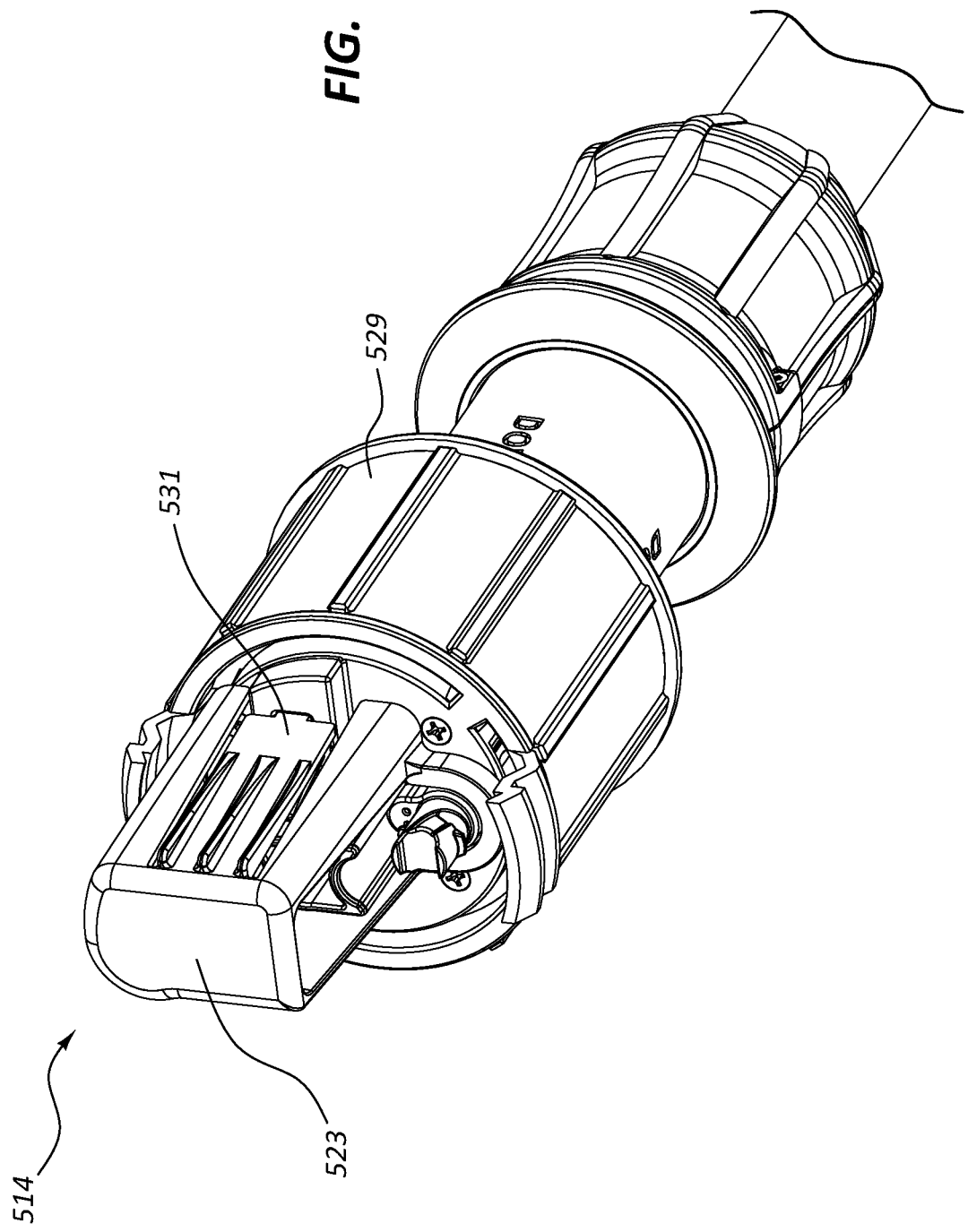

FIGS. 57-58 illustrate separate views of the deployment handle 514 after the gripper line cap 570 has been removed. As shown in FIG. 58, the lockout 523 can be configured so as to be held in place by a lockout tab 531. From this configuration, an operator can press the lockout tab 531 to disengage the lockout 523 from the deployment handle 514. In the illustrated embodiment, the step of removing the lockout 523 can ensure that the attached implantable device is properly positioned in a locked configuration.

Figure 59:
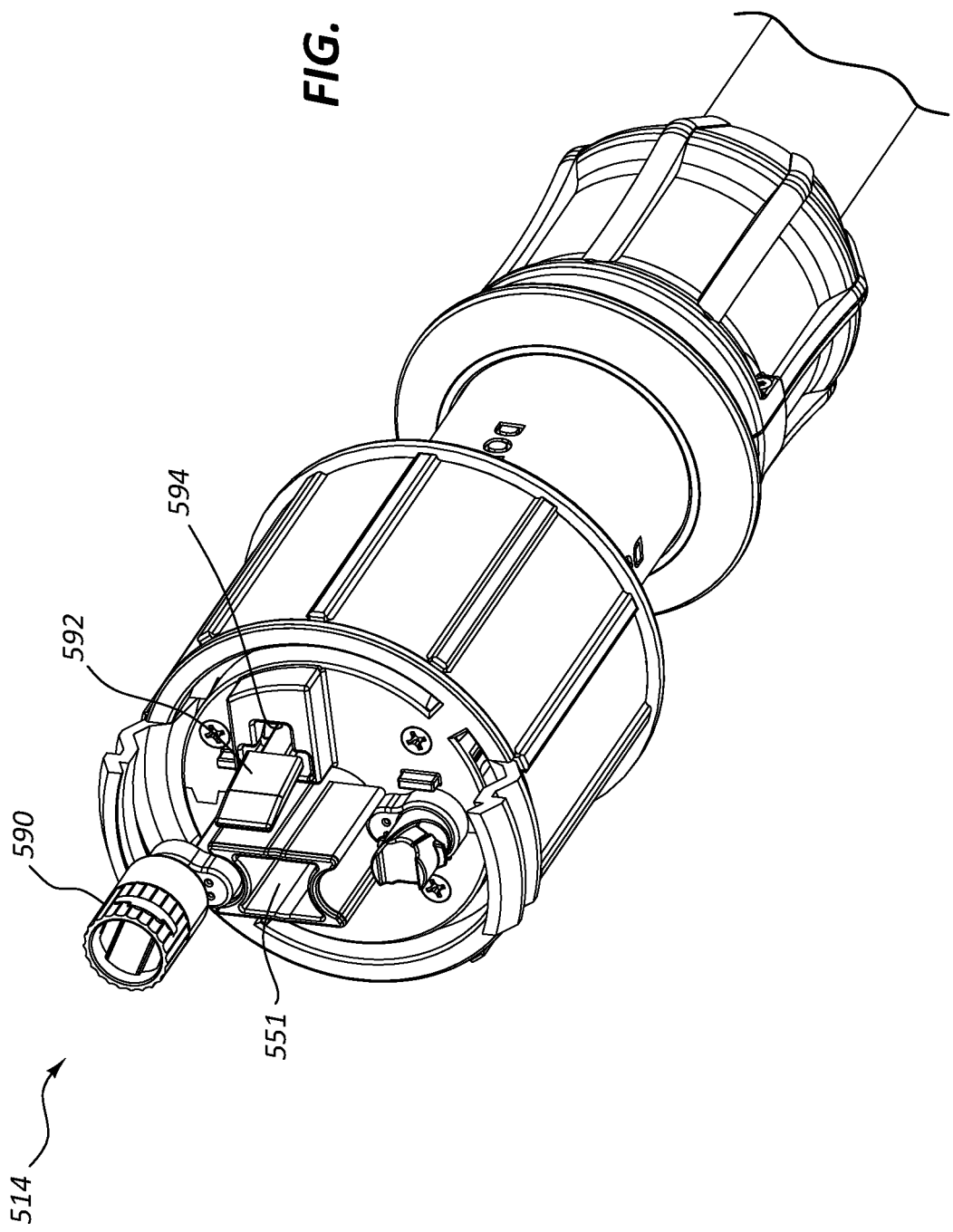

For example, FIG. 59 illustrates the deployment handle 514 with the lockout 523 removed. As shown, a lock tab 592 can be positioned through a lock slot 594, placing the attached implantable device in an unlocked configuration. In this embodiment, because the lock slot 594 is positioned adjacent to the lockout tab 531 (e.g., when the lockout 523 is in the position shown in FIG. 58), depression of the lockout tab 531 can move the lock tab 592 inwards, allowing it to move distally through the lock slot 594 and into a locked configuration. From this configuration, the lock line cap 590, actuator handle 551, and/or other components may be manipulated to further the staged deployment process as described above.

One or more embodiments of the present disclosure can include a deployment handle configured to provide staged deployment of an implantable device from a delivery device. In some embodiments, a deployment handle can include a lock cap removably attached to a housing lid and configured to prevent access to an actuator handle prior to removal of the lock cap. In some embodiments, a lock cap can be configured to engage with a lock tab (such as lock tab 392 described above) upon removal of the lock cap so as to allow a lock line assembly attached to the lock tab to move from an unlocked position toward a locked position, thereby ensuring that an attached implantable device is locked prior to being decoupled via actuation of the actuation handle.

Some embodiments may include an inner cap configured to function as a lock cap (such as inner cap 319 shown in FIGS. 50-51), and some embodiments may include a lockout configured to function as a lock cap (such as lockout 523 shown in FIGS. 55-58).

H. Handle Configuration and Operation

Figure 60:
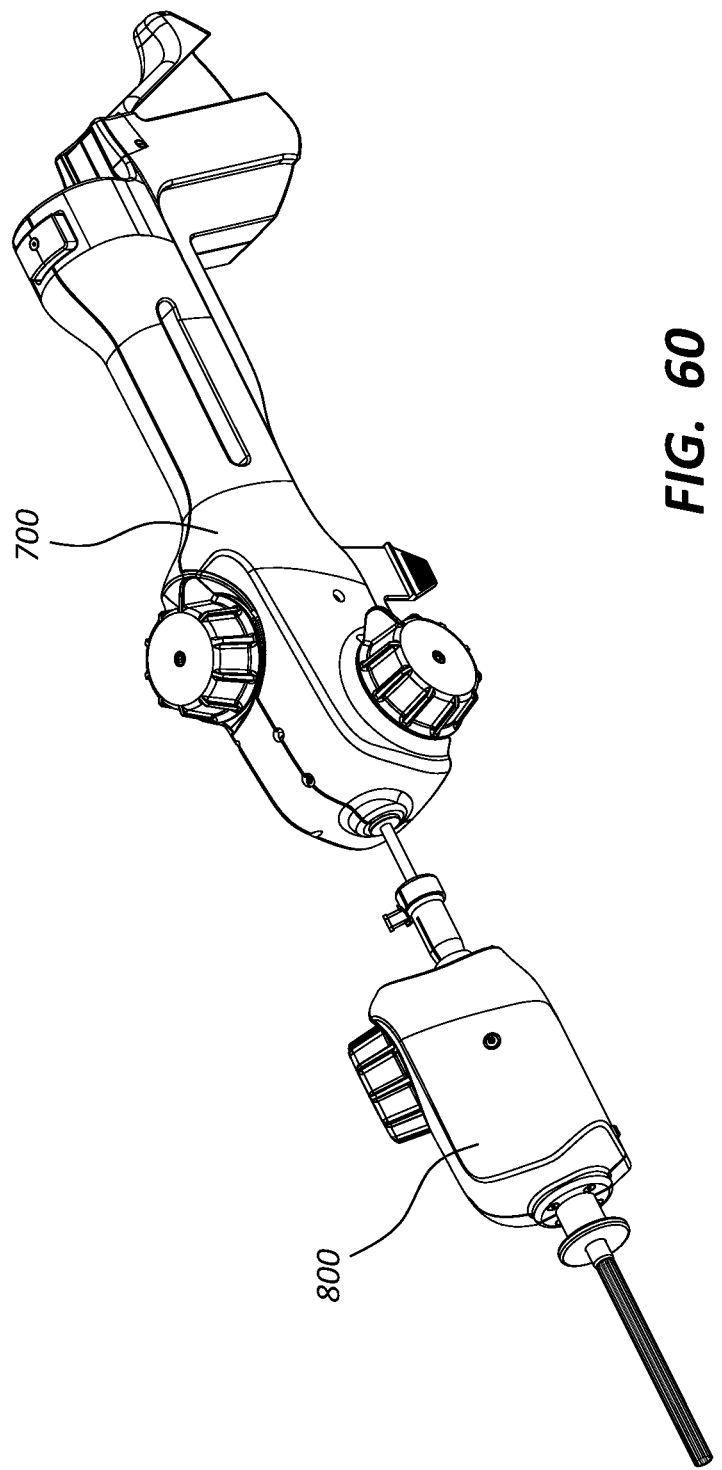
FIGS. 60 and 61A-61B illustrate various components of a delivery system according to the present disclosure.
Figure 61A:
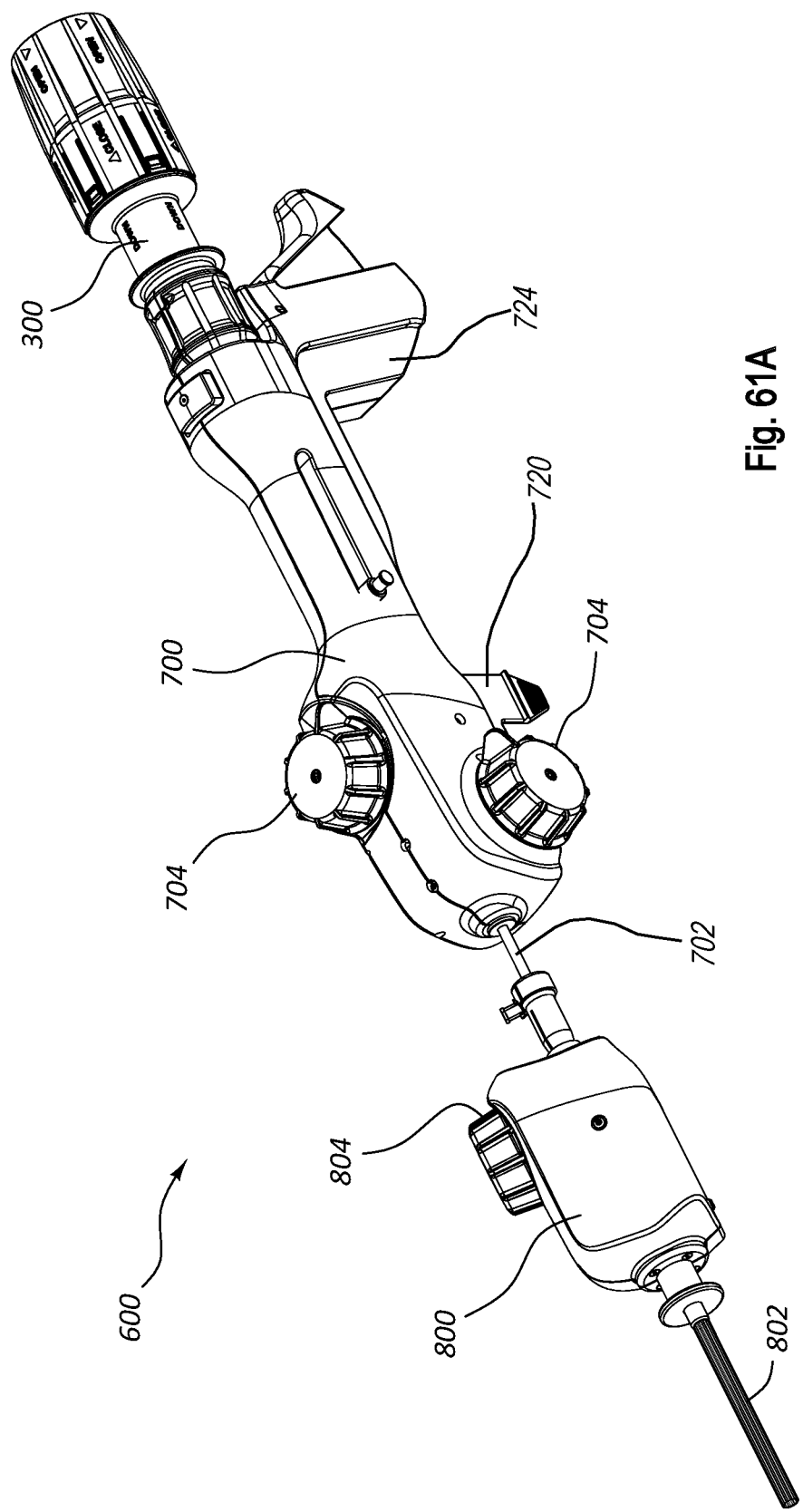
Figure 61B:
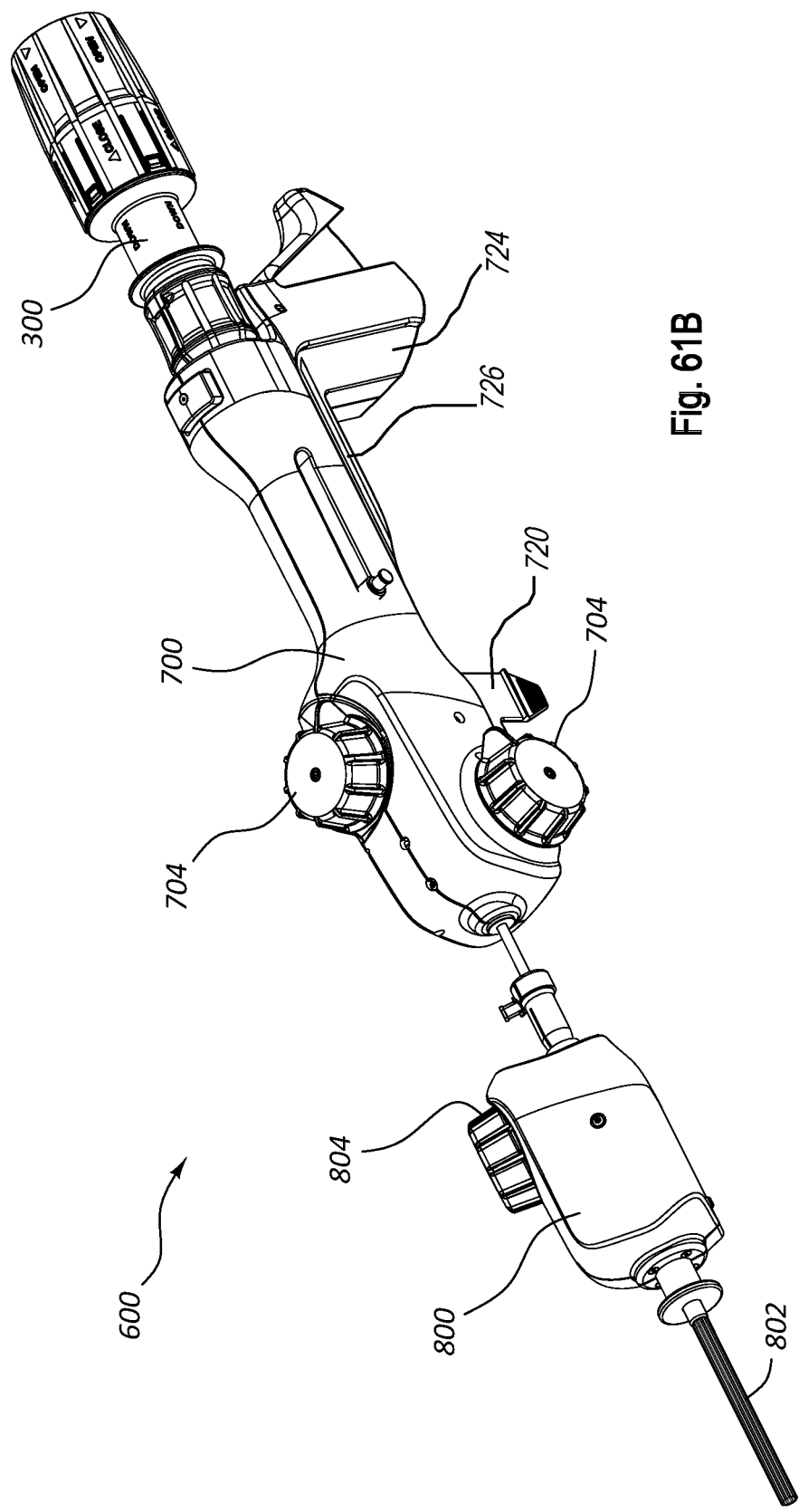

FIGS. 60, 61A, and 61B illustrate additional components that may be associated with a delivery device 300. As shown, the delivery device 300 can be associated with a sleeve housing 700 and/or a outer catheter housing 800. FIG. 61A illustrates delivery device 300 coupled to the sleeve housing 700 and outer catheter housing 800 as part of a medical device delivery system 600. In the illustrated embodiment, the delivery device 300 can be partially housed within the sleeve housing 700 to form a delivery handle. As shown, the sleeve housing 700 can include a sleeve 702 that extends distally from the sleeve housing 700. The sleeve 702 can be formed with a lumen for receiving the delivery catheter 302 (not visible in FIG. 61A) as the delivery catheter 302 extends from the delivery device 300 distally to the sleeve 702. As illustrated, the outer catheter housing 800 can include a outer catheter 802 that extends distally from the outer catheter housing 800. The outer catheter 802 can be formed with a lumen for receiving the sleeve 702 and/or delivery catheter 302 as the sleeve 702 extends distally from the sleeve housing 700 to the outer catheter housing 800 and/or as the delivery catheter 302 extends distally from the delivery device 300 to the outer catheter housing 800.

In some embodiments, the outer catheter 802 and/or sleeve 702 can be configured to be guidable. For example, in some embodiments, the outer catheter 802 can be configured to be steerable upon the actuation of steering knob 804 and/or the sleeve 702 can be configured to be steerable upon the actuation of one or more steering knobs 704. Examples of steering systems, including guidable catheters, sleeves, steering knobs, associated handle controls, and other related components are provided in U.S. Pat. No. 7,666,204, incorporated herein by reference in its entirety. Such a guidable catheter may be referred to herein as a "steerable guide catheter," "guide catheter," "steerable catheter," or "guidable catheter," and such a guidable sleeve may be referred to herein as a "steerable sleeve," "guide sleeve," "guidable sleeve," or "steerable guide sleeve."

As shown, the sleeve housing 700 may include means for securing the sleeve housing to a stabilizer, frame, table, bench, or other structure. Some embodiments include a sleeve housing tab 720 and/or chamfer 724 enabling the sleeve housing 700 to be secured to a stabilizer system. The sleeve housing tab 720 can configured to engage with corresponding receiving means (e.g., a receiving slot) in a stabilizer system, preferably allowing the sleeve housing 700 to be translatable upon the stabilizer system without uncoupling of the sleeve housing tab 720 from the corresponding receiving means. Similarly, the chamfer 724 can be configured to fit within a corresponding receiving portion of a stabilizer system (e.g., a support arm of the stabilizer system sized and shaped to receive the chamfer 724). In some embodiments, the chamfer 724 can be configured to enable a form fit or friction fit of the sleeve housing 700 into the corresponding receiving portion of the stabilizer system. Additionally, or alternatively, the sleeve housing 700 can include one or more other linkage means, such as clips, hooks, clasps, etc. configured for securing the medical device delivery system 600 or portions thereof to a stabilizer system or other support structure. FIG. 61B illustrates an embodiment having a grooved portion 726 in the chamfer 724. The grooved portion 726 can be configured to match a corresponding structure of a stabilizer system, such as a pin, rail, bar, or the like, thereby enabling and/or enhancing securement of the sleeve housing 700 to the stabilizer system. Examples of a stabilizer system to which embodiments of medical device delivery systems can be attached may be found in U.S. patent application Ser. No. 14/879,674, filed Oct. 9, 2015.

Figure 62:
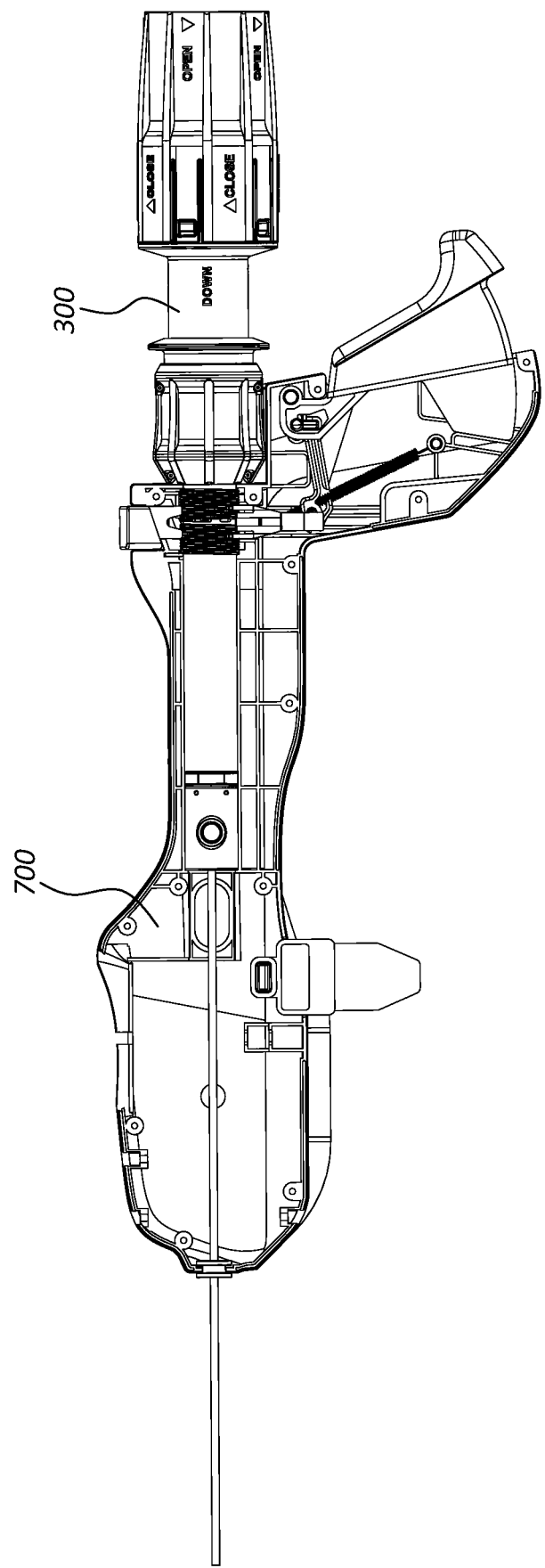
FIGS. 62-63 illustrate an embodiment of a delivery system handle.
Figure 63:
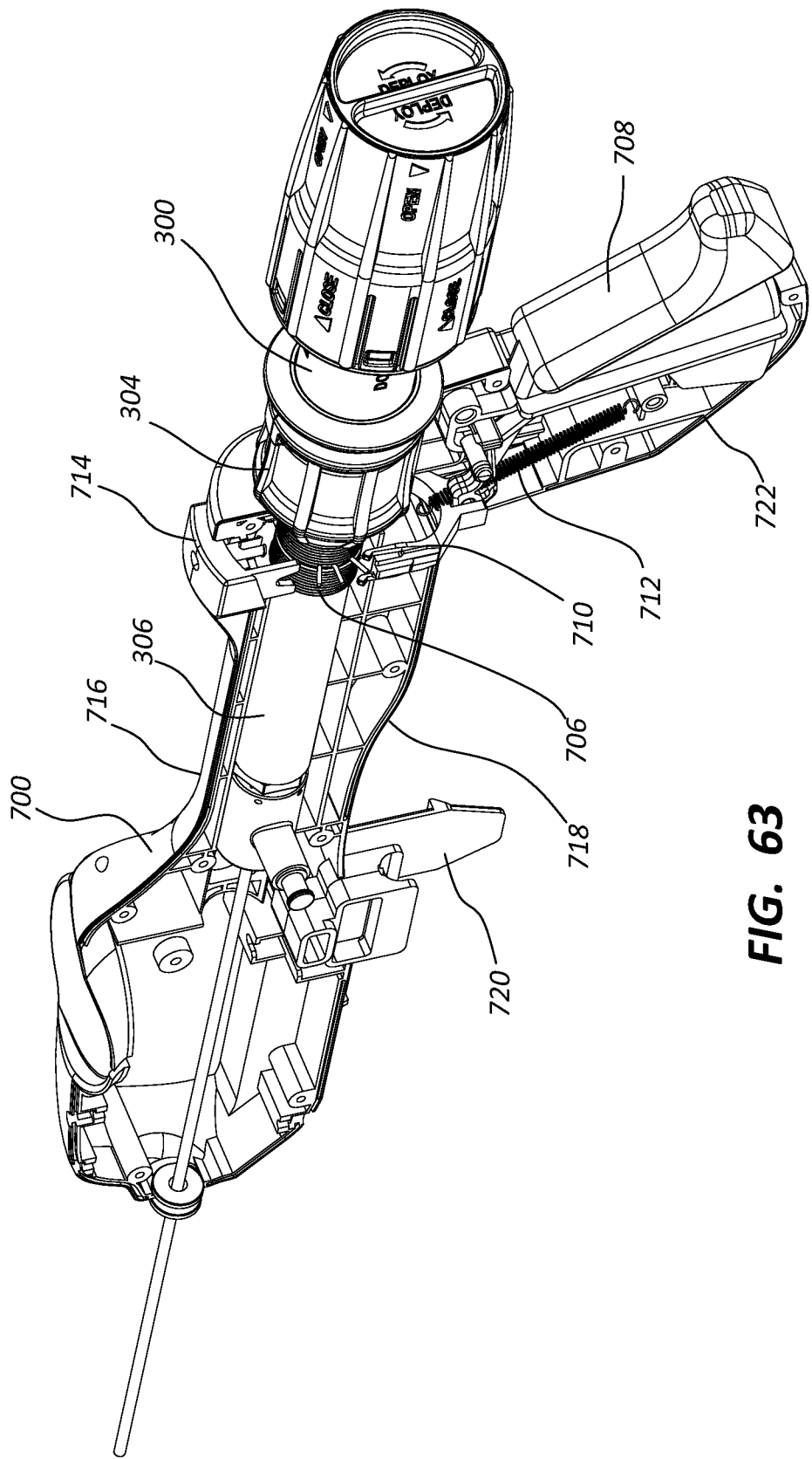

FIGS. 62-63 illustrate a delivery device 300 partially housed within a sleeve housing 700, with a portion of the sleeve housing 700 shown in cutaway view for clarity. As illustrated, the shell 306 of the delivery device 300 can extend into the sleeve housing 700. The sleeve housing 700 can be configured to secure the delivery device 300 while allowing the position of the delivery device 300 to be adjusted relative to the sleeve housing 700. For example, the sleeve housing 700 can include a lock, such as spring clamp 706 positioned around the delivery device 300 when the delivery device 300 is inserted and/or housed within the sleeve housing 700. The spring clamp 706 can be configured to have a diameter that is smaller when the spring clamp 706 is in a relaxed configuration than when the spring clamp 706 is in a stressed configuration (e.g., the spring clamp 706 can include one or more torsion springs).

For example, when the spring clamp 706 is in a relaxed configuration, the spring clamp 706 can tighten against the delivery device 300 to secure the delivery device 300 in position relative to the sleeve housing 700 (e.g., to prevent translation and/or rotation of the delivery device 300). When the spring clamp 706 is placed in a stressed configuration, the diameter of the spring clamp 706 can enlarge to allow the delivery device 300 to freely translate and/or rotate relative to the sleeve housing 700. For example, the spring clamp 706 can be formed with one or more arms extending radially outward from the spring clamp 706. Repositioning of the one or more arms (e.g., relative to each other and/or relative to the spring clamp 706) can move the spring clamp 706 toward a stressed (i.e., unlocked) configuration or toward a relaxed (i.e., locked) configuration.

Other embodiments may include one or more other mechanisms for adjustably securing a delivery device to a sleeve housing. For example, some embodiments may include a lock configured as a set screw for adjustably securing a delivery device to a sleeve housing; some embodiments may include one or more locks configured as clips, clasps, flanges, tabs, brackets, latches, bolts, or other adjustable securing means; and some embodiments may include one or more locks configured as magnetic components, hook and loop fasteners (e.g., Velcro®), spring button locks, and/or a pin and hole assembly for adjustably securing a delivery device and a sleeve housing.

As illustrated, the sleeve housing 700 can include a handle 708. The handle 708 can be engageable with the spring clamp 706 such that actuation of the handle 708 adjusts the spring clamp 706 (e.g., toward a relaxed configuration or toward a stressed configuration). The handle 708 can be coupled to a lock actuator. As shown in the illustrated embodiment, the lock actuator can be configured as a yoke 710. The yoke 710 can be configured so as to engage with the spring clamp 706 upon actuation (e.g., depression) of the handle 708. For example, in some embodiments, depression of the handle 708 can move the yoke 710 into contact with one or more arms of the spring clamp 706. Further movement of the yoke 710 can adjust the position of the one or more arms of the spring clamp 706, thereby positioning the spring clamp 706 toward a stressed configuration or toward a relaxed configuration. For example, depression of the handle 708 can move the spring clamp 706 toward a stressed configuration, providing a larger diameter for the shell 306 of the delivery device 300 to be translated and/or rotated within the spring clamp 706.

As shown, the yoke 710 can have a furcated shape. The yoke 710 can be configured to fit partially around the spring clamp 706 and/or shell 306. For example, the yoke 710 can be configured in size and shape so as to be capable of engaging with one or more arms of the spring clamp 706 without contacting the shell 306 and/or other portions of the spring clamp 706.

As illustrated, the sleeve housing 700 can also include a handle spring 712. The handle spring 712 can be configured to apply a force directing the handle 708 and/or yoke 710 towards a default position (e.g., a position associated with a locked configuration). For example, the handle spring 712 can be coupled to the yoke 710 at a first end and to the sleeve housing 700 at a second end such that tension in the handle spring 712 can pull the yoke 710 away from the spring clamp 706 in the absence of an overriding force. Other embodiments may additionally or alternatively include one or more coil springs and/or leaf springs, such as a coil or leaf spring configured to push or pull a yoke away from a spring clamp or a coil or leaf spring configured to push or pull a handle toward a default position (e.g., a position associated with a locked configuration).

In some embodiments, the handle 708 can be configured to be selectively held in a depressed position (e.g., as opposed to automatically reverting back to a default position upon removal of the depressing force). For example, the sleeve housing 700 can include an override configured to engage with the handle 708 to prevent movement of the handle 708. The override and/or handle can be configured to prevent movement of the handle toward the default position, toward the depressed position, or in either direction upon engaging the override against the handle 708. For example, the override can be configured as a pin, latch, clasp, stop, or other structure that extends out of or partially out of the sleeve housing 700. In some embodiments, the override can be configured to maintain the handle in a depressed position when engaged with the handle.

The override can be inserted into or further into the sleeve housing 700 so as to engage with the handle 708 and limit movement of the handle 708. For example, the override and or handle 708 may be configured such that, after the handle 708 has been moved to a depressed position (e.g., to unlock the delivery device 300), the override may be engaged so as to prevent the handle 708 from automatically returning to the default position. In this configuration, the delivery device can remain free to translate and/or rotate relative to the sleeve housing 700 without the need for constant pressure against the handle 708.

As illustrated, the sleeve housing 700 can also include a lock button 714 configured to engage with the spring clamp 706 to move the spring clamp 706 from the locked configuration toward the unlocked configuration. The lock button 714 can be positioned at a location on the sleeve housing 700 opposite the handle 708. For example, as illustrated, the lock button 714 can be positioned on an upper portion 716 of the sleeve housing 700 and/or above the delivery device 300. The lock button 714 may be configured to be engageable with the spring clamp 706 such that actuation of the lock button 714 adjusts the spring clamp 706 (e.g., toward a relaxed configuration or toward a stressed configuration). For example, depression of the lock button 714 can move the spring clamp 706 toward a stressed configuration, providing a larger diameter for the shell 306 of the delivery device 300 to be translated and/or rotated within the spring clamp 706.

In some embodiments, the lock button 714 can be configured so as to maintain position after being actuated. For example, some embodiments may include a lock button that maintains engagement with a spring lock or other locking means after being actuated (e.g., after being depressed). In other embodiments, a lock button may return to a default position upon removal of an actuating force. For example, in some embodiments, a lock button may be allowed to return to a locked configuration upon removal of an actuating force.

In some embodiments, a delivery device can include a clutch case disposed on a portion of the delivery device positioned within a sleeve housing (e.g., disposed on a shell of the delivery device). In such embodiments, the sleeve housing may include a binding plate configured to extend through the sleeve housing. The binding plate can be adjustably positioned to engage with the clutch case to prevent translation of the delivery device. For example, the binding plate can be configured to fall into position within and/or against the clutch case when the delivery device is positioned so as to bring the clutch case or receiving portion thereof below the binding plate, thereby preventing further translation of the delivery device.

As illustrated, the sleeve housing 700 and/or delivery device 300 can be configured to operate together to allow translation and/or rotation of the delivery device 300 relative to the sleeve housing 700. One or more embodiments may be configured to beneficially allow one-handed operation of the delivery device 300. For example, the handle 708 can be located in a position relative to the delivery device 300 that allows simultaneous manipulation of the delivery device 300 and control of the handle 708. In some embodiments, the handle 708 or portion thereof can be positioned below the translation knob 304 of the delivery device 300 and/or can be positioned from a lower portion 718 of the sleeve housing.

As illustrated, the sleeve housing 700 can include a grip section 722 extending transversely from a longitudinal axis of the sleeve housing 700 and/or delivery device 300. The handle 708 can be disposed on a proximal side of the grip section 722. From such a configuration, an operator may depress the handle 708 using the palm of his/her hand in order to unlock the delivery device 300 from the sleeve housing 700. With his/her hand in this position (e.g., while still maintaining force against the handle 708), the operator can freely manipulate the delivery device 300 (e.g., by manipulating the translation knob 304) using the thumb and/or fingers of his/her same hand.

The illustrated embodiment can also allow one-handed operation from the upper portion of the sleeve housing 700. For example, an operator may position his/her hand above the sleeve housing 700. From this position, the operator may actuate the lock button 714 and/or grasp the translation knob 304. For example, an operator may use his/her palm, a thumb and/or other fingers to actuate the lock button 714 while using the palm, thumb, and/or other fingers of the same hand to manipulate the delivery device 300 (e.g., by manipulating the translation knob 304 of the delivery device 300). As shown, the translation knob 304 may be positioned on a portion of the delivery device 300 exterior to the sleeve housing 700 so as to allow a user to manipulate the translation knob 304.

Some embodiments may include different configurations of handles and/or lock buttons. For example, some embodiments may omit lock buttons or handles, some embodiments may include two or more lock buttons (e.g., by replacing the handle 708 of the illustrated embodiment with a lock button), and some embodiments may include two or more handles (e.g., by replacing the lock button 714 of the illustrated embodiment with a handle). Some embodiments may include one or more lock buttons and/or handles disposed at different locations on a sleeve housing, such as one or more lock buttons and/or handles extending from a side portion of the sleeve housing and/or extending horizontally, vertically, or diagonally.

The one-handed operation made possible by certain embodiments disclosed herein can provide a number of benefits. For example, an operator may manipulate the position of the delivery device 300 relative to the sleeve housing 700 with one hand, freeing the other hand to manipulate and/or actuate other components of the delivery system 600, such as the deployment handle 314, outer catheter housing 800, steering knobs 704, 804, fluid management system 308, and/or collar 310.

I. Industrial Applicability

It will be appreciated that delivery systems of the present disclosure may include any or all of the components described herein. In addition, delivery systems of the present disclosure may be used to introduce other delivery catheters, interventional catheters, introducers, guiding systems, and/or other devices. Likewise, delivery devices may be used to deliver a variety of types of devices to a target location within the body, including endoscopic staples, heart valves, annuloplasty rings, and/or other medical devices used in angioplasty, atherectomy, stent-delivery, embolic filtration and removal, septal defect repair, tissue approximation and repair, vascular clamping and ligation, electrophysiology mapping or ablation, suturing, aneurysm repair, and/or vascular occlusion, for example.

The embodiments of the present disclosure can be used in a variety of industrial applications. For example, some embodiments include a method of positioning a medical device using a stabilizing system according to the present disclosure, and such systems, devices, and methods can be used in a medical procedure where manipulation and positioning of a medical device is required and/or desired.

In addition, such systems, devices, and methods can be applied in a medical products testing industry or medical products analysis industry. For example, the ability of a medical device to be supported, positioned, reoriented, and/or manipulated can be tested and analyzed using the devices, systems, and methods of the present disclosure.

Further, operational and durability limits of a medical device under such uses can be tested and/or analyzed.

In addition, embodiments of the present disclosure can be used in a medical operator training industry. For example, one or more devices, systems, or methods of the present disclosure can be used in a training application allowing a physician, surgeon, doctor, or medical engineer to undergo training by positioning, manipulating, reorienting, and/or repositioning a medical device.

While the foregoing is a complete description of the preferred embodiments, various alternatives, substitutions, additions, modifications, and equivalents are possible without departing from the scope of the invention. For example, in many of the above-described embodiments, the invention is described in the context of approaching a valve structure from the upstream side, that is, the atrial side in the case of a mitral valve. It should be understood that any of the foregoing embodiments may be utilized in other approaches as well, including from the ventricular or downstream side of the valve, as well as using surgical approaches through a wall of the heart. Moreover, various embodiments may be used in the treatment of a variety of other tissue structures besides heart valves, and will find usefulness in a variety of tissue approximation, attachment, closure, clamping and ligation applications, some endovascular, some endoscopic, and some open surgical.

The terms "approximately," "about," and "substantially" as used herein represent an amount or condition close to the stated amount or condition that still performs a desired function or achieves a desired result. For example, the terms "approximately," "about," and "substantially" may refer to an amount that deviates by less than 10%, or by less than 5%, or by less than 1%, or by less than 0.1%, or by less than 0.01% from a stated amount or condition.

In addition, unless expressly described otherwise, all stated amounts (e.g., angle measurements, dimension measurements, etc.) are to be interpreted as being "approximately," "about," and/or "substantially" the stated amount, regardless of whether the terms "approximately," "about," and/or "substantially" are expressly stated in relation to the stated amount(s).

Further, elements described in relation to any embodiment depicted and/or described herein may be combinable with elements described in relation to any other embodiment depicted and/or described herein. For example, any element described in relation to an embodiment depicted in FIGS. 4 through 31 may be combinable with an embodiment described depicted in FIGS. 32 through 63.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A delivery system for staged deployment of an implantable device at a target area, the delivery system comprising:
   a delivery catheter having a proximal end and a distal end;
   an adjustable implantable device coupled to the distal end of the delivery catheter; and
   a delivery device coupled to the proximal end of the delivery catheter, the delivery device including a deployment handle and one or more lock lines extending from the deployment handle through the catheter to the implantable device, the one or more lock lines being configured to engage with the implantable device to allow locking of the implantable device, the deployment handle including:
   a lock cap removably attached to a housing lid;
   a lock line assembly coupled to the one or more lock lines and configured to lock the implantable device by moving from an unlocked position toward a locked position, the lock line assembly including a lock tab configured to lodge within a lock slot disposed on the housing lid so as to hold the lock line assembly in the unlocked position; and
   an actuator handle at least partially enclosed by the lock cap, the actuator handle being configured to provide decoupling of the implantable device from the delivery device upon actuation of the actuator handle;
   wherein the lock cap is configured to prevent access to the actuator handle prior to removal, and is configured to engage with the lock tab upon removal of the lock cap so as to dislodge the lock tab to allow the lock line assembly to move toward the locked position to lock the implantable device; and
   further wherein the lock cap includes a tab configured to pass over the lock slot upon rotation of the lock cap.

2. The system of claim 1, further comprising a lockout configured to prevent access to a second control line cap prior to removal of a first control line cap.

3. The system of claim 2, wherein the lockout includes a lip positioned underneath the first control line cap, the lip being configured in size and shape so as to prevent movement of the lockout prior to removal of the first control line cap.

4. The system of claim 2, wherein the first control line cap is a gripper line cap, and wherein the second control line cap is a lock line cap.

5. The system of claim 1, wherein the actuator handle is prevented from being actuated prior to removal of a first control line cap and a second control line cap.

6. The system of claim 5, wherein the actuator includes one or more indented portions configured such that the first control line cap and the second control line cap at least partially fit within the one or more indented portions to prevent rotation of the actuator handle prior to removal of the first control line cap and the second control line cap.

7. The system of claim 1, further comprising a telescopic cap configured to be slidable from a first position at least partially preventing access to the lock cap to a second position providing access to the lock cap.

8. The system of claim 7, further comprising one or more tabs configured to hold the telescopic cap in the second position.

9. The system of claim 7, wherein the lock cap includes a lockout tab configured to pass over the lock slot upon depression of the lockout tab.

10. The system of claim 1, wherein the adjustable implant includes a pair of opposed distal elements rotatably connected to a coupling member and a gripper disposed proximal to the distal elements and configured to bias toward the distal elements so as to engage with tissue disposed between the distal elements and the gripper.

11. A delivery system for staged deployment of an implantable device at a target area, the delivery system comprising:
   a delivery catheter having a proximal end and a distal end;
   an adjustable implantable device coupled to the distal end of the delivery catheter; and
   a delivery device coupled to the proximal end of the delivery catheter, the delivery device including a deployment handle and one or more lock lines extending from the deployment handle through the catheter to the implantable device, the one or more lock lines being configured to engage with the implantable device to allow locking of the implantable device, the deployment handle including:
a lock cap removably attached to a housing lid;
a lock line assembly coupled to the one or more lock lines and configured to lock the implantable device by moving from an unlocked position toward a locked position, the lock line assembly including a lock tab configured to lodge within a lock slot disposed on the housing lid so as to hold the lock line assembly in the unlocked position;
an actuator handle at least partially enclosed by the lock cap, the actuator handle being configured to provide decoupling of the implantable device from the delivery device upon actuation of the actuator handle; and
a lockout configured to prevent access to a second control line cap prior to removal of a first control line cap;
wherein the lock cap is configured to prevent access to the actuator handle prior to removal, and is configured to engage with the lock tab upon removal of the lock cap so as to dislodge the lock tab to allow the lock line assembly to move toward the locked position to lock the implantable device.

12. The delivery system of claim 11, wherein the lock cap includes a tab configured to pass over the lock slot upon rotation of the lock cap.

13. The delivery system of claim 11, wherein the actuator handle is prevented from being actuated prior to removal of a first control line cap and a second control line cap.

14. The delivery system of claim 11, wherein the lock cap includes a lockout tab configured to pass over the lock slot upon depression of the lockout tab.

15. A method of deploying an implantable device at a target area, the method comprising:
positioning the implantable device at a target area, the implantable device being coupled to a distal end of a delivery catheter and a deployment handle being coupled to a proximal end of the delivery catheter, wherein one or more lock lines extend from the deployment handle through the catheter to engage with the implantable device such that application or release of tension in the one or more lock lines provides locking of the implantable device, the deployment handle including:
a lock cap removably attached to a housing lid;
a lock line assembly coupled to the one or more lock lines and configured to apply or release tension in the one or more lock lines by moving from an unlocked position toward a locked position, the lock line assembly including a lock tab configured to lodge within a slot disposed on the housing lid so as to hold the lock line assembly in the unlocked position; and
an actuator handle at least partially enclosed by the lock cap, the actuator handle being configured to provide decoupling of the implantable device from the delivery catheter upon actuation of the actuator handle;
wherein the lock cap is configured to prevent access to the actuator handle prior to removal, and is configured to engage with the lock tab upon removal of the lock cap so as to dislodge the lock tab to allow the lock line assembly to move toward the locked position;
orienting the implantable device in a desired configuration; and
removing the lock cap to lock the implantable device.

16. The method of claim 15, further comprising removing a gripper line cap prior to removing a lock line cap, the deployment handle including a lockout configured to prevent access to the lock line cap prior to removal of the gripper line cap.

17. The method of claim 16, further comprising removing the one or more lock lines after removal of the lock line cap.

18. The method of claim 16, further comprising decoupling the implantable device from the delivery catheter by actuating the actuator handle, the actuator handle being configured so as to be prevented from being actuated prior to removal of the gripper line cap and the lock line cap.

19. The method of claim 15, further comprising decoupling the implantable device from the delivery catheter by actuating the actuator handle, the actuator handle being configured so as to be prevented from being actuated prior to removal of a gripper line cap and a lock line cap.

* * * * *